United States Patent
Jewett et al.

(10) Patent No.: US 11,814,621 B2
(45) Date of Patent: Nov. 14, 2023

(54) EXPANDING THE CHEMICAL SUBSTRATES FOR GENETIC CODE REPROGRAMMING

(71) Applicant: Northwestern University, Evanston, IL (US)

(72) Inventors: Michael Christopher Jewett, Evanston, IL (US); Joongoo Lee, Evanston, IL (US); Jeffrey S. Moore, Savoy, IL (US); Kenneth E. Schwieter, Champaign, IL (US); Kevin Jerome Schwarz, Champaign, IL (US)

(73) Assignees: Northwestern University, Evanston, IL (US); The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 15/734,182

(22) PCT Filed: Jun. 3, 2019

(86) PCT No.: PCT/US2019/035215
§ 371 (c)(1),
(2) Date: Dec. 1, 2020

(87) PCT Pub. No.: WO2020/040840
PCT Pub. Date: Feb. 27, 2020

(65) Prior Publication Data
US 2021/0230586 A1    Jul. 29, 2021

Related U.S. Application Data

(60) Provisional application No. 62/679,350, filed on Jun. 1, 2018.

(51) Int. Cl.
| | | |
|---|---|---|
| *C12N 15/113* | (2010.01) | |
| *C12P 19/34* | (2006.01) | |
| *C12N 15/11* | (2006.01) | |

(52) U.S. Cl.
CPC .......... *C12N 15/113* (2013.01); *C12N 15/11* (2013.01); *C12P 19/34* (2013.01); *C12N 2310/351* (2013.01)

(58) Field of Classification Search
CPC ............................ C12N 15/113; C12N 15/11; C12N 2310/351; C12P 19/34
USPC ...................................................... 435/69.1
See application file for complete search history.

(56) References Cited

U.S. PATENT DOCUMENTS

| | | |
|---|---|---|
| 4,458,066 A | 7/1984 | Caruthers |
| 4,683,195 A | 7/1987 | Mullis |
| 4,683,202 A | 7/1987 | Mullis |
| 5,478,730 A | 12/1995 | Alakhov |
| 5,494,810 A | 2/1996 | Barany |
| 5,556,769 A | 9/1996 | Wu |
| 5,665,563 A | 9/1997 | Beckler |
| 5,866,592 A * | 2/1999 | Hayashi ............... C07D 405/06 514/13.8 |
| 6,168,931 B1 | 1/2001 | Swartz |
| 6,518,058 B1 | 2/2003 | Biryukov et al. |
| 6,548,276 B2 | 4/2003 | Swartz |
| 6,783,957 B1 | 8/2004 | Biryukov et al. |
| 6,869,774 B2 | 3/2005 | Endo |
| 6,994,986 B2 | 2/2006 | Swartz |
| 7,008,651 B2 | 3/2006 | Ambuel |
| 7,118,883 B2 | 10/2006 | Inoue |
| 7,186,525 B2 | 3/2007 | Sakanyan |
| 7,189,528 B2 | 3/2007 | Higashide |
| 7,235,382 B2 | 6/2007 | Endo |
| 7,273,615 B2 | 9/2007 | Endo |
| 7,312,049 B2 | 12/2007 | Calhoun |
| 7,338,789 B2 | 3/2008 | Swartz |
| 7,387,884 B2 | 6/2008 | Suzuki |
| 7,399,610 B2 | 7/2008 | Shikata |
| 7,776,535 B2 | 8/2010 | Mehl |
| 7,817,794 B2 | 10/2010 | Galvin |
| 8,298,759 B2 | 10/2012 | Voloshin |
| 8,357,529 B2 | 1/2013 | Swartz |
| 8,715,958 B2 | 5/2014 | Goerke |
| 8,734,856 B2 | 5/2014 | Endo |
| 9,005,920 B2 | 4/2015 | Kusumegi |
| 9,410,148 B2 | 8/2016 | Suga |

(Continued)

FOREIGN PATENT DOCUMENTS

| | | |
|---|---|---|
| EP | 1964916 A1 | 9/2008 |
| EP | 2141175 B1 | 1/2010 |

(Continued)

OTHER PUBLICATIONS

Adaligil et al. Ribosomal Synthesis of Macrocyclic Peptides with Linear γ4- and β-Hydroxy-γ4-amino Acids. ACS Chem. Biol. 2021, 16, 1325-1331. (Year: 2021).*
Iqbal et al. Ribosomal incorporation of backbone modified amino acids via an editing-deficient aminoacyl-tRNA synthetase. Org. Biomol. Chem., 2018, 16, 1073 (Jan. 2018). (Year: 2018).*
Kawakami et al. Extensive Reprogramming of the Genetic Code for Genetically Encoded Synthesis of Highly N-Alkylated Polycyclic Peptidomimetics. J. Am. Chem. Soc. 2013, 135, 12297-12304. (Year: 2013).*
Albayrak, C. et al. Cell-free co-production of an orthogonal transfer RNA activates efficient site-specific non-natural amino acid incorporation. Nucleic Acids Res 41, 5949-5963 (2013).

(Continued)

*Primary Examiner* — Yih-Horng Shiao
(74) *Attorney, Agent, or Firm* — Quarles & Brady LLP

(57) ABSTRACT

Disclosed are methods, systems, components, and compositions for synthesis of sequence defined polymers. The methods, systems, components, and compositions may be utilized for incorporating novel substrates that include non-standard amino acid monomers and non-amino acid monomers into sequence defined polymers. As disclosed herein, the novel substrates may be utilized for acylation of tRNA via flexizyme catalyzed reactions. The tRNAs thus acylated with the novel substrates may be utilized in synthesis platforms for incorporating the novel substrates into a sequence defined polymer.

20 Claims, 35 Drawing Sheets

Specification includes a Sequence Listing.

(56) References Cited

U.S. PATENT DOCUMENTS

| | | |
|---|---|---|
| 9,410,170 B2 | 8/2016 | Calhoun |
| 9,528,137 B2 | 12/2016 | Jewett |
| 9,688,994 B2 | 6/2017 | Lajoie |
| 9,783,800 B2 | 10/2017 | Suga |
| 9,943,360 B2 | 4/2018 | Miller |
| 9,951,392 B2 | 4/2018 | Jewett |
| 10,017,728 B2 | 7/2018 | Jewett |
| 10,118,950 B2 | 11/2018 | Jewett |
| 10,457,932 B2 | 10/2019 | Jewett |
| 10,465,221 B2 | 11/2019 | Jewett |
| 10,577,632 B2 | 3/2020 | Jewett |
| 10,590,456 B2 | 3/2020 | Jewett |
| 10,829,795 B2 | 11/2020 | Jewett |
| 2007/0154983 A1 | 7/2007 | Calhoun |
| 2008/0138857 A1 | 6/2008 | Swartz |
| 2009/0281280 A1 | 11/2009 | Suga |
| 2012/0171720 A1 | 7/2012 | Church |
| 2012/0208720 A1 | 8/2012 | Kashiwagi |
| 2013/0316910 A1 | 11/2013 | Suga |
| 2014/0018257 A1 | 1/2014 | Suga |
| 2014/0045267 A1 | 2/2014 | Lajoie |
| 2014/0295492 A1 | 10/2014 | Jewett |
| 2014/0349353 A1 | 11/2014 | Nomura |
| 2015/0080549 A1 | 3/2015 | Kariyuki |
| 2015/0259757 A1 | 9/2015 | Jewett |
| 2016/0060301 A1 | 3/2016 | Jewett |
| 2016/0068835 A1 | 3/2016 | Reid |
| 2016/0083688 A1 | 3/2016 | Jewett |
| 2016/0209421 A1 | 7/2016 | Suga |
| 2016/0289668 A1 | 10/2016 | Murakami |
| 2016/0362708 A1 | 12/2016 | Jewett |
| 2017/0073381 A1 | 3/2017 | Jewett |
| 2017/0183666 A1 | 6/2017 | Lajoie |
| 2017/0306320 A1 | 10/2017 | Jewett |
| 2017/0349928 A1 | 12/2017 | Jewett |
| 2018/0016612 A1 | 1/2018 | Jewett |
| 2018/0016614 A1 | 1/2018 | Jewett |
| 2018/0298416 A1 | 10/2018 | Jewett |
| 2019/0284600 A1 | 9/2019 | Jewett |
| 2020/0063122 A1 | 2/2020 | Jewett |
| 2020/0270665 A1 | 8/2020 | Jewett |
| 2020/0291445 A1 | 9/2020 | Jewett |
| 2021/0139940 A1 | 5/2021 | Jewett |
| 2021/0147894 A1 | 5/2021 | Jewett |
| 2021/0163947 A1 | 6/2021 | Silverman |
| 2021/0163969 A1 | 6/2021 | Jewett |
| 2021/0164059 A1 | 6/2021 | Jewett |
| 2021/0171584 A1 | 6/2021 | Jewett |

FOREIGN PATENT DOCUMENTS

| | | | |
|---|---|---|---|
| JP | 2008193911 A | * | 8/2008 |
| JP | 2013071904 A | | 4/2013 |
| JP | 2017216961 A | | 12/2017 |
| JP | 2018509172 A | | 4/2018 |
| WO | 2008059823 A1 | | 5/2008 |
| WO | 2012026566 A1 | | 3/2012 |
| WO | 2015184283 A1 | | 12/2015 |
| WO | 2016199801 A1 | | 12/2016 |

OTHER PUBLICATIONS

Amiram, M. et al. Evolution of translation machinery in recoded bacteria enables multi-site incorporation of nonstandard amino acids. Nat Biotechnol 33, 1272-1279 (2015).

Chin, J.W. Expanding and reprogramming the genetic code of cells and animals. Annu Rev Biochem 83, 379-408 (2014).

Chin, J.W. Expanding and reprogramming the genetic code. Nature 550, 53-60 (2017).

Cropp, T.A., et al. Reprogramming the amino-acid substrate specificity of orthogonal aminoacyl-tRNA synthetases to expand the genetic code of eukaryotic cells. Nature Protocols 2, 2590-2600 (2007).

D'aquino, A.E., et al. Engineered ribosomes for basic science and synthetic biology. Annu Rev Chem Biomol Eng 9, 311-340 (2018).

Fujino, T., et al. Ribosomal synthesis of peptides with multiple beta-amino acids. J Am Chem Soc 138, 1962-1969 (2016).

Goto, Y. et al. Flexizymes for genetic code reprogramming. Nat Protoc 6, 779-790 (2011).

Goto, Y. et al. Initiating translation with D-amino acids. RNA 14, 1390-1398 (2008).

Goto, Y. et al. Reprogramming the translation initiation for the synthesis of physiologically stable cyclic peptides. ACS Chem Biol 3, 120-129 (2008).

Goto, Y. et al. Translation initiation with initiator tRNA charged with exotic peptides. J Am Chem Soc 131, 5040-5041 (2009).

Hancock, S.M., et al. Expanding the genetic code of yeast for incorporation of diverse unnatural amino acids via a pyrrolysyl-tRNA synthetase/tRNA pair. J Am Chem Soc 132, 14819-14824 (2010).

International Searching Authority. International Search Report and Written Opinion for application PCT/US2019/035215. dated Mar. 12, 2020. 9 pages.

Jaroentomeechai, T. et al. Single-pot glycoprotein biosynthesis using a cell-free transcription-translation system enriched with glycosylation machinery. Nat Commun 9 (2018).

Katoh, T., et al. Consecutive elongation of D-amino acids in translation. Cell Chem Biol 24, 46-54 (2017).

Kawakami, T., et al. Extensive reprogramming of the genetic code for genetically encoded synthesis of highly N-alkylated polycyclic peptidomimetics. J Am Chem Soc 135, 12297-12304 (2013).

Liu, Y., et al. Repurposing ribosomes for synthetic biology. Curr Opin Chem Biol 40, 87-94 (2017).

Mukai, T., et al. Rewriting the genetic code. Annu Rev Microbiol 71, 557-577 (2017).

Ohshiro, Y. et al. Ribosomal synthesis of backbone-macrocyclic peptides containing gamma-amino acids. ChemBioChem 12, 1183-1187 (2011).

Ohta, A., et al. Polymerization of alpha-hydroxy acids by ribosomes. ChemBioChem 9, 2773-2778 (2008).

Ohta, A., et al. Synthesis of polyester by means of genetic code reprogramming. Chem Biol 14, 1315-1322 (2007).

Passioura, T. et al. Flexizyme-mediated genetic reprogramming as a tool for noncanonical peptide synthesis and drug discovery. Chemistry 19, 6530-6536 (2013).

Rogers, J.M. et al. Discovering functional, non-proteinogenic amino acid containing, peptides using genetic code reprogramming. Org Biomol Chem 13, 9353-9363 (2015).

Schmied, W.H., et al. Efficient multisite unnatural amino acid incorporation in mammalian cells via optimized pyrrolysyl tRNA synthetase/tRNA expression and engineered eRF1. J Am Chem Soc 136, 15577-15583 (2014).

Tajima, K., et al. Genetic code expansion via integration of redundant amino acid assignment by finely tuning tRNA pools. Curr Opin Chem Biol 46, 212-218 (2018).

Terasaka, N., et al. Recent developments of engineered translational machineries for the incorporation of non-canonical amino acids into polypeptides. Int J Mol Sci 16, 6513-6531 (2015).

Vargas-Rodriguez, O., et al. Upgrading aminoacyltRNA synthetases for genetic code expansion. Curr Opin Chem Biol 46, 115-122 (2018).

Voller, J.S. et al. Coupling genetic code expansion and metabolic engineering for synthetic cells. Curr Opin Biotech 48, 1-7 (2017).

Willis, J.C.W. et al. Mutually orthogonal pyrrolysyl-tRNA synthetase/tRNA pairs. Nat Chem 10, 831-837 (2018).

Zhang, J. et al. "A flexible, scalable method for preparation of homogeneous aminoacylated tRNAs." Methods in enzymology 549 (2014): 105-113.

\* cited by examiner

EXPANDING THE CHEMICAL SUBSTRATES FOR GENETIC CODE REPROGRAMMING

CROSS-REFERENCE TO RELATED PATENT APPLICATIONS

The present application represents the U.S. national stage entry of International Application PCT/US2019/035215, filed Jun. 3, 2019, which claims the benefit of priority to U.S. Provisional Patent Application No. 62/679,350, filed Jun. 1, 2018, the content of which is incorporated herein by reference in their entireties.

STATEMENT REGARDING FEDERALLY SPONSORED RESEARCH OR DEVELOPMENT

This invention was made with government support under W911NF-16-1-0372 awarded by the Army Research Office. The government has certain rights in the invention.

BACKGROUND

The field of the invention relates to components and methods for preparing sequence defined polymers. In particular, the field of the inventions related to components and methods for use in genetic code reprogramming and flexizyme-catalyzed acylation reactions.

The site-specific incorporation of non-canonical amino acids into polypeptides through genetic code reprogramming is a powerful approach for making bio-based products that extend beyond natural limits. While a diverse repertoire of chemical substrates can be used in ribosome-mediated polymerization, flexizyme (Fx)-mediated tRNA-charging and incorporation of amino acid analogues with long-carbon chains and cyclic structures into sequence based polymers using a genetic code reprogramming approach have remained inaccessible.

Here, we demonstrate preparation and in vitro site-specific incorporation of novel substrates into sequence based polymers using a wild type and an engineered ribosome. To achieve this goal, we synthesized new substrates based on 2 scaffolds (long carbon chain and cyclic amino acids) and found that most could be acylated onto tRNA under optimized reaction conditions. Of these acylated substrates, all could be incorporated into ribosomal peptides at the N-terminus with the wildtype ribosome using in vitro translation. Notably, some cyclic amino acids could be incorporated at the C-terminus using an engineered ribosome. Our work expands the range of chemical substrates and demonstrates that such substrates can be incorporated into a peptide with an engineered translation apparatus in vitro.

SUMMARY

Disclosed are methods, systems, components, and compositions for synthesis of sequence defined polymers. The methods, systems, components, and compositions may be utilized for incorporating novel substrates that include non-standard amino acid monomers and non-amino acid monomers into sequence defined polymers. As disclosed herein, the novel substrates may be utilized for acylation of tRNA via flexizyme catalyzed reactions. The tRNAs thus acylated with the novel substrates may be utilized in synthesis platforms for incorporating the novel substrates into a sequence defined polymer.

The components disclosed herein include acylated tRNA molecules and donor molecules for preparing acylated tRNA molecules where the acylated tRNA molecules and the donor molecules comprise a monomer that may be incorporated into a sequence defined polymer. The disclosed acylated tRNA molecules are acylated with a moiety that is present in the donor molecules and may be referred to herein as "R".

The disclosed acylated tRNA molecules may be defined as having a formula:

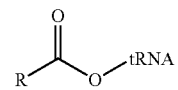

wherein:
tRNA is a transfer RNA; and
R is selected from alkyl optionally substituted with amino; heterocycloalkyl; (heterocycloalkyl)alkyl; alkenyl; cyanoalkyl; aminoalkyl; aminoalkenyl; alkylcarboxyalkylester; haloalkyl; nitroalkyl; aryl, aryl(alkyl), or (aryl)alkenyl, wherein the aryl or the aryl of the aryl(alkyl) or (aryl)alkenyl is optionally substituted with one or more substituents selected from hydroxyl, hydroxylalkyl, amino, aminoalkyl, azido, cyano, acetyl, nitro, nitroalkyl, halo, alkoxy, and alkynyl.

The disclosed acylated tRNA molecules may be prepared by reacting a tRNA molecule and a donor molecule in the presence of a flexizyme (Fx). The methods may comprise reacting in a reaction mixture: (i) a flexizyme (Fx): (ii) the tRNA molecule; and (ii) a donor molecule having a formula:

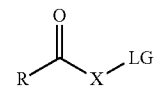

wherein:
R is a moiety as defined above;
LG is a leaving group; and
X is O or S.
In the preparation method, Fx catalyzes an acylation reaction between the tRNA molecule and the donor molecule to prepare the acylated tRNA molecule.

The disclosed methods, systems, components, and composition may be utilized for preparing sequence defined polymers in vitro and/or in vivo. In some embodiments, the disclosed methods may be performed to prepare a sequence defined polymer in a cell free synthesis system, where the sequence defined polymer is prepared via translating an mRNA comprising a codon corresponding to an anticodon of the acylated tRNA molecule. In the disclosed methods, the R group of the acylated tRNA molecule is incorporated in the sequence defined polymer during translation of the mRNA. The disclosed methods may be performed in order to prepare polymers selected from, but not limited to, polyolefin polymers, aramid polymers, polyurethane polymers, polyketide polymers, conjugated polymers, D-amino acid polymers, β-amino acid polymers, γ-amino acid polymers, and polycarbonate polymers.

DETAILED DESCRIPTION

Figure 1:
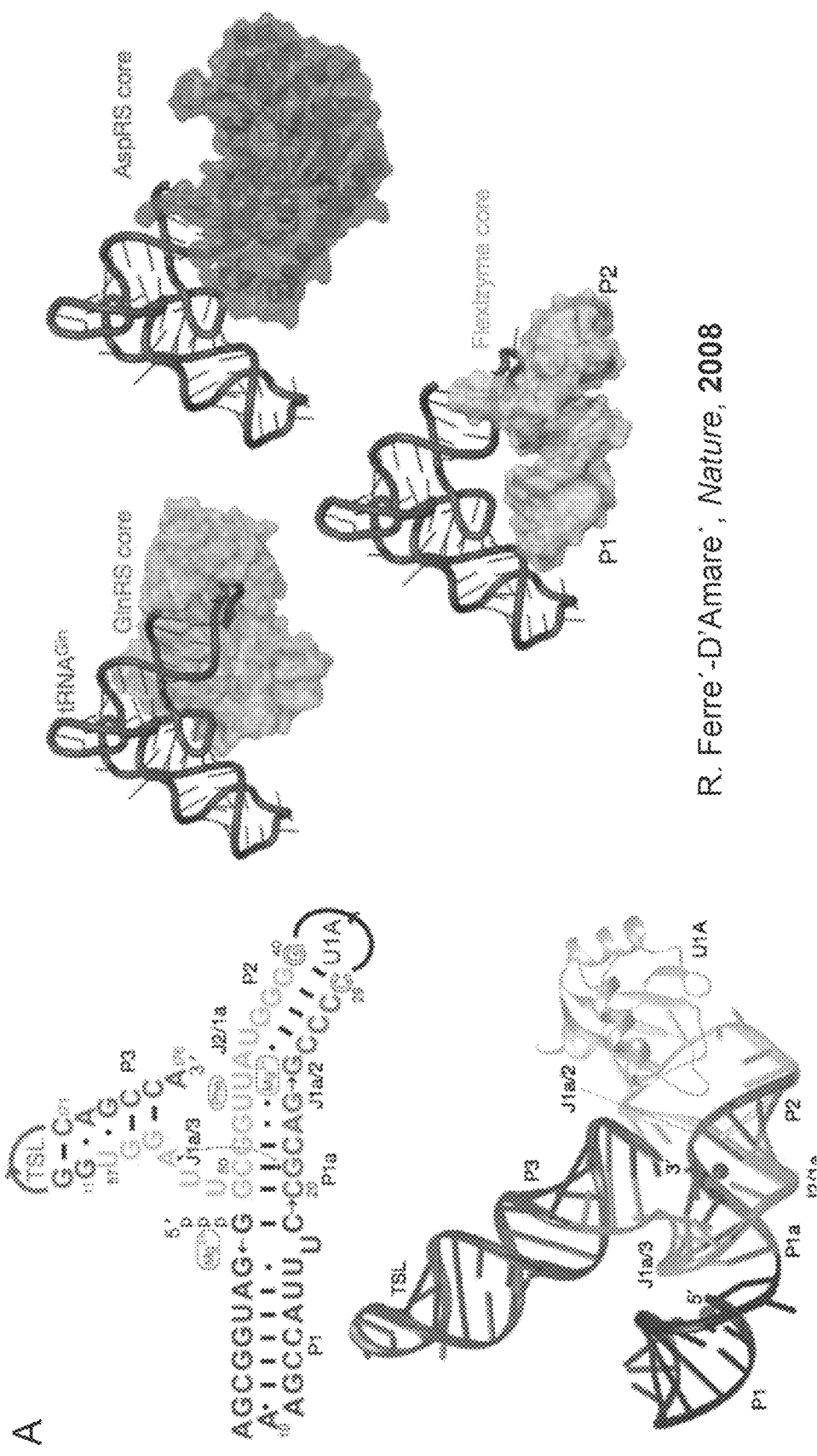
FIG. 1. A) Crystal structure of flexizyme (SEQ ID NO:22). (From Xiao, H., Murakami, H., Suga, H. & Ferre-D'Amare, A. R. Structural basis of specific tRNA aminoacylation by a small in vitro selected ribozyme. *Nature* 454, 358-361 (2008)). B) Acylation of tRNA by flexizyme and the leaving groups commonly used for preparing activated ester substrates.
Figure 1:
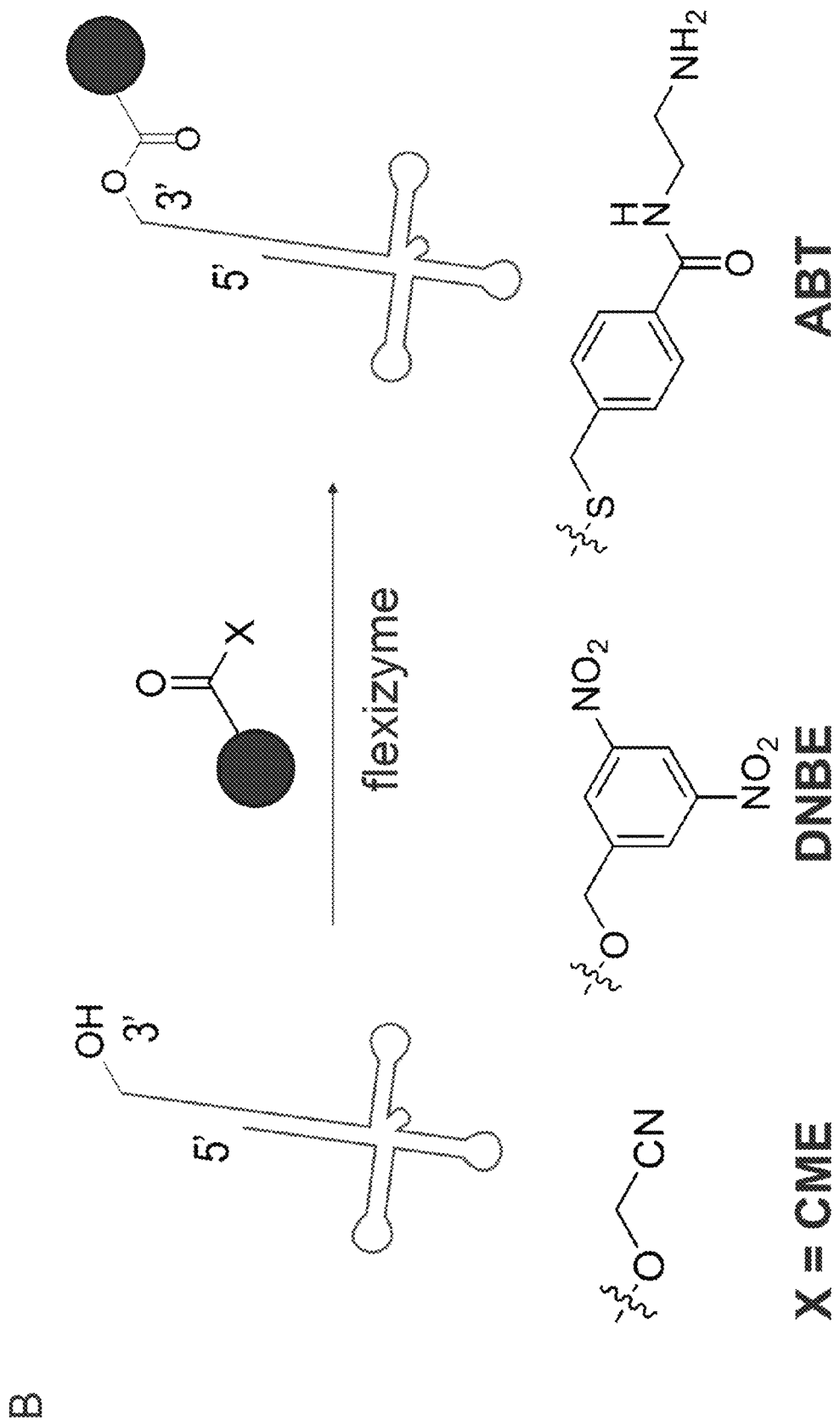

The presently disclosed subject matter is described herein using several definitions, as set forth below and throughout the application.

Definitions

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

Unless otherwise specified or indicated by context, the terms "a", "an", and "the" mean "one or more." For example, "a component" should be interpreted to mean "one or more components."

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

Ranges recited herein include the defined boundary numerical values as well as sub-ranges encompassing any non-recited numerical values within the recited range. For example, a range from about 0.01 mM to about 10.0 mM includes both 0.01 mM and 10.0 mM. Non-recited numerical values within this exemplary recited range also contemplated include, for example, 0.05 mM, 0.10 mM, 0.20 mM, 0.51 mM, 1.0 mM, 1.75 mM, 2.5 mM 5.0 mM, 6.0 mM, 7.5 mM, 8.0 mM, 9.0 mM, and 9.9 mM, among others. Exemplary sub-ranges within this exemplary recited range include from about 0.01 mM to about 5.0 mM; from about 0.1 mM to about 2.5 mM; and from about 2.0 mM to about 6.0 mM, among others.

Chemical Entities

New chemical entities and uses for chemical entities are disclosed herein. The chemical entities may be described using terminology known in the art and further discussed below.

As used herein, an asterisk "*" or a plus sign "+" may be used to designate the point of attachment for any radical group or substituent group.

The term "alkyl" as contemplated herein includes a straight-chain or branched alkyl radical in all of its isomeric forms, such as a straight or branched group of 1-12, 1-10, or 1-6 carbon atoms, referred to herein as C1-C12 alkyl, C1-C10-alkyl, and C1-C6-alkyl, respectively.

The term "alkylene" refers to a diradical of straight-chain or branched alkyl group (i.e., a diradical of straight-chain or branched C1-C6 alkyl group). Exemplary alkylene groups include, but are not limited to —CH$_2$—, —CH$_2$CH$_2$—, —CH$_2$CH$_2$CH$_2$—, —CH(CH$_3$)CH$_2$—, —CH$_2$CH(CH$_3$)CH$_2$—, —CH(CH$_2$CH$_3$)CH$_2$—, and the like.

The term "haloalkyl" refers to an alkyl group that is substituted with at least one halogen. For example, —CH$_2$F, —CHF$_2$, —CF$_3$, —CH$_2$CF$_3$, —CF$_2$CF$_3$, and the like.

The term "heteroalkyl" as used herein refers to an "alkyl" group in which at least one carbon atom has been replaced with a heteroatom (e.g., an O, N, or S atom). One type of heteroalkyl group is an "alkoxy" group.

The term "alkenyl" as used herein refers to an unsaturated straight or branched hydrocarbon having at least one carbon-carbon double bond, such as a straight or branched group of 2-12, 2-10, or 2-6 carbon atoms, referred to herein as C2-C12-alkenyl, C2-C10-alkenyl, and C2-C6-alkenyl, respectively.

The term "alkynyl" as used herein refers to an unsaturated straight or branched hydrocarbon having at least one carbon-carbon triple bond, such as a straight or branched group of 2-12, 2-10, or 2-6 carbon atoms, referred to herein as C2-C12-alkynyl, C2-C10-alkynyl, and C2-C6-alkynyl, respectively.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "C4-8-cycloalkyl," derived from a cycloalkane. Unless specified otherwise, cycloalkyl groups are optionally substituted at one or more ring positions with, for example, alkanoyl, alkoxy, alkyl, haloalkyl, alkenyl, alkynyl, amido or carboxyamido, amidino, amino, aryl, arylalkyl, azido, carbamate, carbonate, carboxy, cyano, cycloalkyl, ester, ether, formyl, halo, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the cycloalkyl group is not substituted, i.e., it is unsubstituted.

The term "cycloheteroalkyl" refers to a monovalent saturated cyclic, bicyclic, or bridged cyclic hydrocarbon group of 3-12, 3-8, 4-8, or 4-6 carbons in which at least one carbon of the cycloalkane is replaced with a heteroatom such as, for example, N, O, and/or S.

The term "cycloalkylene" refers to a cycloalkyl group that is unsaturated at one or more ring bonds.

The term "partially unsaturated carbocyclyl" refers to a monovalent cyclic hydrocarbon that contains at least one double bond between ring atoms where at least one ring of the carbocyclyl is not aromatic. The partially unsaturated carbocyclyl may be characterized according to the number oring carbon atoms. For example, the partially unsaturated carbocyclyl may contain 5-14, 5-12, 5-8, or 5-6 ring carbon atoms, and accordingly be referred to as a 5-14, 5-12, 5-8, or 5-6 membered partially unsaturated carbocyclyl, respectively. The partially unsaturated carbocyclyl may be in the form of a monocyclic carbocycle, bicyclic carbocycle, tricyclic carbocycle, bridged carbocycle, spirocyclic carbocycle, or other carbocyclic ring system. Exemplary partially unsaturated carbocyclyl groups include cycloalkenyl groups and bicyclic carbocyclyl groups that are partially unsaturated. Unless specified otherwise, partially unsaturated carbocyclyl groups are optionally substituted at one or more ring positions with, for example, alkanoyl, alkoxy, alkyl, haloalkyl, alkenyl, alkynyl, amido or carboxyamido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the partially unsaturated carbocyclyl is not substituted, i.e., it is unsubstituted.

The term "aryl" is art-recognized and refers to a carbocyclic aromatic group. Representative aryl groups include phenyl, naphthyl, anthracenyl, and the like. The term "aryl" includes polycyclic ring systems having two or more carbocyclic rings in which two or more carbons are common to two adjoining rings (the rings are "fused rings") wherein at least one of the rings is aromatic and, e.g., the other ring(s) may be cycloalkyls, cycloalkenyls, cycloalkynyls, and/or aryls. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido or carboxyamido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. In certain embodiments, the aromatic ring is substituted at one or more ring positions with halogen, alkyl, hydroxyl, or alkoxyl. In certain other embodiments, the aromatic ring is not substituted, i.e., it is unsubstituted. In certain embodiments, the aryl group is a 6-10 membered ring structure.

The terms "heterocyclyl" and "heterocyclic group" are art-recognized and refer to saturated, partially unsaturated, or aromatic 3- to 10-membered ring structures, alternatively 3- to 7-membered rings, whose ring structures include one to four heteroatoms, such as nitrogen, oxygen, and sulfur. The number of ring atoms in the heterocyclyl group can be specified using 5 Cx-Cx nomenclature where x is an integer specifying the number of ring atoms. For example, a C3-C7 heterocyclyl group refers to a saturated or partially unsaturated 3- to 7-membered ring structure containing one to four heteroatoms, such as nitrogen, oxygen, and sulfur. The designation "C3-C7" indicates that the heterocyclic ring contains a total of from 3 to 7 ring atoms, inclusive of any heteroatoms that occupy a ring atom position.

The terms "amine" and "amino" are art-recognized and refer to both unsubstituted and substituted amines (e.g., mono-substituted amines or di-substituted amines), wherein substituents may include, for example, alkyl, cycloalkyl, heterocyclyl, alkenyl, and aryl.

The terms "alkoxy" or "alkoxyl" are art-recognized and refer to an alkyl group, as defined above, having an oxygen radical attached thereto. Representative alkoxy groups include methoxy, ethoxy, tert-butoxy and the like.

An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, and the like.

The term "carbonyl" as used herein refers to the radical —C(O)—.

The term "oxo" refers to a divalent oxygen atom —O—.

The term "carboxamido" as used herein refers to the radical —C(O)NRR', where R and R' may be the same or different. R and R', for example, may be independently hydrogen, alkyl, aryl, arylalkyl, cycloalkyl, formyl, haloalkyl, heteroaryl, or heterocyclyl.

The term "carboxy" as used herein refers to the radical —COOH or its corresponding salts, e.g. —COONa, etc.

The term "amide" or "amido" or "amidyl" as used herein refers to a radical of the form —R$^1$C(O)N(R$^2$)—, —R$^1$C(O)N(R$^2$)R$^3$—, —C(O)NR$^2$R$^3$, or —C(O)NH$_2$, wherein R$^1$, R$^2$ and R$^3$, for example, are each independently hydrogen, alkyl, alkoxy, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," or "+" or "−" depending on the configuration of substituents around the stereogenic carbon atom and or the optical rotation observed. The present invention encompasses various stereo isomers of these compounds and mixtures thereof. Stereoisomers include enantiomers and diastereomers. Mixtures of enantiomers or diastereomers may be designated (±)" in nomenclature, but the skilled artisan will recognize that a structure may denote a chiral center implicitly. It is understood that graphical depictions of chemical structures, e.g., generic chemical structures, encompass all stereoisomeric forms of the specified compounds, unless indicated otherwise. Also contemplated herein are compositions comprising, consisting essentially of, or consisting of an enantiopure compound, which composition may comprise, consist essential of, or consist of at least about 50%, 60%, 70%, 80%, 90%, 95%, 96%, 97%, 98%, 99%, or 100% of a single enantiomer of a given compound (e.g., at least about 99% of an R enantiomer of a given compound).

Nucleic Acids and Reactions

The terms "nucleic acid" and "oligonucleotide," as used herein, refer to polydeoxyribonucleotides (containing 2-deoxy-D-ribose), polyribonucleotides (containing D-ribose), and to any other type of polynucleotide that is an N glycoside of a purine or pyrimidine base. There is no intended distinction in length between the terms "nucleic acid", "oligonucleotide" and "polynucleotide", and these terms will be used interchangeably. These terms refer only to the primary structure of the molecule. Thus, these terms include double- and single-stranded DNA, as well as double- and single-stranded RNA. For use in the present invention, an oligonucleotide also can comprise nucleotide analogs in which the base, sugar, or phosphate backbone is modified as well as non-purine or non-pyrimidine nucleotide analogs.

Oligonucleotides can be prepared by any suitable method, including direct chemical synthesis by a method such as the phosphotriester method of Narang et al., 1979, Meth. Enzymol. 68:90-99; the phosphodiester method of Brown et al., 1979, Meth. Enzymol. 68:109-151; the diethylphosphoramidite method of Beaucage et al., 1981, Tetrahedron Letters 22:1859-1862; and the solid support method of U.S. Pat. No. 4,458,066, each incorporated herein by reference. A review of synthesis methods of conjugates of oligonucleotides and modified nucleotides is provided in Goodchild, 1990, Bioconjugate Chemistry 1(3): 165-187, incorporated herein by reference.

The term "amplification reaction" refers to any chemical reaction, including an enzymatic reaction, which results in increased copies of a template nucleic acid sequence or results in transcription of a template nucleic acid. Amplification reactions include reverse transcription, the polymerase chain reaction (PCR), including Real Time PCR (see U.S. Pat. Nos. 4,683,195 and 4,683,202; PCR Protocols: A Guide to Methods and Applications (Innis et al., eds, 1990)), and the ligase chain reaction (LCR) (see Barany et al., U.S. Pat. No. 5,494,810). Exemplary "amplification reactions conditions" or "amplification conditions" typically comprise either two or three step cycles. Two-step cycles have a high temperature denaturation step followed by a hybridization/elongation (or ligation) step. Three step cycles comprise a denaturation step followed by a hybridization step followed by a separate elongation step.

The terms "target, "target sequence", "target region", and "target nucleic acid," as used herein, are synonymous and refer to a region or sequence of a nucleic acid which is to be amplified, sequenced, or detected.

The term "hybridization," as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which hybridization of fully complementary nucleic acid strands is strongly preferred are referred to as "stringent hybridization conditions" or "sequence-specific hybridization conditions". Stable duplexes of substantially complementary sequences can be achieved under less stringent hybridization conditions; the degree of mismatch tolerated can be controlled by suitable adjustment of the hybridization conditions. Those skilled in the art of nucleic acid technology can determine duplex stability empirically considering a number of variables including, for example, the length and base pair composition of the oligonucleotides, ionic strength, and incidence of mismatched base pairs, following the guidance provided by the art (see, e.g., Sambrook et al., 1989, Molecular Cloning—A Laboratory Manual, Cold Spring Harbor Laboratory, Cold Spring Harbor, N.Y.; Wetmur, 1991, Critical Review in Biochem. and Mol. Biol. 26(3/4):227-259; and Owczarzy et al., 2008, Biochemistry, 47: 5336-5353, which are incorporated herein by reference).

The term "primer," as used herein, refers to an oligonucleotide capable of acting as a point of initiation of DNA synthesis under suitable conditions. Such conditions include those in which synthesis of a primer extension product complementary to a nucleic acid strand is induced in the presence of four different nucleoside triphosphates and an agent for extension (for example, a DNA polymerase or reverse transcriptase) in an appropriate buffer and at a suitable temperature.

A primer is preferably a single-stranded DNA. The appropriate length of a primer depends on the intended use of the primer but typically ranges from about 6 to about 225 nucleotides, including intermediate ranges, such as from 15 to 35 nucleotides, from 18 to 75 nucleotides and from 25 to 150 nucleotides. Short primer molecules generally require cooler temperatures to form sufficiently stable hybrid complexes with the template. A primer need not reflect the exact sequence of the template nucleic acid, but must be sufficiently complementary to hybridize with the template. The design of suitable primers for the amplification of a given target sequence is well known in the art and described in the literature cited herein.

Primers can incorporate additional features which allow for the detection or immobilization of the primer but do not alter the basic property of the primer, that of acting as a point of initiation of DNA synthesis. For example, primers may contain an additional nucleic acid sequence at the 5' end which does not hybridize to the target nucleic acid, but which facilitates cloning or detection of the amplified product, or which enables transcription of RNA (for example, by inclusion of a promoter) or translation of protein (for example, by inclusion of a 5'-UTR, such as an Internal Ribosome Entry Site (IRES) or a 3'-UTR element, such as a poly$(A)_n$ sequence, where n is in the range from about 20 to about 200). The region of the primer that is sufficiently complementary to the template to hybridize is referred to herein as the hybridizing region.

As used herein, a primer is "specific," for a target sequence if, when used in an amplification reaction under sufficiently stringent conditions, the primer hybridizes primarily to the target nucleic acid. Typically, a primer is specific for a target sequence if the primer-target duplex stability is greater than the stability of a duplex formed between the primer and any other sequence found in the sample. One of skill in the art will recognize that various factors, such as salt conditions as well as base composition of the primer and the location of the mismatches, will affect the specificity of the primer, and that routine experimental confirmation of the primer specificity will be needed in many cases. Hybridization conditions can be chosen under which the primer can form stable duplexes only with a target sequence. Thus, the use of target-specific primers under suitably stringent amplification conditions enables the selective amplification of those target sequences that contain the target primer binding sites.

As used herein, a "polymerase" refers to an enzyme that catalyzes the polymerization of nucleotides. "DNA polymerase" catalyzes the polymerization of deoxyribonucleotides. Known DNA polymerases include, for example, *Pyrococcus furiosus* (Pfu) DNA polymerase, *E. coli* DNA polymerase I, T7 DNA polymerase and *Thermus aquaticus* (Taq) DNA polymerase, among others. "RNA polymerase" catalyzes the polymerization of ribonucleotides. The foregoing examples of DNA polymerases are also known as DNA-dependent DNA polymerases. RNA-dependent DNA polymerases also fall within the scope of DNA polymerases. Reverse transcriptase, which includes viral polymerases encoded by retroviruses, is an example of an RNA-dependent DNA polymerase. Known examples of RNA polymerase ("RNAP") include, for example, bacteriophage polymerases such as, but not limited to, T3 RNA polymerase, T7 RNA polymerase, SP6 RNA polymerase and *E. coli* RNA polymerase, among others. The foregoing examples of RNA polymerases are also known as DNA-dependent RNA polymerase. The polymerase activity of any of the above enzymes can be determined by means well known in the art.

The term "promoter" refers to a cis-acting DNA sequence that directs RNA polymerase and other trans-acting transcription factors to initiate RNA transcription from the DNA template that includes the cis-acting DNA sequence.

As used herein, the term "sequence defined biopolymer" refers to a biopolymer having a specific primary sequence.

A sequence defined biopolymer can be equivalent to a genetically-encoded defined biopolymer in cases where a gene encodes the biopolymer having a specific primary sequence.

As used herein, "expression template" refers to a nucleic acid that serves as substrate for transcribing at least one RNA that can be translated into a sequence defined biopolymer (e.g., a polypeptide or protein). Expression templates include nucleic acids composed of DNA or RNA. Suitable sources of DNA for use a nucleic acid for an expression template include genomic DNA, cDNA and RNA that can be converted into cDNA. Genomic DNA, cDNA and RNA can be from any biological source, such as a tissue sample, a biopsy, a swab, sputum, a blood sample, a fecal sample, a urine sample, a scraping, among others. The genomic DNA, cDNA and RNA can be from host cell or virus origins and from any species, including extant and extinct organisms. As used herein, "expression template" and "transcription template" have the same meaning and are used interchangeably.

As used herein, "translation template" refers to an RNA product of transcription from an expression template that can be used by ribosomes to synthesize polypeptide or protein.

As used herein, coupled transcription/translation ("Tx/Tl"), refers to the de novo synthesis of both RNA and a sequence defined biopolymer from the same extract. For example, coupled transcription/translation of a given sequence defined biopolymer can arise in an extract containing an expression template and a polymerase capable of generating a translation template from the expression template. Coupled transcription/translation can occur using a cognate expression template and polymerase from the organism used to prepare the extract. Coupled transcription/translation can also occur using exogenously-supplied expression template and polymerase from an orthogonal host organism different from the organism used to prepare the extract. In the case of an extract prepared from a yeast organism, an example of an exogenously-supplied expression template includes a translational open reading frame operably coupled a bacteriophage polymerase-specific promoter and an example of the polymerase from an orthogonal host organism includes the corresponding bacteriophage polymerase.

The term "reaction mixture," as used herein, refers to a solution containing reagents necessary to carry out a given reaction. An "amplification reaction mixture", which refers to a solution containing reagents necessary to carry out an amplification reaction, typically contains oligonucleotide primers and a DNA polymerase in a suitable buffer. A "PCR reaction mixture" typically contains oligonucleotide primers, a DNA polymerase (most typically a thermostable DNA polymerase), dNTPs, and a divalent metal cation in a suitable buffer.

Cell-Free Protein Synthesis (CFPS)

The disclosed subject matter relates in part to methods, systems, components, and compositions for cell-free protein synthesis. Cell-free protein synthesis (CFPS) is known and has been described in the art. (See, e.g., U.S. Pat. Nos. 6,548,276; 7,186,525; 8,734,856; 7,235,382; 7,273,615; 7,008,651; 6,994,986 7,312,049; 7,776,535; 7,817,794; 8,298,759; 8,715,958; 9,005,920; U.S. Publication No. 2014/0349353, and U.S. Publication No. 2016/0060301, the contents of which are incorporated herein by reference in their entireties). A "CFPS reaction mixture" typically contains a crude or partially-purified yeast extract, an RNA translation template, and a suitable reaction buffer for promoting cell-free protein synthesis from the RNA translation template. In some aspects, the CFPS reaction mixture can include exogenous RNA translation template. In other aspects, the CFPS reaction mixture can include a DNA expression template encoding an open reading frame operably linked to a promoter element for a DNA-dependent RNA polymerase. In these other aspects, the CFPS reaction mixture can also include a DNA-dependent RNA polymerase to direct transcription of an RNA translation template encoding the open reading frame. In these other aspects, additional NTP's and divalent cation cofactor can be included in the CFPS reaction mixture. A reaction mixture is referred to as complete if it contains all reagents necessary to enable the reaction, and incomplete if it contains only a subset of the necessary reagents. It will be understood by one of ordinary skill in the art that reaction components are routinely stored as separate solutions, each containing a subset of the total components, for reasons of convenience, storage stability, or to allow for application-dependent adjustment of the component concentrations, and that reaction components are combined prior to the reaction to create a complete reaction mixture. Furthermore, it will be understood by one of ordinary skill in the art that reaction components are packaged separately for commercialization and that useful commercial kits may contain any subset of the reaction components of the invention.

Platforms for Preparing Sequence Defined Biopolymers

An aspect of the invention is a platform for preparing a sequence defined biopolymer of protein in vitro. The platform for preparing a sequence defined polymer or protein in vitro comprises a cellular extract from the GRO organism as described above. Because CFPS exploits an ensemble of catalytic proteins prepared from the crude lysate of cells, the cell extract (whose composition is sensitive to growth media, lysis method, and processing conditions) is the most critical component of extract-based CFPS reactions. A variety of methods exist for preparing an extract competent for cell-free protein synthesis, including U.S. patent application Ser. No. 14/213,390 to Michael C. Jewett et al., entitled METHODS FOR CELL-FREE PROTEIN SYNTHESIS, filed Mar. 14, 2014, and now published as U.S. Patent Application Publication No. 2014/0295492 on Oct. 2, 2014, and U.S. patent application Ser. No. 14/840,249 to Michael C. Jewett et al., entitled METHODS FOR IMPROVED IN VITRO PROTEIN SYNTHESIS WITH PROTEINS CONTAINING NON STANDARD AMINO ACIDS, filed Aug. 31, 2015, and now published as U.S. Patent Application Publication No. 2016/0060301, on Mar. 3, 2016, the contents of which are incorporated by reference.

The platform may comprise an expression template, a translation template, or both an expression template and a translation template. The expression template serves as a substrate for transcribing at least one RNA that can be translated into a sequence defined biopolymer (e.g., a polypeptide or protein). The translation template is an RNA product that can be used by ribosomes to synthesize the sequence defined biopolymer. In certain embodiments the platform comprises both the expression template and the translation template. In certain specific embodiments, the platform may be a coupled transcription/translation ("Tx/Tl") system where synthesis of translation template and a sequence defined biopolymer from the same cellular extract.

The platform may comprise one or more polymerases capable of generating a translation template from an expression template. The polymerase may be supplied exogenously or may be supplied from the organism used to prepare the extract. In certain specific embodiments, the polymerase is expressed from a plasmid present in the organism used to prepare the extract and/or an integration site in the genome of the organism used to prepare the extract.

The platform may comprise an orthogonal translation system. An orthogonal translation system may comprise one or more orthogonal components that are designed to operate parallel to and/or independent of the organism's orthogonal translation machinery. In certain embodiments, the orthogonal translation system and/or orthogonal components are configured to incorporation of unnatural amino acids. An orthogonal component may be an orthogonal protein or an orthogonal RNA. In certain embodiments, an orthogonal protein may be an orthogonal synthetase. In certain embodiments, the orthogonal RNA may be an orthogonal tRNA or an orthogonal rRNA. An example of an orthogonal rRNA component has been described in Application No. PCT/US2015/033221 to Michael C. Jewett et al., entitled TETHERED RIBOSOMES AND METHODS OF MAKING AND USING THEREOF, filed 29 May 2015, and now published as WO2015184283, and U.S. patent application Ser. No. 15/363,828, to Michael C. Jewett et al., entitled RIBOSOMES WITH TETHERED SUBUNITS, filed on Nov. 29, 2016, and now published as U.S. Patent Application Publication No. 2017/0073381, on Mar. 16, 2017, the contents of which are incorporated by reference. In certain embodiments, one or more orthogonal components may be prepare in vivo or in vitro by the expression of an oligonucleotide template. The one or more orthogonal components may be expressed from a plasmid present in the genomically recoded organism, expressed from an integration site in the genome of the genetically recoded organism, co-expressed from both a plasmid present in the genomically recoded organism and an integration site in the genome of the genetically recoded organism, express in the in vitro transcription and translation reaction, or added exogenously as a factor (e.g., a orthogonal tRNA or an orthogonal synthetase added to the platform or a reaction mixture).

Altering the physicochemical environment of the CFPS reaction to better mimic the cytoplasm can improve protein synthesis activity. The following parameters can be considered alone or in combination with one or more other components to improve robust CFPS reaction platforms based upon crude cellular extracts (for examples, S12, S30 and S60 extracts).

The temperature may be any temperature suitable for CFPS. Temperature may be in the general range from about 10° C. to about 40° C., including intermediate specific ranges within this general range, include from about 15° C. to about 35° C., form about 15° C. to about 30° C., form about 15° C. to about 25° C. In certain aspects, the reaction temperature can be about 15° C., about 16° C., about 17° C., about 18° C., about 19° C., about 2° C., about 21° C., about 22° C., about 23° C., about 24° C., about 25° C.

The CFPS reaction can include any organic anion suitable for CFPS. In certain aspects, the organic anions can be glutamate, acetate, among others. In certain aspects, the concentration for the organic anions is independently in the general range from about 0 mM to about 200 mM, including intermediate specific values within this general range, such as about 0 mM, about 10 mM, about 20 mM, about 30 mM, about 40 mM, about 50 mM, about 60 mM, about 70 mM, about 80 mM, about 90 mM, about 100 mM, about 110 mM, about 120 mM, about 130 mM, about 140 mM, about 150 mM, about 160 mM, about 170 mM, about 180 mM, about 190 mM and about 200 mM, among others.

The CFPS reaction can also include any halide anion suitable for CFPS. In certain aspects the halide anion can be chloride, bromide, iodide, among others. A preferred halide anion is chloride. Generally, the concentration of halide anions, if present in the reaction, is within the general range from about 0 mM to about 200 mM, including intermediate specific values within this general range, such as those disclosed for organic anions generally herein.

The CFPS reaction may also include any organic cation suitable for CFPS. In certain aspects, the organic cation can be a polyamine, such as spermidine or putrescine, among others. Preferably polyamines are present in the CFPS reaction. In certain aspects, the concentration of organic cations in the reaction can be in the general about 0 mM to about 3 mM, about 0.5 mM to about 2.5 mM, about 1 mM to about 2 mM. In certain aspects, more than one organic cation can be present.

The CFPS reaction can include any inorganic cation suitable for CFPS. For example, suitable inorganic cations can include monovalent cations, such as sodium, potassium, lithium, among others; and divalent cations, such as magnesium, calcium, manganese, among others. In certain aspects, the inorganic cation is magnesium. In such aspects, the magnesium concentration can be within the general range from about 1 mM to about 50 mM, including intermediate specific values within this general range, such as about 1 mM, about 2 mM, about 3 mM, about 5 mM, about 6 mM, about 7 mM, about 8 mM, about 9 mM, about 10 mM, among others. In preferred aspects, the concentration of inorganic cations can be within the specific range from about 4 mM to about 9 mM and more preferably, within the range from about 5 mM to about 7 mM.

The CFPS reaction includes NTPs. In certain aspects, the reaction use ATP, GTP, CTP, and UTP. In certain aspects, the concentration of individual NTPs is within the range from about 0.1 mM to about 2 mM.

The CFPS reaction can also include any alcohol suitable for CFPS. In certain aspects, the alcohol may be a polyol, and more specifically glycerol. In certain aspects the alcohol is between the general range from about 0% (v/v) to about 25% (v/v), including specific intermediate values of about 5% (v/v), about 10% (v/v) and about 15% (v/v), and about 20% (v/v), among others.

Methods for Preparing Proteins and Sequence Defined Biopolymers

An aspect of the invention is a method for cell-free protein synthesis of a sequence defined biopolymer or protein in vitro. The method comprises contacting a RNA template encoding a sequence defined biopolymer with a reaction mixture comprising a cellular extract from a GRO as described above. Methods for cell-free protein synthesis of a sequence defined biopolymers have been described [1, 18, 26].

In certain embodiments, a sequence-defined biopolymer or protein comprises a product prepared by the method or the platform that includes an amino acids. In certain embodiments the amino acid may be a natural amino acid. As used herein a natural amino acid is a proteinogenic amino acid encoded directly by a codon of the universal genetic code. In certain embodiments the amino acid may be an unnatural amino acid. As used here an unnatural amino acid is a nonproteinogenic amino acid. An unnatural amino acids may also be referred to as a non-standard amino acid (NSAA) or non-canonical amino acid. In certain embodiments, a sequence defined biopolymer or protein may comprise a plurality of unnatural amino acids. In certain specific embodiments, a sequence defined biopolymer or protein may comprise a plurality of the same unnatural amino acid. The sequence defined biopolymer or protein may comprise at least 5, at least 10, at least 15, at least 20, at least 25, at least 30, at least 35, or at least 40 or the same or different unnatural amino acids.

Examples of unnatural, non-canonical, and/or non-standard amino acids include, but are not limited, to a p-acetyl-L-phenylalanine, a p-iodo-L-phenylalanine, an O-methyl-L-tyrosine, a p-propargyloxyphenylalanine, a p-propargyl-phenylalanine, an L-3-(2-naphthyl)alanine, a 3-methyl-phenylalanine, an O-4-allyl-L-tyrosine, a 4-propyl-L-tyrosine, a tri-O-acetyl-GcNAcpβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-bromophenyl-alanine, a p-amino-L-phenylalanine, an isopropyl-L-phenyl-alanine, an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an unnatural analogue of a methionine amino acid; an unnatural analogue of a leucine amino acid; an unnatural analogue of a isoleucine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, 24ufa24hor, phosphono, phosphine, heterocyclic, enone, imine, aldehyde, hydroxylamine, keto, or amino substituted amino acid, or a combination thereof; an amino acid with a photoactivatable cross-linker; a spin-labeled amino acid; a fluorescent amino acid; a metal binding amino acid; a metal-containing amino acid; a radio-active amino acid; a photocaged and/or photoisomerizable amino acid; a biotin or biotin-analogue containing amino acid; a keto containing amino acid; an amino acid comprising polyethylene glycol or polyether; a heavy atom substituted amino acid; a chemically cleavable or photocleavable amino acid; an amino acid with an elongated side chain; an amino acid containing a toxic group; a sugar substituted amino acid; a carbon-linked sugar-containing amino acid; a redox-active amino acid; an a-hydroxy containing acid; an amino thio acid; an α,α disubstituted amino acid; a β-amino acid; a γ-amino acid, a cyclic amino acid other than proline or histidine, and an aromatic amino acid other than phenylalanine, tyrosine or tryptophan.

The methods described herein allow for preparation of sequence defined biopolymers or proteins with high fidelity to a RNA template. In other words, the methods described herein allow for the correct incorporation of unnatural, non-canonical, and/or non-standard amino acids as encoded by an RNA template. In certain embodiments, the sequence defined biopolymer encoded by a RNA template comprises at least 5, at least 10, at least 15, at least 20, at least 25, at least 30, at least 35, or at least 40 unnatural, non-canonical, and/or non-standard amino acids and a product prepared from the method includes at least 80%, at least 85%, at least 90%, at least 95%, or 100% of the encoded unnatural, non-canonical, and/or non-standard amino acids.

The methods described herein also allow for the preparation of a plurality of products prepared by the method. In certain embodiments, at least 80%, at least 85%, at least 90%, at least 95%, or at least 98% of a plurality of products prepared by the method are full length. In certain embodiments, the sequence defined biopolymer encoded by a RNA template comprises at least 5, at least 10, at least 15, at least 20, at least 25, at least 30, at least 35, or at least 40 unnatural, non-canonical, and/or non-standard amino acids and at least 80%, at least 85%, at least 90%, at least 95%, or at least 98% of a plurality of products prepared by the method include 100% of the encoded unnatural, non-canonical, and/or non-standard amino acids.

In certain embodiments, the sequence defined biopolymer or the protein encodes a therapeutic product, a diagnostic product, a biomaterial product, an adhesive product, a biocomposite product, or an agricultural product.

Miscellaneous

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Expanding the Chemical Substrates for Genetic Code Reprogramming

The subject matter disclosed herein relates to methods, systems, components, and compositions that may be utilized to synthesize sequence defined polymers. In particular, the methods, systems, components, and compositions may be utilized for incorporating novel substrates that include non-standard amino acid monomers and non-amino acid monomers into sequence defined polymers. As disclosed herein, the novel substrates may be utilized for acylation of tRNA via flexizyme catalyzed reactions. The tRNAs thus acylated with the novel substrates may be utilized in synthesis platforms for incorporating the novel substrates into a sequence defined polymer.

The components disclosed herein include acylated tRNA molecules and donor molecules for preparing acylated tRNA molecules. The disclosed acylated tRNA molecules are acylated with a moiety that is present in the donor molecules and may be referred to herein as "R" and which may be incorporated into a polymer (e.g., a sequence defined polymer).

In some embodiments, the acylated tRNA molecules have a formula which may be defined as:

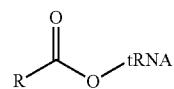

wherein:
tRNA is a transfer RNA linked via a 3' terminal ribonucleotide (e.g. via an ester bond formed with the ribose of a 3' terminal adenosine); and R may be selected from alkyl (e.g., butyl); cycloalkyl (e.g., cyclobutyl, cyclopentyl, or cyclohexyl) optionally substituted with amino; heterocycloalkyl (e.g., a cyclic secondary amine such as piperidinyl or piperazinyl); (heterocycloalkyl)alkyl (e.g., a cyclic secondary amine such as (piperidinyl)methyl or (piperazinyl)methyl); alkenyl (e.g., 1-buten-4-yl); cyanoalkyl (e.g., cyanomethyl or cyanoethyl); aminoalkyl (e.g., aminopropyl, aminobutyl, aminopentyl, 1,1-dimethyl-3-amino-propanyl, methylaminopropyl, or aminohexyl); aminoalkenyl (e.g., 1-amino-2-propenyl); alkylcarboxyalkylester (e.g., methylcarboxyethyl ester); haloalkyl (e.g., 2-bromo-propan-2-yl); nitroalkyl (e.g., nitromethyl); aryl (e.g., phenyl, pyrrolyl, thiophenyl, furanyl, pyridinyl, coumarinyl), (aryl)alkyl (e.g., benzyl, (phenyl)ethyl, or (pyrrolyl)ethyl), or (aryl)alkenyl (e.g., (phenyl) ethenyl), wherein the aryl or the aryl of the (aryl)alkyl or (aryl)alkenyl is optionally substituted with one or more substituents selected from hydroxyl (e.g., 3,4-dihydroxylphenyl), hydroxylalkyl (e.g., hydroxylmethyl), amino, aminoalkyl (e.g., aminomethyl), azido, cyano, acetyl, nitro, nitroalkyl (e.g., nitromethyl), halo, alkoxy (e.g., methoxy), and alkynyl.

In some embodiments of the acylated tRNA molecules, R is substituted alkylaryl. Optionally, R may be selected from (3,4-dihydroxyphenyl)methyl, (pyrrol-2-yl)methyl, and (4-amino-phenyl)methyl.

In some embodiments of the acylated tRNA molecules, R is substituted phenyl. Optionally, R may be selected from 4-nitrophenyl, 4-cyanophenyl, 4-azidophenyl, 3-acetylphenyl, 4-nitromethyphenyl, 2-fluorophenyl, 4-methoxyphenyl, 3-hydroxy-4-nitrophenyl, 3-amino-4-nitrophenyl, and 3-nitro-4-aminophenyl.

In some embodiments of the acylated tRNA molecules, R is heteroaryl or substituted heteroaryl. Optionally, R may be selected from pyridinyl (e.g., pyridine-4-yl), fluoropyridinyl (e.g., 3-fluoro-pyridin-3-yl), coumarinyl, pyrrolyl (e.g., pyrrol-2-yl), thiophen-2-yl, and 5-aminomethyl-furan-3-yl.

In some embodiments of the acylated tRNA molecules, R comprises a primary amine group or a secondary amine group. Optionally, R may be selected from 3-aminopropyl, 4-aminobutyl, 5-aminobutyl, 1,1-dimethyl-3-aminopropanyl, 3-methylamino-propanyl, 6-aminohexyl, 3-amino-1-propenyl, 2-aminocyclobutyl (e.g., 2(R)-aminocyclobutyl or 2(S)-aminocyclobutyl), 2-aminocyclopentyl (e.g., 2(R)-aminocyclopentyl or 2(S)-aminocyclopentyl), 2-aminocyclohexyl (e.g., 2(R)-aminocyclohexyl or 2(S)-aminocyclohexyl).

In some embodiments of the acylated tRNA molecules, R comprises a cycloalkyl group optionally substituted with amino. Optionally, R may be selected from cyclobutyl or aminocyclobutyl such as 2-aminocyclobutyl (e.g., 2(R)-aminocyclobutyl or 2(S)-aminocyclobutyl), cyclopentyl or aminocyclopentyl such as 2-aminocyclopentyl (e.g., 2(R)-aminocyclopentyl or 2(S)-aminocyclopentyl), and cyclohexyl or aminocyclohexyl such as 2-aminocyclohexyl (e.g., 2(R)-aminocyclohexyl or 2(S)-aminocyclohexyl).

In some embodiments of the acylated tRNA molecules, R comprises a cyclic secondary amine such as piperidinyl or piperazinyl. Optionally, R is selected from piperidin-4-yl, (piperidin-4-yl)methyl, piperazin-4-yl, and (piperazin-4-yl)methyl.

In some embodiments of the acylated tRNA molecules, R is selected from alkyl (e.g., butyl), alkenyl (e.g., 3-butenyl), cyanoalkyl (e.g., cyanomethyl or cyanoethyl), and alkylcarboxylalkyl ester (e.g., methylcarboxyethyl ester).

Figure 15:
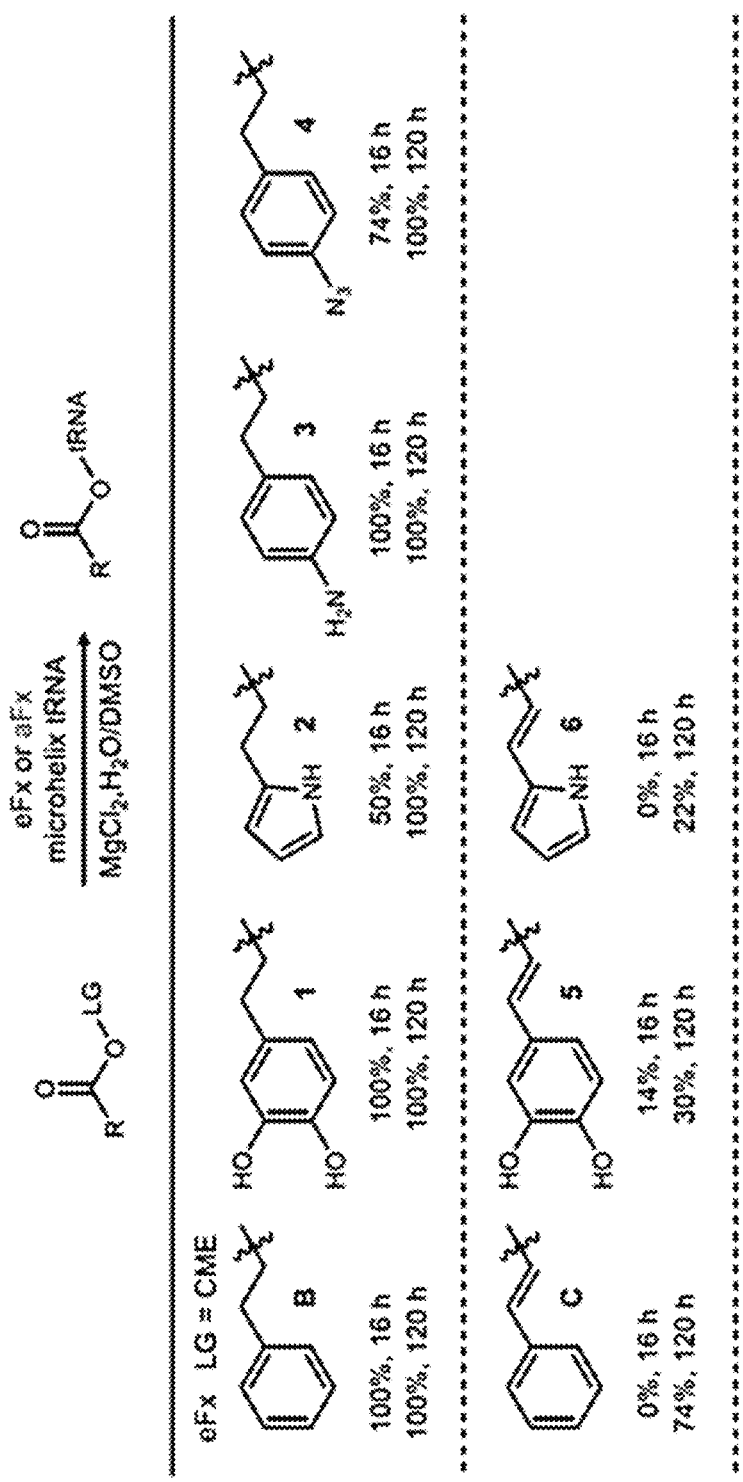
FIG. 15. Numerical acylation yields of microhelix obtained using the expanded substrates. The acylation reaction yields of microhelix with the 32 non-canonical chemical substrates were determined by quantifying the band intensity on the 20% polyacrylamide gel (pH 5.2, 50 mM NaOAc, FIG. 16-18).
Figure 15:
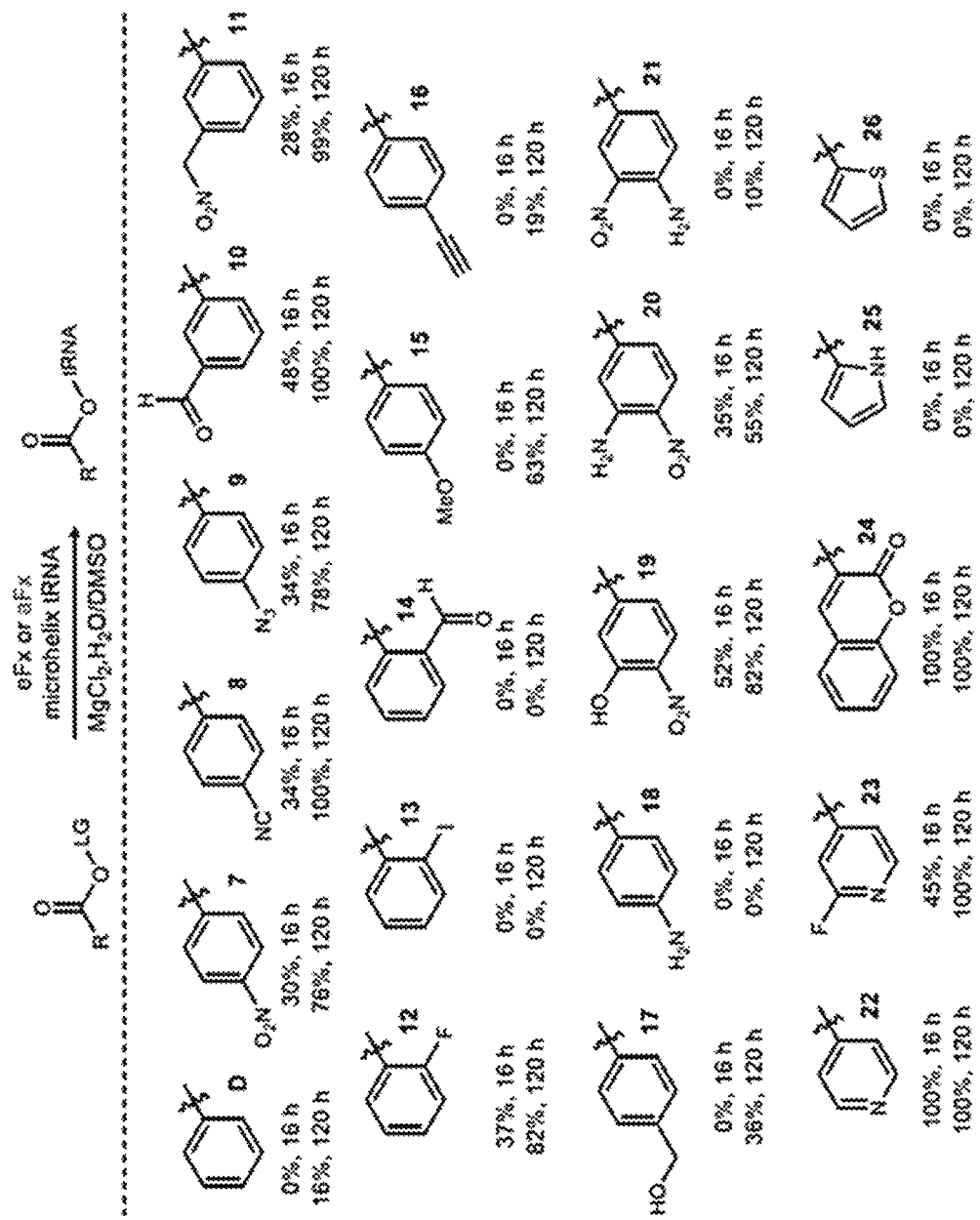
Figure 15:
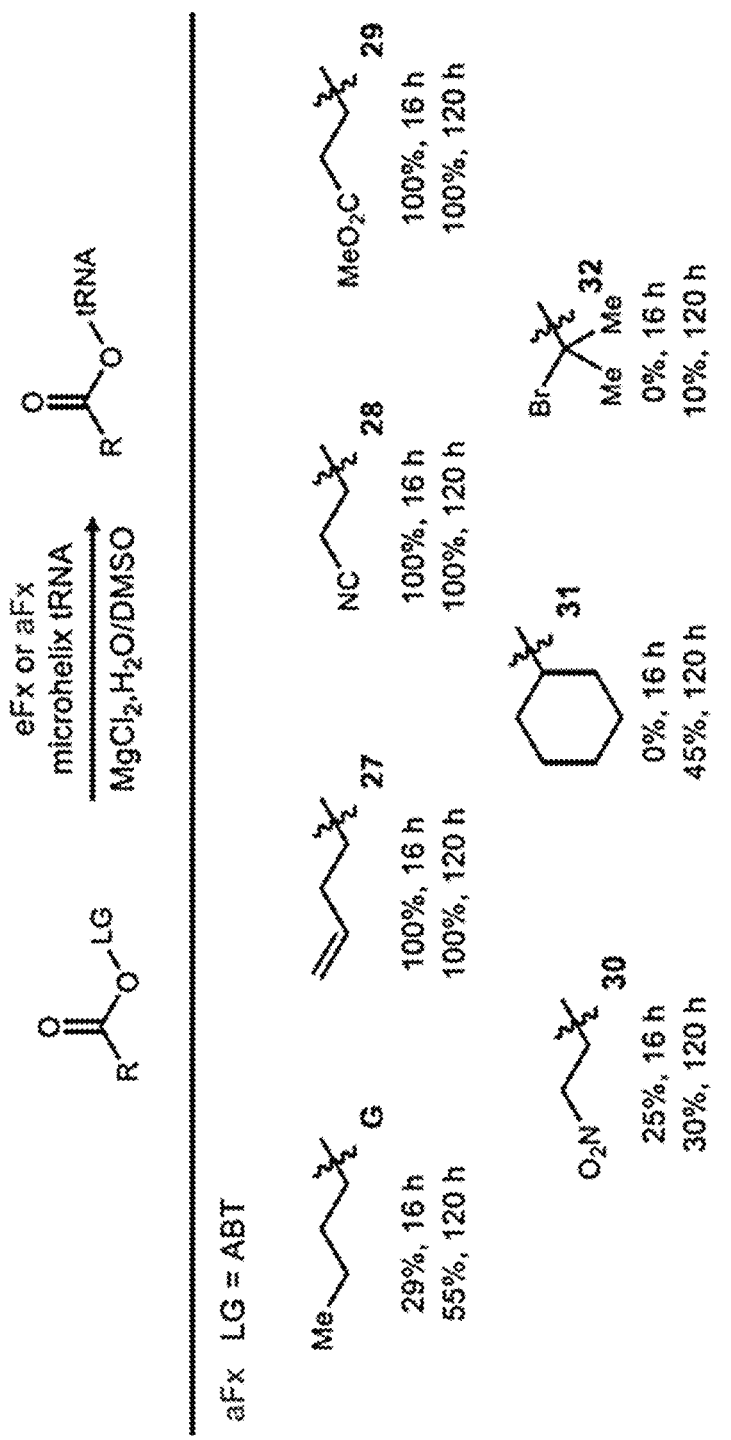

Suitable R moieties may include, but are not limited R moieties disclosed in the present application at FIG. 15. The R moieties thus disclosed may be incorporated into polymers (e.g., sequence defined polymers as disclosed herein).

The disclosed acylated tRNA molecules may comprise any suitable tRNA molecule. Suitable tRNA molecules may include, but are not limited to, tRNA molecules comprising anticodons corresponding to any of the natural amino acids.

The disclosed acylated tRNA molecules may be prepared by reacting a tRNA molecule and a donor molecule in the presence of a flexizyme (Fx).

In some embodiments, the preparation methods may comprise reacting in a reaction mixture: (i) a flexizyme (Fx): (ii) the tRNA molecule; and (ii) a donor molecule having a formula:

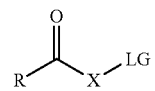

wherein:
tRNA is a transfer RNA linked via a 3' terminal ribonucleotide (e.g. via an ester bond formed with the ribose of a 3' terminal adenosine); and
R is selected from alkyl (e.g., butyl); cycloalkyl (e.g., cyclobutyl, cyclopentyl, or cyclohexyl) optionally substituted with amino; heterocycloalkyl (e.g., a cyclic secondary amine such as piperidinyl or piperazinyl); alkylheterocycloalkyl (e.g., a methyl cyclic secondary amine such as piperidinyl or methyl piperazinyl); alkenyl (e.g., 1-buten-4-yl); cyanoalkyl (e.g., cyanomethyl or cyanoethyl); aminoalkyl (e.g., aminopropyl, aminobutyl, aminopentyl, 1,1-dimethyl-3-amino-propanyl, methylaminopropyl, or aminohexyl); aminoalkenyl (e.g., 1-amino-2-propenyl); alkylcarboxyalkylester (e.g., methylcarboxyethyl ester); haloalkyl (e.g., 2-bromo-propan-2-yl); nitroalkyl (e.g., nitromethyl); aryl (e.g., phenyl, pyrrolyl, thiophenyl, furanyl, pyridinyl, coumarinyl), alkylaryl (e.g., benzyl, ethylphenyl, or ethylpyrrolyl), or alkenylaryl (e.g., ethenylphenyl), wherein the aryl or alkylaryl or alkenylaryl is optionally substituted with one or more substituents selected from hydroxyl (e.g., 3,4-dihydroxylphenyl), hydroxylalkyl (e.g., hydroxylmethyl), amino, aminoalkyl (e.g., aminomethyl), azido, cyano, acetyl, nitro, nitroalkyl (e.g., nitromethyl), halo, alkoxy (e.g., methoxy), and alkynyl;
X is O or S;
and LG is a leaving group.

Figure 20:
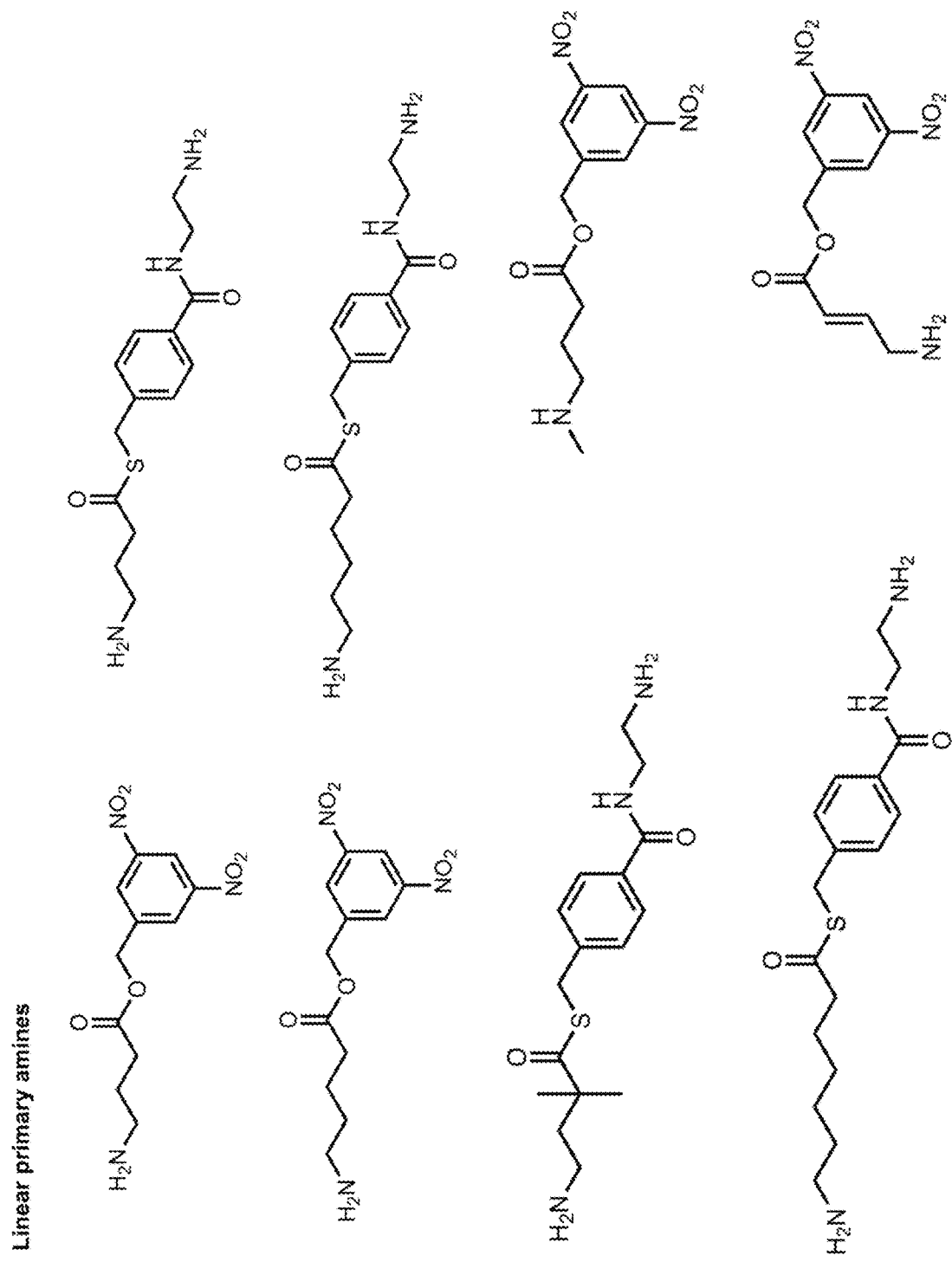
FIG. 20. Exemplary compounds comprising linear primary amine moieties.
Figure 21:
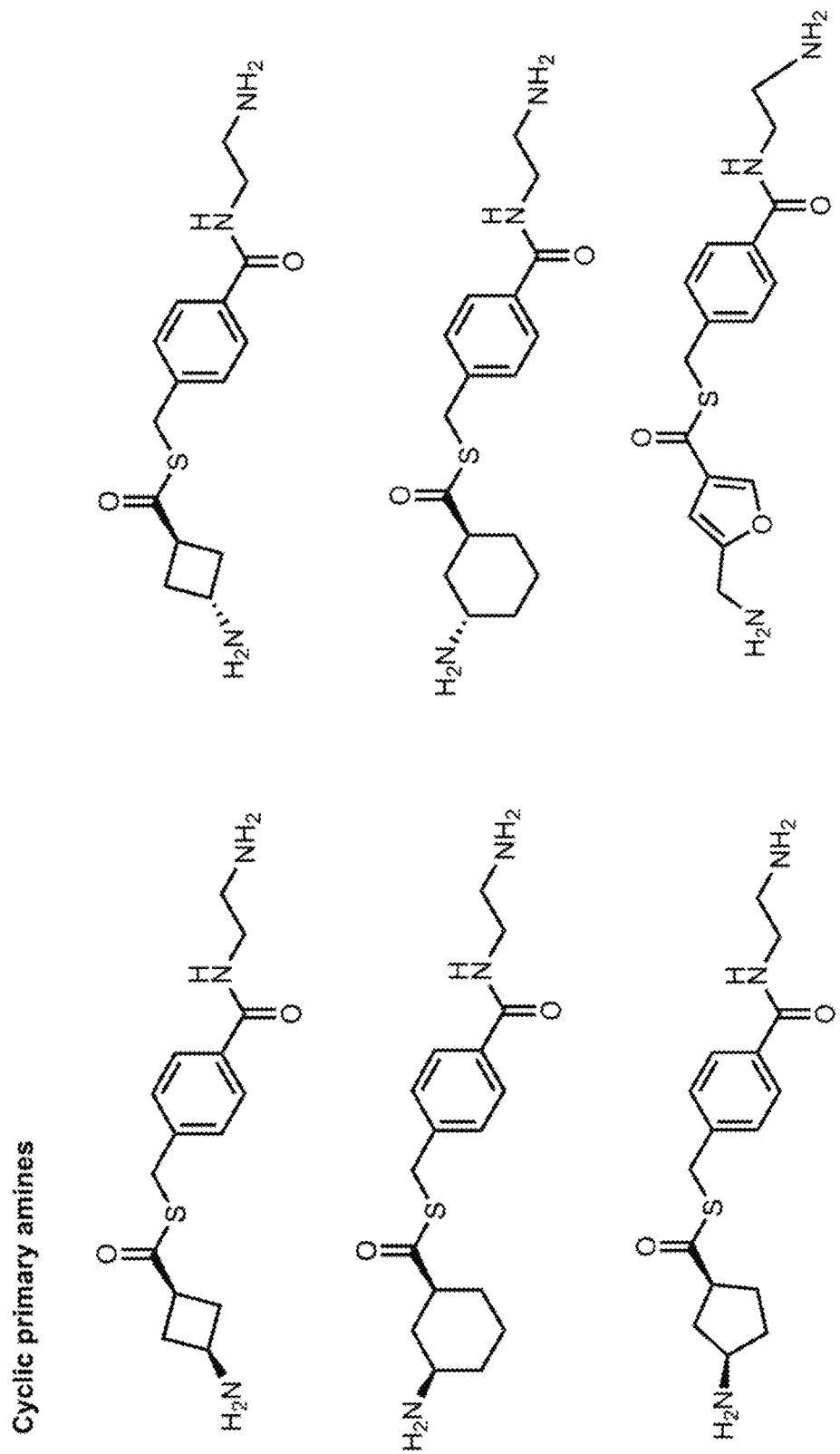
FIG. 21. Exemplary compounds comprising cyclic primary amine moieties.
Figure 22:
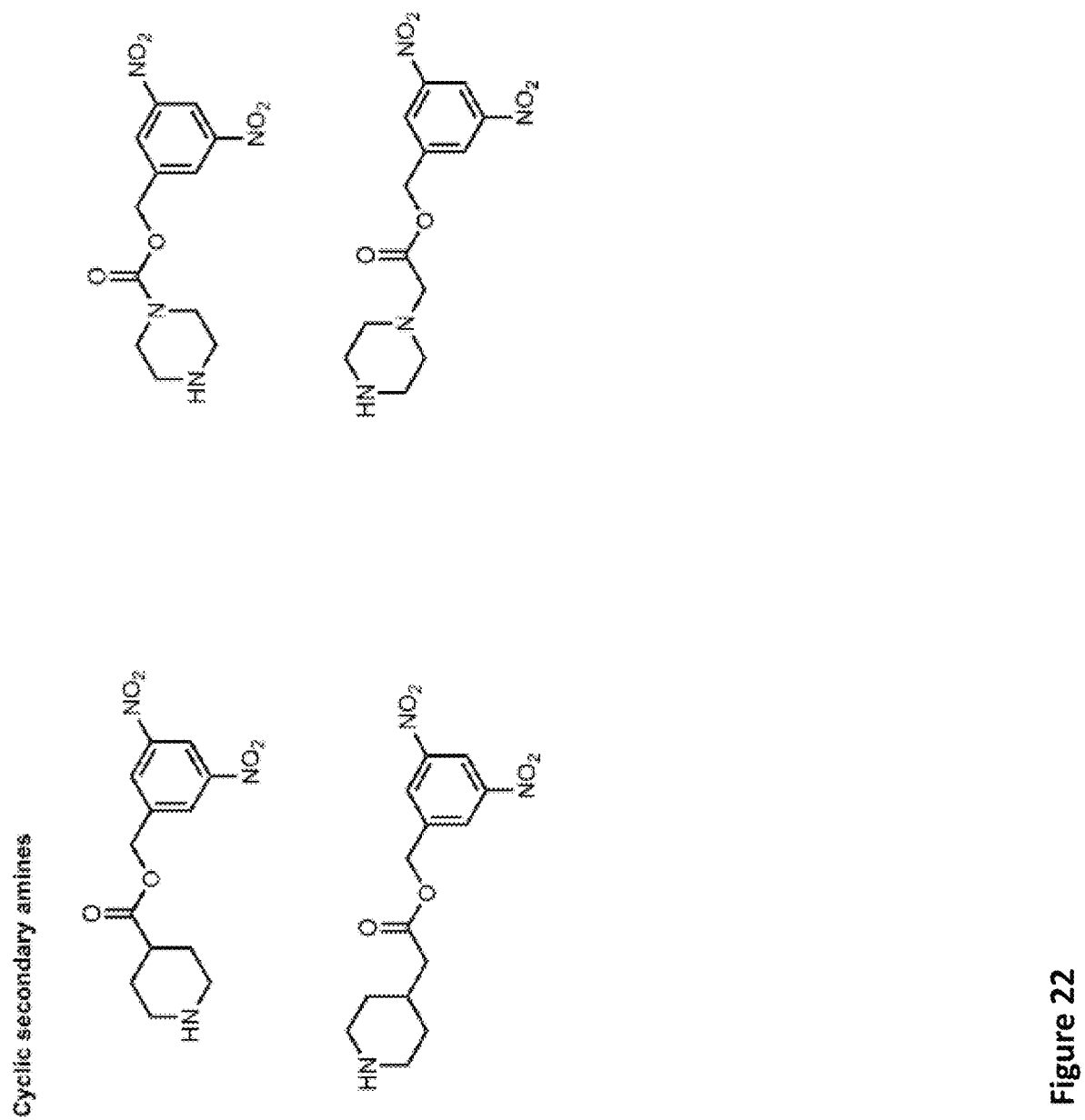
FIG. 22. Exemplary compound comprising cyclic secondary amine moieties.

Suitable R moieties for the donor molecules may include, but are not limited to, R moieties disclosed in the present application at FIG. 15. Suitable donor molecules may include, but are not limited to, donor molecules disclosed in the present application at FIGS. 20-22.

In the preparation method, Fx catalyzes an acylation reaction between the 3' terminal ribonucleotide of the tRNA and the donor molecule to prepare the acylated tRNA molecule (e.g. via an ester bond formed with the ribose of a 3' terminal adenosine of the tRNA molecule and the R moiety).

Any suitable Fx may be utilized in the disclosed preparation methods. Suitable Fx's may include, but are not limited to aFx, dFx, and eFx.

Any suitable tRNA may be utilized in the preparation methods. Suitable tRNA molecules for the preparation methods may include, but are not limited to, tRNA molecules comprising anticodons corresponding to any of the natural amino acids. In some embodiments, the tRNA comprises the anticodon CAU (i.e., the anticodon for methionine). In other embodiments, the tRNA comprises the anticodon GGU (i.e., an anticodon for threonine), the anticodon GAU (i.e., an anticodon for isoleucine), or the anticodon GGC (i.e., an anticodon for alanine).

The donor molecule for the R moiety in the preparation methods typically comprises a leaving group (LG). In some embodiments, LG comprises a cyanomethyl moiety and the donor molecule comprises a cyanomethylester (CME). In other embodiments, LG comprises a dinitrobenzyl moiety and the donor molecule comprises a dinitrobenzylester (DNB). In further embodiments, LG comprises a (2-amino-ethyle)amidocarboxybenzyl moiety and the donor molecule comprises a (2-aminoethyl)amidocarboxybenzyl thioester (ABT).

The disclosed preparation methods are performed under conditions that maximize the yield of acylated tRNA. In some embodiments, the preparation methods are performed under reaction conditions such that at least about 50% of the tRNA in the reaction mixture is acylated after reacting the reaction mixture for 120 hours, and preferably under reaction conditions such that at least about 50% of the tRNA in the reaction mixture is acylated after reacting the reaction mixture for 16 hours.

The disclosed methods, systems, components, and composition may be utilized for preparing sequence defined polymers in vitro and/or in vivo. In some embodiments, the disclosed methods may be performed to prepare a sequence defined polymer in a cell free synthesis system, where the sequence defined polymer is prepared via translating an mRNA comprising a codon corresponding to an anticodon of the acylated tRNA molecule.

In the disclosed methods, the R group of the acylated tRNA molecule is incorporated in the sequence defined polymer during translation of the mRNA. In some embodiments of the disclosed methods, the R group of the acylated tRNA molecule is incorporated in the sequence defined polymer during translation of the mRNA at the start codon (AUG) of the mRNA. In other embodiments of the disclosed methods, the R group of the acylated tRNA molecule is incorporated in the sequence defined polymer during translation of the mRNA at a codon for threonine (e.g., ACC), a codon for isoleucine (e.g., AUC), or at a codon for alanine (e.g. GCC).

The disclosed methods may be performed in order to prepare polymers selected from, but not limited to, polyolefin polymers, aramid polymers, polyurethane polymers, polyketide polymers, conjugated polymers, D-amino acid polymers, β-amino acid polymers, γ-amino acid polymers, δ-amino acid polymers, ε-amino acid polymers, ζ-amino acid polymers, and polycarbonate polymers.

Novel donor molecules or monomers also are disclosed herein. The novel donor molecules or monomers may be incorporated into polymers as disclosed herein (e.g. sequence defined polymers as disclosed herein).

In some embodiments, the polymers comprising the incorporated novel donor molecules or monomers, may be described as a polymer having a formula selected from:

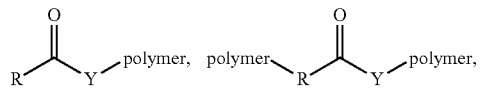

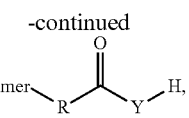

wherein:
R is selected from alkyl (e.g., butyl); cycloalkyl (e.g., cyclobutyl, cyclopentyl, or cyclohexyl) optionally substituted with amino; heterocycloalkyl (e.g., a cyclic secondary amine such as piperidinyl or piperazinyl); alkylheterocycloalkyl (e.g., a methyl cyclic secondary amine such as piperidinyl or methyl piperazinyl); alkenyl (e.g., 1-buten-4-yl); cyanoalkyl (e.g., cyanomethyl or cyanoethyl); aminoalkyl (e.g., aminopropyl, aminobutyl, aminopentyl, 1,1-dimethyl-3-amino-propanyl, methylaminopropyl, or aminohexyl); aminoalkenyl (e.g., 1-amino-2-propenyl); alkylcarboxyalkylester (e.g., methylcarboxyethyl ester); haloalkyl (e.g., 2-bromo-propan-2-yl); nitroalkyl (e.g., nitromethyl); aryl (e.g., phenyl, pyrrolyl, thiophenyl, furanyl, pyridinyl, coumarinyl), alkylaryl (e.g., benzyl, ethylphenyl, or ethylpyrrolyl), or alkenylaryl (e.g., ethenylphenyl), wherein the aryl or alkylaryl or alkenylaryl is optionally substituted with one or more substituents selected from hydroxyl (e.g., 3,4-dihydroxylphenyl), hydroxylalkyl (e.g., hydroxylmethyl), amino, aminoalkyl (e.g., aminomethyl), azido, cyano, acetyl, nitro, nitroalkyl (e.g., nitromethyl), halo, alkoxy (e.g., methoxy), and alkynyl;
Y is O, S, or N; and
"polymer" is a polymer into which the novel donor molecules or monomers have been incorporated, for example, at one or both ends of the polymer and/or internally within the polymer.

ILLUSTRATIVE EMBODIMENTS

The following Embodiments are illustrative and are not intended to limit the scope of the claimed subject matter.

1. Ester or thioester substrates and methods of synthesizing ester and thioester substrates as donor molecules for acylation of tRNA or acylation of a synthetic tRNA (e.g., microhelix RNA), wherein the ester substrates are derivatized from 1) linear (long)-carbon chain (γ, δ, ε, and ζ-) amino acids or 2) cyclic amino acids comprising cyclobutane, cyclopentane, cyclohexne, furan, piperidine, or piperazine moieties, wherein the ester substrates comprise a leaving group which optionally is present in a cyanomethylester (CME), a dinitrobenzylester (DNB), or a (2-aminoethyl) amidocarboxybenzyl thioester (ABT).

2. Use of a flexizyme (Fx) system (e.g., comprising eFx, dFx, or aFx) to acylate tRNA and/or microhelix molecules with a donor moiety of a donor molecule, where the donor moiety may be defined as "R" as disclosed herein, and R may be a non-canonical amino acid or a non-amino acid substrate.

3. Acylation of microhelix or tRNA with non-canonical amino acid substrates or non-amino acid substrates.

4. Incorporation of non-canonical amino acid substrates or non-amino acid substrates into sequence defined polymer by adding pre-charged tRNA into an in-vitro (cell-free) protein synthesis platform.

5. Identification of criteria related to the compatibility between donor molecules and flexizymes for achieving acylation of tRNA or microhelix RNA.

6. Use of eFx, dFx, and aFx to reassign tRNA$^{(fMet(CAU))}$ with a non-canonical synthetic substrate.

7. Use of eFx, dFx, and aFx to reassign tRNA$^{(Pro1E2(GGU))}$ with a non-canonical synthetic substrate.

8. Use of reprogrammed tRNAs for incorporation of non-canonical substrates into a initiating codon (ATG) of a mRNA transcribed in a cell-free protein synthesis system.

9. Use of reprogrammed tRNAs for incorporation of non-canonical substrates into a Thr codon (ACC) of a mRNA transcribed in a cell-free protein synthesis system.

10. Purification and characterization of sequence defined polymers comprising non-canonical substrates as disclosed herein.

11. Non-canonical substrates as disclosed herein, or variants thereof (and/or tRNAs that are acylated with non-canonical substrates, or variants thereof) (including different types of long-carbon chain and cyclic amino acids), as novel monomers for use in cell-free (in vitro) protein or polymer synthesis.

12. Non-canonical substrates as disclosed herein, or variants thereof (and/or tRNAs that are acylated with non-canonical substrates, or variants thereof) (including different types of long-carbon chain and cyclic amino acids), as monomers for use in vivo polymer synthesis.

13. Non-canonical substrates as disclosed herein, or variants thereof (and/or tRNAs that are acylated with non-canonical substrates, or variants thereof) for the synthesis of polymers with non-natural amino acid monomers and/or non-amino acid momoners non-α-amino acid monomers (NNAs) such as polyolefin polymers, polyaramid polymers, polyurethane polymers, polyketide polymers, polycarbonate polymers, conjugated polymers, gamma-amino acid polymers, delta-amino acid polymers, epsilon-amino acid polymers, zeta-amino acid polymers, oligosaccharides, oligonucleotides, polyvinyl polymers, and polyfuran polymers.

14. Novel monomers as disclosed herein and their variants (and/or tRNAs that are acylated with non-canonical monomers, or variants thereof) for the synthesis of polymers with non-natural amino acid monomers and/or non-amino acid momoners non-α-amino acid monomers (NNAs) such as polyolefin polymers, polyaramid polymers, polyurethane polymers, polyketide polymers, polycarbonate polymers, conjugated polymers, gamma-amino acid polymers, delta-amino acid polymers, epsilon-amino acid polymers, zeta-amino acid polymers, oligosaccharides, oligonucleotides, polyvinyl polymers, and polyfuran polymers.

EXAMPLES

The following Examples are illustrative and are not intended to limit the scope of the claimed subject matter.

Example 1—Expanding the Chemical Substrates for Genetic Code Reprogramming

Abstract

Through the development of flexizymes, ribozymes that promiscuously charge arbitrary amino acid monomers to tRNAs, traditional amino acid-tRNA assignments have been expanded to include nonstandard chemical substrate-tRNA pairs that are subsequently incorporated into ribosomal peptides in a site-directed manner. However, the majority of substrates utilized with flexizymes have so far been confined to amino and hydroxy acids, which fundamentally limits the extent of sequence-defined polymers that can be synthesized using the genetic code reprogramming approach. In the present work, we provide extensive empirical data for a wide variety of non-canonical substrates in flexizyme-catalyzed acylation reactions. Upon our results, we expand the range of such substrates into six different types such as phenylalanine analogues, benzoic acid derivatives containing electron-withdrawing or -donating groups, heteroatom rings, and aliphatic chains. From this data, we hypothesize design rules that may play an essential role in expanding the flexizyme-compatible substrates. Furthermore, using wild-type translational machinery in a cell-free protein synthesis system and the reprogrammed fMet-tRNA, we demonstrate the incorporation of 32 non-canonical substrates into ribosomal peptides. Engineered translational machinery might enable the introduction of additional chemical compounds, thereby significantly extending the scope of functionalized polymers that can be produced by the translation apparatus of the cell.

Applications

Applications of the disclosed technology include, but are not limited to: (i) Building a design rule for Fx-compatible chemical substrates; (ii) Expanding the range of non-canonical chemical substrates allowing to produce novel functional polymer; (iii) Reassigning tRNA with the non-canonical substrates using the genetic code reprogramming approach; (iv) Producing engineered peptide by incorporating new functionality; and (v) Understanding the most critical (and dispensable) molecular interaction within the catalytic site of the Fx throughout the computational modeling.

Advantages

Advantages of the disclosed technology include, but are not limited to: (i) Extended the range of Fx-compatible substrate into non-canonical chemical substrates (i. phenylalanine analogues, ii. heteroaromatic substrates, iii. aliphatic substrates, and iv-v. benzoic acid derivatives with electron-withdrawing and -donating group); (ii) Adapted Fx to charge the substrates in high acylation yield; (iii) Determined a design rule for non-canonical substrate based on the substituent effect (electronic and steric effect); (iv) Demonstrated incorporation of the 32 non-canonical substrates into the N-terminus of a peptide on a cell-free platform; the majority of which have never before been found and studied; (v) Purified the 32 peptides from the cell-free protein synthesis reaction and characterized the peptides by mass spectroscopy; (vi) Demonstrated computational modeling to identify the interaction of substrates in the active site of Fx; (vii) This work opens up the possibility to produce novel functional peptide containing an exotic monomer into a peptide, which could allow producing a sequence-defined polymer bearing a novel covalent linkage (e.g., carbon-carbon or carbon-nitrogen bond) between monomers in the ribosome; and (viii) Additionally, this work can expand the study of engineering ribosome variants and other related translational apparatus that allow synthesizing such novel polymers.

Description of the Technology

While current studies have reported more than 150 non-canonical substrates are charged into tRNA and incorporated into a peptide by the Fx approach, and multiple strategies have been devised to synthesize tRNAs charged with non-canonical amino acid, there still exist limitations and gaps in the range of substrates. Mis-acylated tRNAs can be synthesized using protected pdCpA followed by enzymatic ligation (e.g., T4 RNA ligase) with a truncated tRNA that lacks its 3'-terminal CA nucleotides. However, the method is synthetically laborious and often gives poor results due to the generation of a cyclic tRNA by-product that inhibits ribosomal peptide synthesis. The ester linkage for mis-acylated tRNAs can also be obtained by use of engineered synthetase/orthogonal tRNA pairs. However, high specificity of the synthetase toward an amino acid substrate only allows charging a narrow range of substrate pool, which often requires extensive work (e.g., directed evolution) for the development of a new synthetase.

Another means to form a mis-acylated tRNA is through the use of flexizymes (Fx). Fx is an artificial ribozyme with the ability to aminoacylate an arbitrary tRNA. The Fx system has seen widespread success over the last decade in which a wide range (>150) of chemical substrates (α-amino acids, β-amino acids, γ-amino acids, D-amino acids, non-standard amino acids, N-protected (alkylated) amino acids, and hydroxy acids) have been incorporated into ribosomal peptide chain through mis-acylated tRNAs.

Here, we systematically expand the range of substrates toward a variety of non-canonical substrates (Phe analogues, benzoic acid derivatives, heteroatomic molecules, and aliphatic chain), which are still acceptable by Fx and the WT translation apparatus, and moreover demonstrate that using *E. coli* translational machinery through a purified reconstituted system (PURExpress) allows producing numerous functionalized peptide. For comparison to our study, previous studies mostly focus on amino acid variants as a Fx-compatible substrate. Second, hydroxy acid variants were only discovered as a possible substitute for a non-amino acid substrate. Third, no rationale has been developed on designing the Fx-compatible chemical substrate, which allows expanding the boundary of the substrate pool significantly. And finally, no computational research identifying the molecular interaction in the Fx binding pocket exists, which permits and facilitates the efficient design of the monomer for novel polymer synthesis.

Our rationale for designing the substrate for the Fx-catalyzed acylation has the potential to reduce process development and testing timelines for monomer that can provide novel functionality. Further, because we currently lack information on the molecular interaction of substrate to the binding pocket of Fx, our computational modeling result on the intermediate formed during the Fx-catalyzed acylation reaction can be leveraged as a foundational resource for chemists, biochemists, and molecular biologists as well as protein engineers to select a proper non-canonical substrate. Specifically, computational efforts would greatly benefit from our result, as it may aid the efficient mutational study within the Fx's active site.

Additionally, because the discovery of 32 non-canonical substrates on the five different subsets outlines diversity of substrates and characterizes its impact on peptide synthesis, this finding could be used to prototype other non-canonical chemical substrates. Finally, our substrate variants set could be readily applied to chemical substrate variants for the synthesis of various peptides, including precursors for therapeutic medicines and macrocyclic materials. This novel and comprehensive study have advantages for fundamental and synthetic/engineering biology.

Related Technology

Related technology may be described in one or more of the following patent documents and non-patent documents which are incorporated herein by reference in their entireties: U.S. Pat. Nos. 5,478,730; 5,556,769; 5,665,563; 6,168,931; 6,518,058; 6,783,957; 6,869,774; 6,994,986; 7,118,883; 7,189,528; 7,338,789; 7,387,884; 7,399,610; 9,410,148; 9,528,137; 9,951,392; 9,688,994 and 9,783,800. U.S. Published Patent Application Nos 2009/0281280; 2012/0171720; 2016/0060301; 2016/0083688; 2016/0209421; 2016/0289668; 2017/0073381; 2017/0306320; 2017/0349928; and 2018/0016614. Published International Applications WO2008/059823; WO2011/049157; WO2012/026566; WO2012/074129; WO2012/074130; WO2013/100132; WO2014/119600; WO2016/199801; EP2141175; JP2013071904; JP2018509172; and JP2017216961. Non-patent documents: Passioura and Suga, "Flexizymes, their evolutionary history and diverse utilities," Top Curr Chem. 2014:344-45.

Example 2—Expanding the Chemical Substrates in Genetic Code Reprogramming

Reference is made to the presentation entitled "Expanding the chemical substrates in genetic code reprogramming," Joongoo Lee, Kenneth Schwieter, Do Soon Kim, Jeffrey Moore, and Michael Jewett, to be presented on Jun. 3-4, 2018, at the 2018 Synthetic biology: Engineering, Evolution, & Design (SEED) conference, Scottsdale, Ariz., which content is incorporated herein by reference in its entirety.

Abstract

The translation apparatus is the cell's factory for protein synthesis. In the synthesis, the biological machines that carry out translation produce polymers with a peptide backbone by coupling α-amino acids according to the encoding sequences of an mRNA template. Although many pioneering works have expanded the genetic code to more than 150 nonstandard amino acids for protein synthesis, the covalent linkage of polymers synthesized by ribosomes has been confined to polypeptide bonds (amides) or polyester bonds. Herein, we explored new environments and monomer templates that allow production of organic sequence-defined polymers (SDPs) with a wide variety of covalent chemical bonds. A flexizyme system is used to reassign individual codons and SDPs bearing a non-peptide backbone are produced under controls of the reprogrammed genetic code using an engineered cell-free translation system.

Introduction

Protein synthesis by ribosomes is achieved via polymerization of amino acids that are covalently linked to transfer RNAs (tRNAs) via aminoacylation (i.e., "charging"). Thus, a tRNA that is aminoacylated with an amino acid is referred to as a "charged tRNA." A ribosome translates codons that are present in an mRNA via matching a corresponding anticodons present on charged tRNAs. The amino acid of a charged tRNA is thus incorporated via the ribosome into a nascent polypeptide corresponding to the translated mRNA.

In modern organisms, protein-based enzymes called aminoacyl tRNA synthetases (ARSs) catalyze aminoacylation of tRNA. However, ribozymes that aminoacylate tRNA by using activated amino acids have been discovered in vitro, which have been termed "flexizymes." Flexizymes and their use for genetic reprogramming are known in the art. (See, e.g., Ohuchi et al., "The flexizyme system: a highly flexible tRNA aminoacylation tool for the translation apparatus," Curr Opin Chem Biol. 2007 Ocxt; 11(5):537-42; Xiao et al., Structural basis of specific tRNA aminoacylation by a small in vitro selected ribozyme," Nature 454, 358-361 (2008); Passioura and Suga, "Flexizyme-Mediated Genetic Reprogramming As a Tool for Noncanonical Peptide Synthesis and Drug Discovery," Angewandte Chemie, Volume 19, Issue 21, pages 6530-6536, May 17, 2013; and Katoh et al., Advances in in vitro genetic code reprogramming in 2014-2017, Synthetic Biology, Volume 3, Issue 1, May 31, 2018; the contents of which are incorporated herein by reference in their entireties). Flexizymes can be evolved and selected in vitro to catalyze aminoacylation of tRNA with nonstandard amino acids, and tRNAs thus charged with nonstandard amino acids can be utilized to incorporate nonstandard amino acids in nascent polypeptides. Flexizyme systems thus enable reprogramming of the genetic code by reassigning the codons that are generally assigned to natural amino acids to nonstandard amino acids or other residues, and thus mRNA-directed synthesis of non-natural polypeptides can be achieved.

FIG. 1 illustrates the flexizyme system. FIG. 1.A) illustrates the crystal structure of a flexizyme. FIG. 1.B) illustrates acylation of tRNA by a flexizyme and the leaving groups commonly used for preparing activated ester substrates, which can be loaded on tRNA or a microhelix via a flexizyme.

Results

Figure 2:
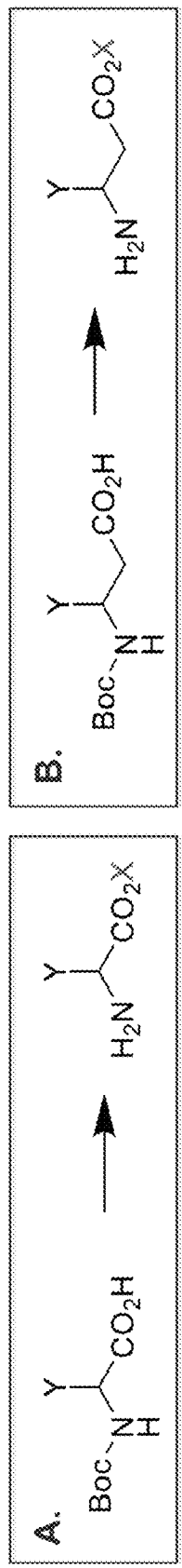
FIG. 2. Preparation of chemical substrates. Boc-protected a-amino acids and Boc-protected b-amino acids were converted to esterified substrates for acylation.

Chemical substrates for loading on tRNA or a microhelix can be prepared by converting protected α-amino acids or protected β-amino acids to corresponding esters. (See FIGS. 2.A. and 2.B., respectively).

Figure 3:
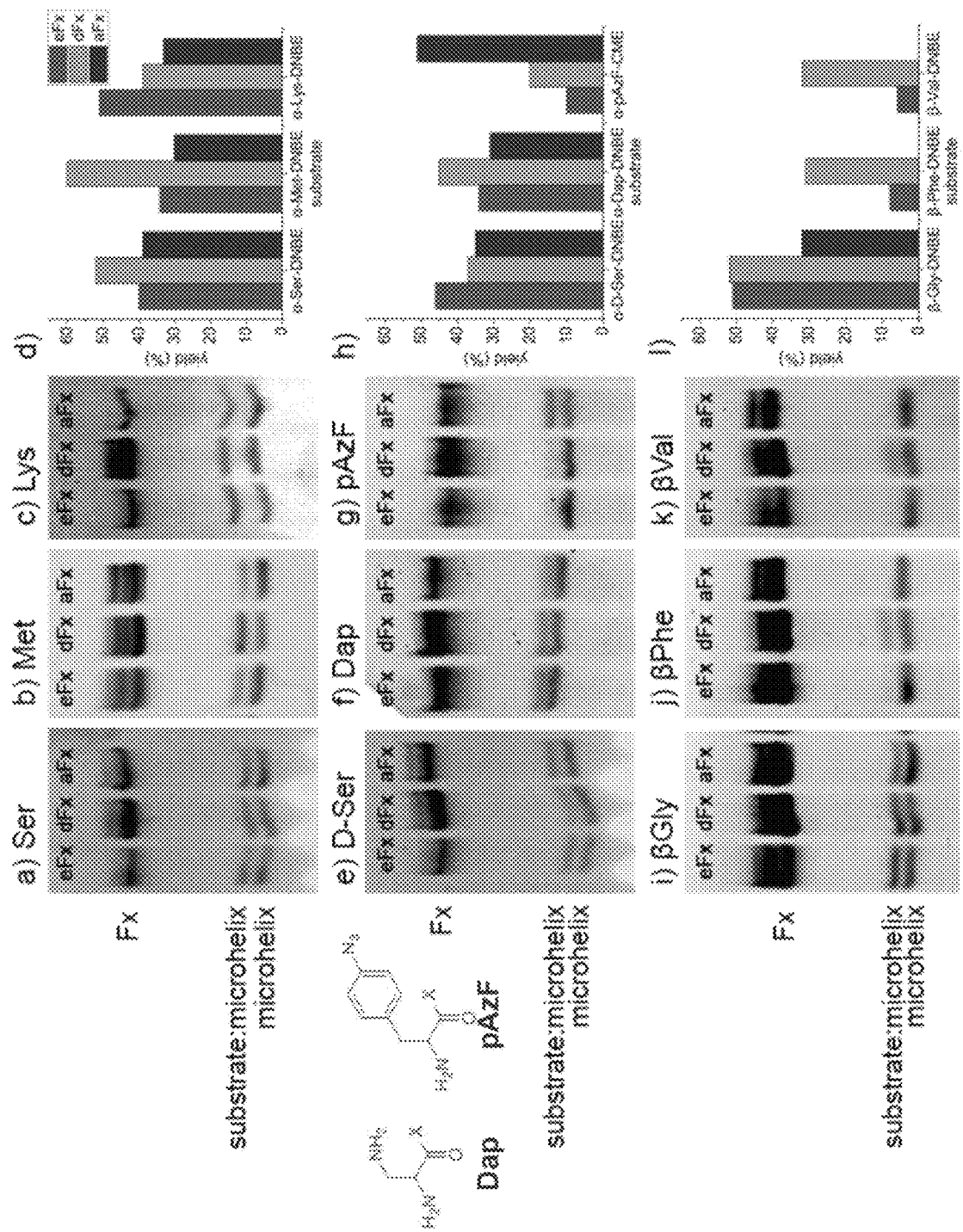
FIG. 3. Optimization of flexizyme (Fx)—catalyzed aminoacylation.
Figure 4:
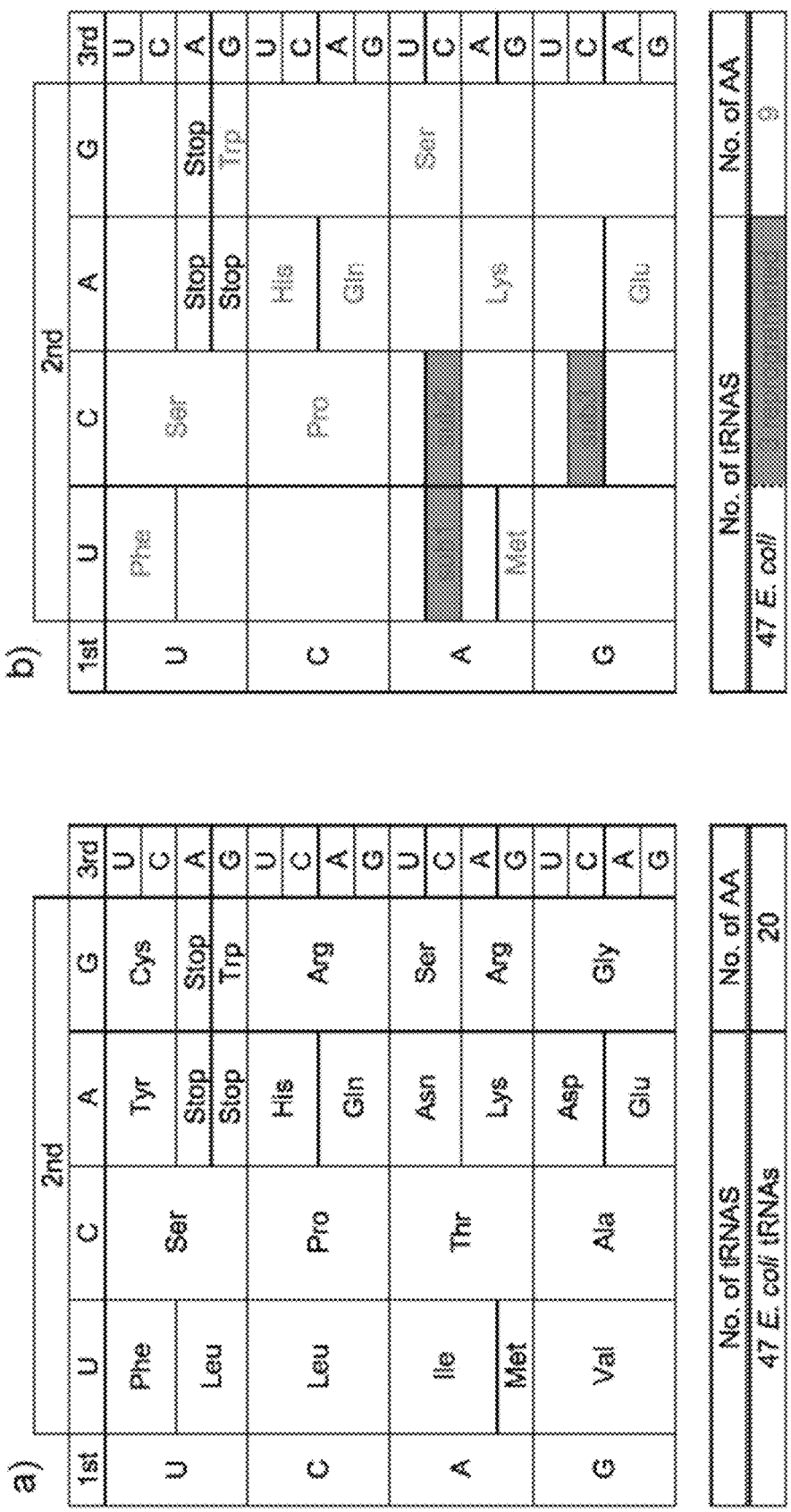
FIG. 4. Genetic code reprogramming. Sub1, Sub2 and Sub3 indicate the codons corresponding to the reprogrammed tRNAs.
Figure 5:
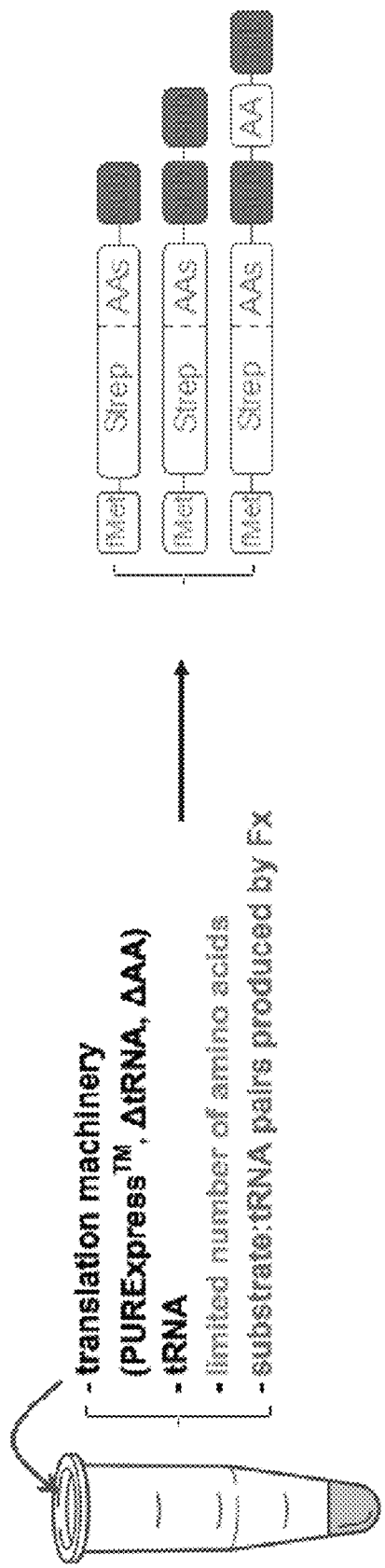
FIG. 5. Schematic of method for incorporating amino acids into a polypeptide.
Figure 6:
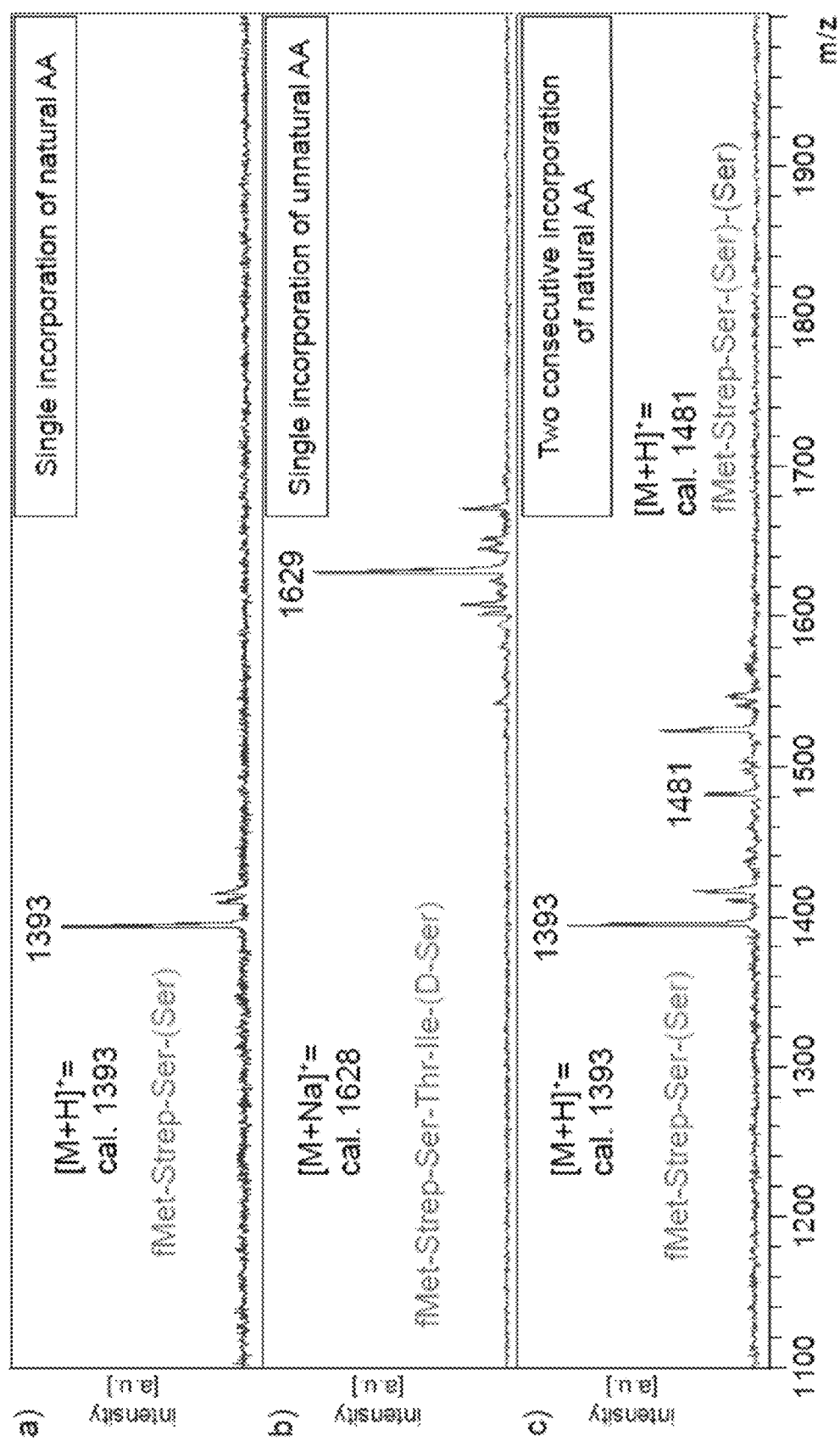
FIG. 6. Characterization of the synthetic polypeptides containing the incorporated amino acid.
Figure 6:
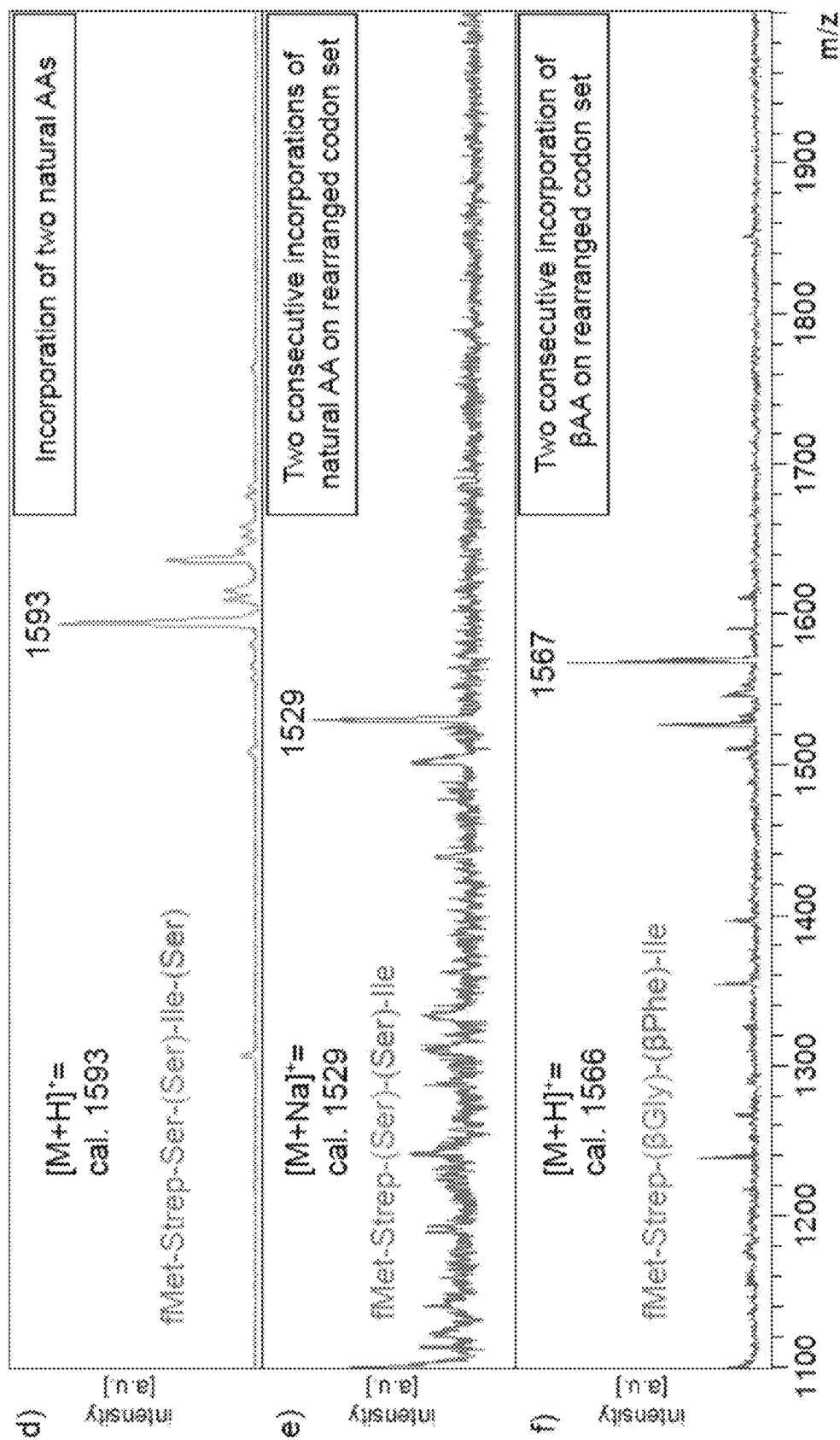

Flexizyme (Fx) catalyzed aminoacylation was optimized using a microhelix (22 nt) as a tRNA mimic. (See FIG. 3). The optimization reactions were performed in a 50 mM HEPES-KOH (PH 7.5) or Bicine (pH 8.8) buffer containing 0.3 M MgCl2, 1 µM microhelix, 5 µM Fx, 2.5 mM of amino acid substrates (e.g., esterified amino acid substrates), and 20% DMSO. The reaction mixture was incubated at 0° C. and monitored over 72 h. The acylated product yield was determined by quantifying the band intensity using software (ImageJ). Micxrohelix was obtained commercially (Integarated DNA Technologies (IDT)) and used as received. tRNAs of interest were acylated using L-Ser, D-Ser, β-Gly, and β-Phe under the same conditions used in the microhelix experiment, and the reprogrammed tRNA were subsequently added into a cell-free synthesis platform (PURExpress). tRNAs corresponding to AUC, ACC, and GCC were reassigned with non-natural amino acid substrates using the Fx system. (See FIG. 4). Using a cell-free protein synthesis (CFPS) platform (see FIG. 5) and the reassigned tRNAs, the non-natural amino acids were incorporated into a polypeptide. (See FIG. 6 $a$)-$f$)). We observed that there are optimal codon orders in mRNA for consecutive incorporation of amino acids. (See FIG. 6 $e$) and $f$)).

Conclusions

Figure 7:
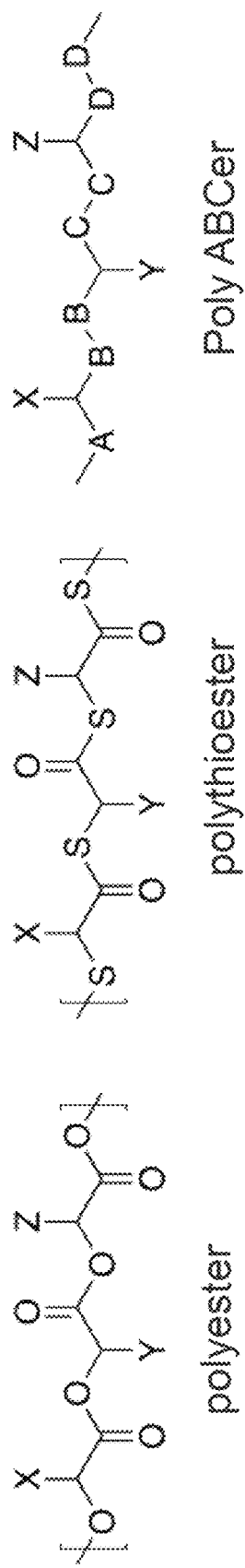
FIG. 7. Possible polymer backbones that can be formed utilizing tRNAs that are charged with ester monomers, thioester monomers, or ABC monomers.

We will design monomers that allows the formation of novel covalent chemical bonds by a ribosome within a nascent sequence-defined polymer and synthesis of such sequence-defined polymers in a cell-free synthesis (CFPS) platform. Potential polymer backbones include polyester backbonds, polythioester backbones, or generic "poly-ABCer" backbones. (See FIG. 7). As a proof of concept, we charged tRNAs with nine amino acids via our Fx system and found that the nine amino acids that were charged on the tRNAs were incorporated into a polypeptide in a CFPS platform.

Example 3—Expanding the Chemical Substrates in Genetic Code Reprogramming

Abstract

The site-specific incorporation of noncanonical amino acids into polypeptides through genetic code reprogramming is a powerful approach for making bio-based products that extend beyond natural limits. While a diverse repertoire of chemical substrates can be used in ribosome-mediated polymerization, most have been limited to amino- and hydroxy-acids. Here, we set out to identify design rules for flexizyme-mediated charging of noncanonical monomers to tRNAs that would expand substrate scope for ribosome mediated polymerization. To achieve this goal, we synthesized 38 new substrates based on 4 scaffolds (phenylalanine derivatives, benzoic acid derivatives, heteroaromatic monomers, and aliphatic monomers) and found that 32 could be acylated onto tRNA using under optimized reaction conditions. Of these substrates, all could be incorporated into ribosomal peptides at the N-terminus using in vitro translation. Our work provides design rules for flexizyme catalyzed acylation and expands the range of chemical substrates for repurposing the translation apparatus.

Introduction

The translation apparatus is the cell's factory for protein synthesis, stitching together L-α-amino acid substrates into sequence-defined polymers (proteins) from a defined genetic template. With protein elongation rates of up to 20 amino acids per second and remarkable precision (fidelity of ~99.99%)[1-3], the *Escherichia coli* protein biosynthesis system (the ribosome and associated factors necessary for polymerization) possesses an incredible catalytic capability. This has long motivated efforts to understand and harness artificial versions for biotechnology. In nature, however, only limited sets of protein monomers are utilized, thereby resulting in limited sets of biopolymers (i.e., proteins). Expanding nature's repertoire of ribosomal monomers[4-12] could yield new kinds of bio-based products with diverse genetically encoded chemistry. So far, the natural ribosome has been shown capable of selectively incorporating a wide range chemical substrates into an elongating polymer chain, especially in vitro where greater control and freedom of design is possible.[13] These include α-1, β-[15], γ-[16], D-[17,18], N-alkylated[19,20], noncanonical amino acids[21], hydroxy acids[22,23], peptides[24], oligomeric foldamer-peptide hybrids[25], and non-amino carboxylic acids[26,27]. The impact of incorporating such a broad and diverse set of monomers, especially for the site-specific incorporation of noncanonical amino acids into peptides and proteins, has been the production of novel therapeutics, enzymes, and materials[28-34].

For ribosomal monomers to be selectively incorporated into a growing chain by the ribosome, they must be covalently attached (or charged) to transfer RNAs (tRNAs), making aminoacyl-tRNA substrates. Multiple strategies have been devised to synthesize such noncanonical aminoacyl-tRNAs, or 'mis-acylated' tRNAs. The classical strategy is chemical aminoacylation, which requires the synthesis of a 5'-phospho-2'-deoxyribocytidylyriboadenosine (pdCpA) dinucleotide, ester coupling with the amino acid substrate, and enzymatic ligation (e.g., T4 RNA ligase) with a truncated tRNA[35-39]. Unfortunately, chemical aminoacylations are laborious and technically difficult, often giving poor results in translation due to the generation of a cyclic tRNA by-product which inhibits ribosomal peptide synthesis.[40] Another strategy is to engineer protein enzymes called aminoacyl-tRNA synthetases (aaRS), which naturally charge canonical amino acids to tRNAs, by directed evolution.[41-50] However, aaRSs have limited promiscuity for noncanonical chemical substrates, and are generally confined to a narrow range of amino acid analogues that resemble natural ones.

More recently, an alternative approach to produce mis-acylated tRNAs that uses an RNA enzyme known as flexizyme (Fx) was developed. This flexible and powerful approach, pioneered by Suga and colleagues, is capable of exclusively aminoacylating the 3'-OH of an arbitrary tRNA[51] (FIG. 8$a$) with activated esters.[52-55] Through directed evolution and sequence optimization, three different flexizymes (eFx, dFx, and aFx)[5] have been developed to recognize specific combinations of substrate:activating groups. A crystallographic study[56] elucidated that an aryl group either on the substrate side chain or leaving group is crucial for substrate interaction with the catalytic binding pocket of Fx. For example, eFx acylates tRNA with cyanomethyl ester (CME)-activated acids containing aryl functionality, while dFx recognizes dinitrobenzyl ester (DNBE)-activated non-aryl acids[57]. For substrates that lack an aryl group or have poor solubility due to the presence of DNBE, aFx has been developed recognizing a (2-aminoethyl)amidocarboxybenzyl thioester (ABT)[58] leaving group which provides the required aryl group and better aqueous solubility (FIG. 8a, bottom panel).

The unique potential of the flexizyme approach is that virtually any amino acid can be charged to any tRNA, as long as the side chain is stable toward the conditions of the acylation reaction (or suitably protected/deprotected in the case of reactive side chains), enabling the reassignment of a specific codon to an amino acid de novo. As such, the development of flexizyme has significantly expanded the known permissible space of monomers used in translation by genetic code reprogramming. The range of monomers incorporated has so far, however, mainly been limited to amino[23] and hydroxy acids[33]. Design rules for flexizyme mediated charging, which may more effectively guide the search for noncanonical monomers, are still being identified. To expand the available design space for template guided polymerization by the ribosome to polymers beyond polypeptides or polyesters, new efforts to explore constraints that limit the scope of noncanonical monomer diversity permissible to both flexizyme mediated charging and translation by the ribosome are needed.

Figure 8:
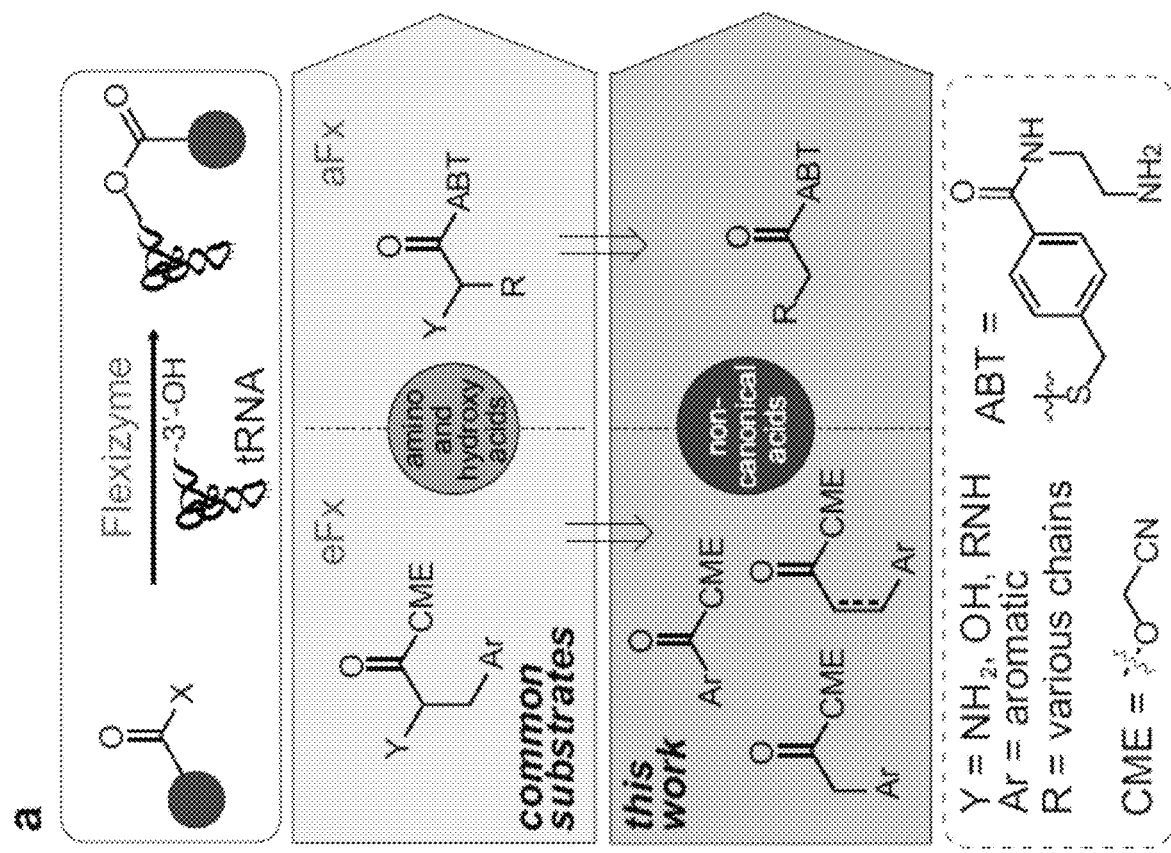
FIG. 8. Expanding the chemical substrate scope of flexizymes for genetic code reprogramming. a) Flexizyme (Fx) recognizes the 3'-CCA sequence of tRNAs59 and catalyzes the acylation of tRNA using acid substrates. Fx has been so far used to incorporate a limited set of mostly common amino and hydroxy acids. In this work, we explore the substrate specificity of Fx for additional noncanonical acid substrates containing an aromatic group either on the side chain or on the leaving group (purple panel). b) An *E. coli* cell-free protein synthesis system reconstituted from the purified wild type translational machinery (PUREexpress™) was used to produce peptide, 60 containing such noncanonical acid substrates. This approach for incorporating noncanonical monomers at the N-terminus of peptides is well established. c) 32 noncanonical acid substrates comprising a wide variety of functional groups were incorporated into the N-terminus of a peptide.
Figure 8:
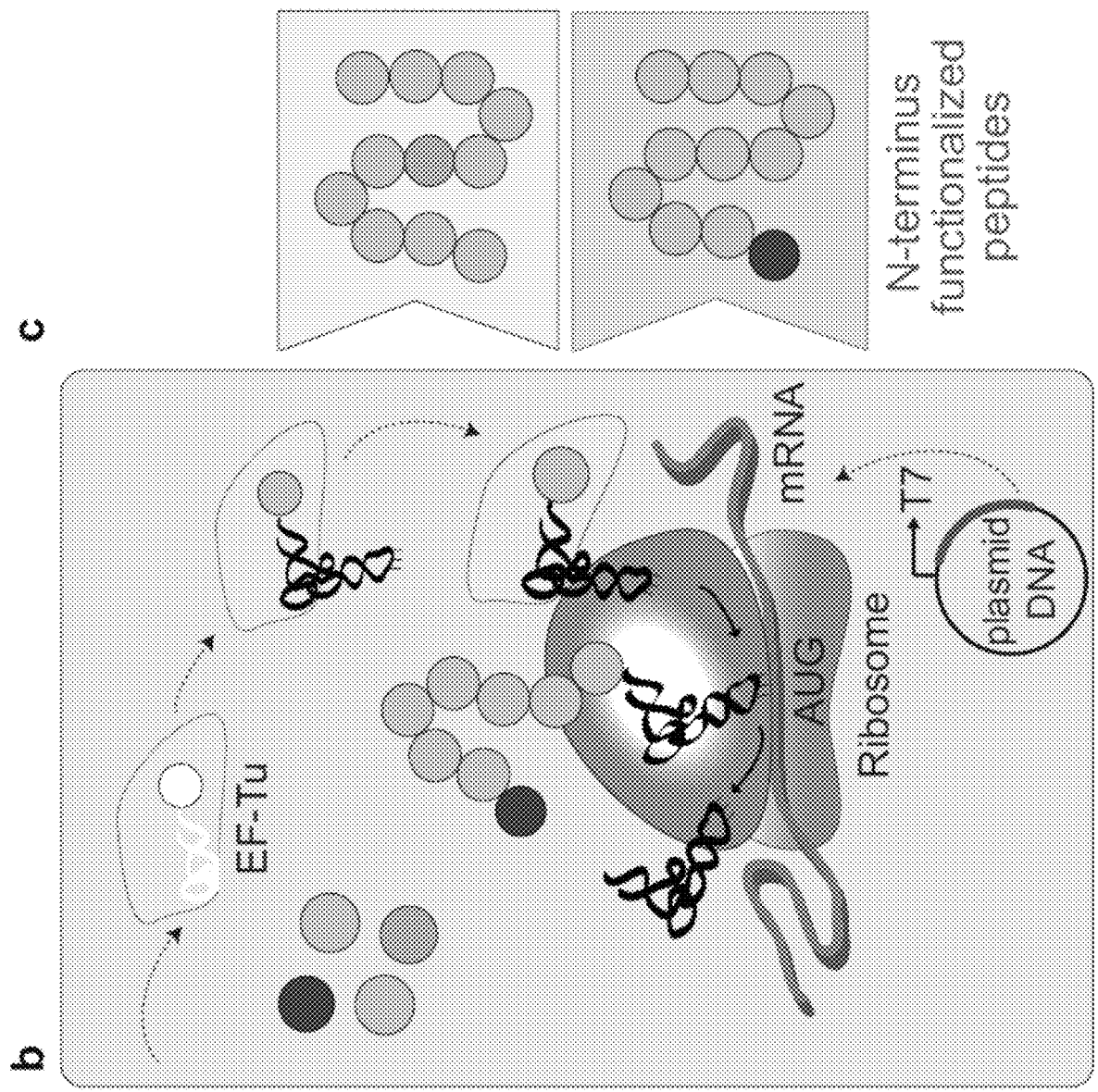

Here, we set out to fill this gap in knowledge by systematically expanding the range of chemical substrates for flexizyme-mediated charging followed by translation using natural ribosomes (FIG. 8). Specifically, we synthesized a repertoire of 38 phenylalanine derivatives, benzoic acid derivatives, heteroaromatic monomers, and aliphatic monomers that were designed based on known compatible scaffolds. We deliberately chose potential substrates that feature chemical moieties inaccessible to native ribosomally synthesized peptides or their post-translationally modified derivatives, or that could support novel A-B polycondensation reactions (rather than amide and ester bonds). After chemical synthesis of the activated esters, we assessed the ability of flexizyme charging of these substrates to tRNAs by varying pH and time to create optimized acylation conditions. We found that 32 of the 38 substrates are charged to tRNAs from which trends emerged that will help to more effectively guide the search for novel monomers. To gain insights into the substrate-flexizyme compatibility, we also used computational modeling for studying the molecular interaction of the nucleic acid residues in the binding pocket of flexizyme with the substrates showing high or low acylation yield. Finally, we asked if the novel tRNA-monomers could be used by the wild type ribosome in the commercially available PURExpress™ cell-free translation system. While N-terminal incorporation of novel monomers into peptides from substrate-tRNA$^{fMet}$ complexes was possible for 32 of the substrates, incorporation into the C-terminus of peptides was not possible by wild type ribosomes.

Results and Discussion

Expanding the Substrate Repertoire for Flexizyme (Fx)-Catalyzed RNA Acylation.

To expand the substrate scope for Fx-catalyzed tRNA mis-acylation, we initially determined compatible substrate scaffolds. For this, we benchmarked the molecular structure of CME-activated phenylalanine (Phe-CME, A, FIG. 9a, middle panel) as the optimal substrate for eFx[51, 56, 59, 61] and investigated eFx's substrate flexibility toward a series of five substrates with increasing degree of modification from the parent structure, A (B-F, FIG. 9a, middle panel). These include: B (hydrocinnamic acid): amine excluded from A; C (cinnamic acid): the unsaturated form of B; D and E (benzoic and phenylacetic acid, respectively): two or one carbon excluded from B; and F (propanoic acid): aryl replaced with aliphatic group in B.

Figure 9:
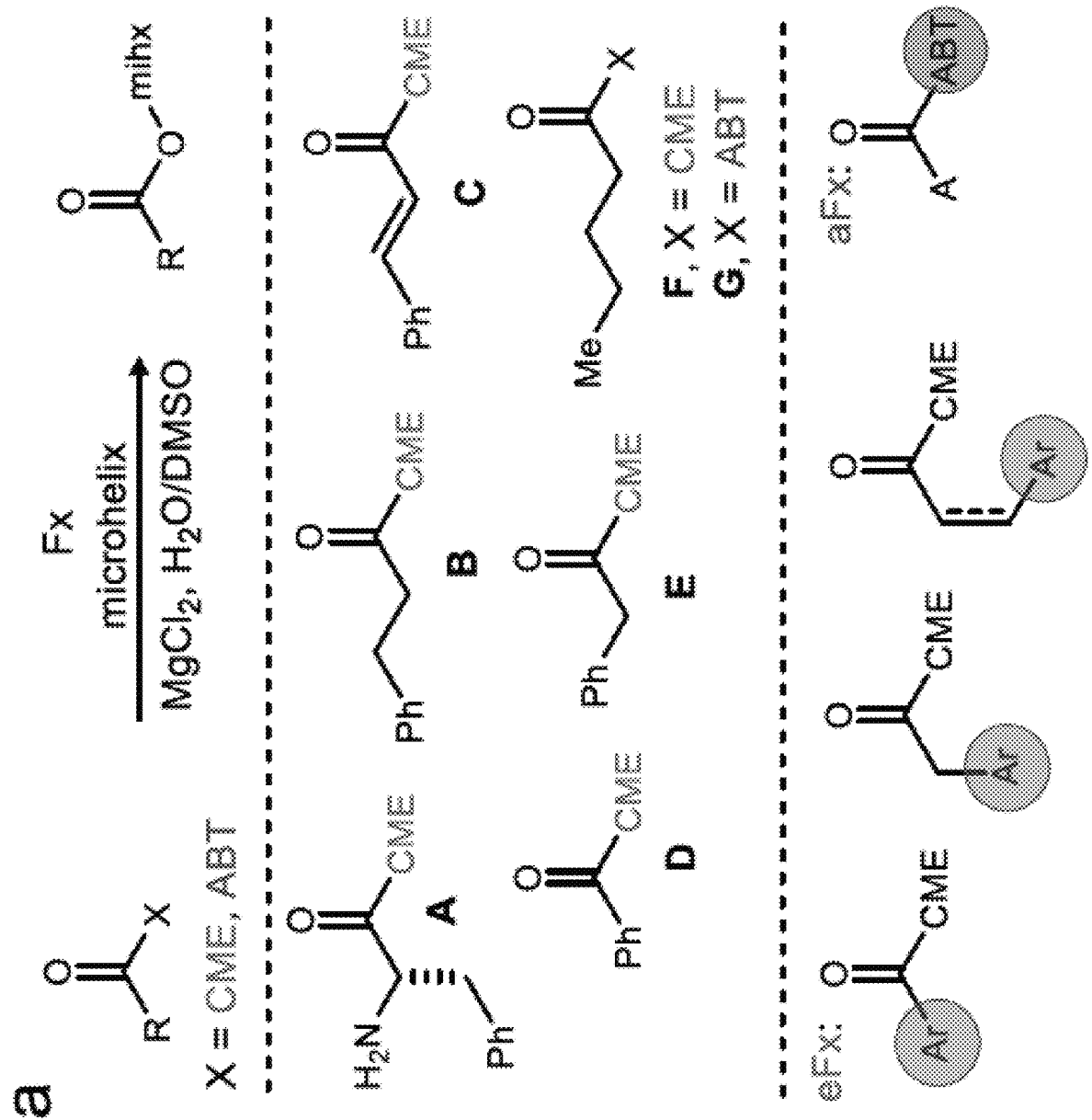
FIG. 9. Optimized reaction conditions facilitate Fx-catalyzed acylation with novel substrates. Acid denaturing PAGE analysis under various conditions for Fx-catalyzed acylations of a microhelix tRNA (22 nt) with Phe (A) and structurally diversified Phe analogues (B-G). The acylation reactions were performed using eFx (45 nt) or aFx (47 nt) and monitored over 120 h at two different pHs (7.5 vs. 8.8).
Figure 9:
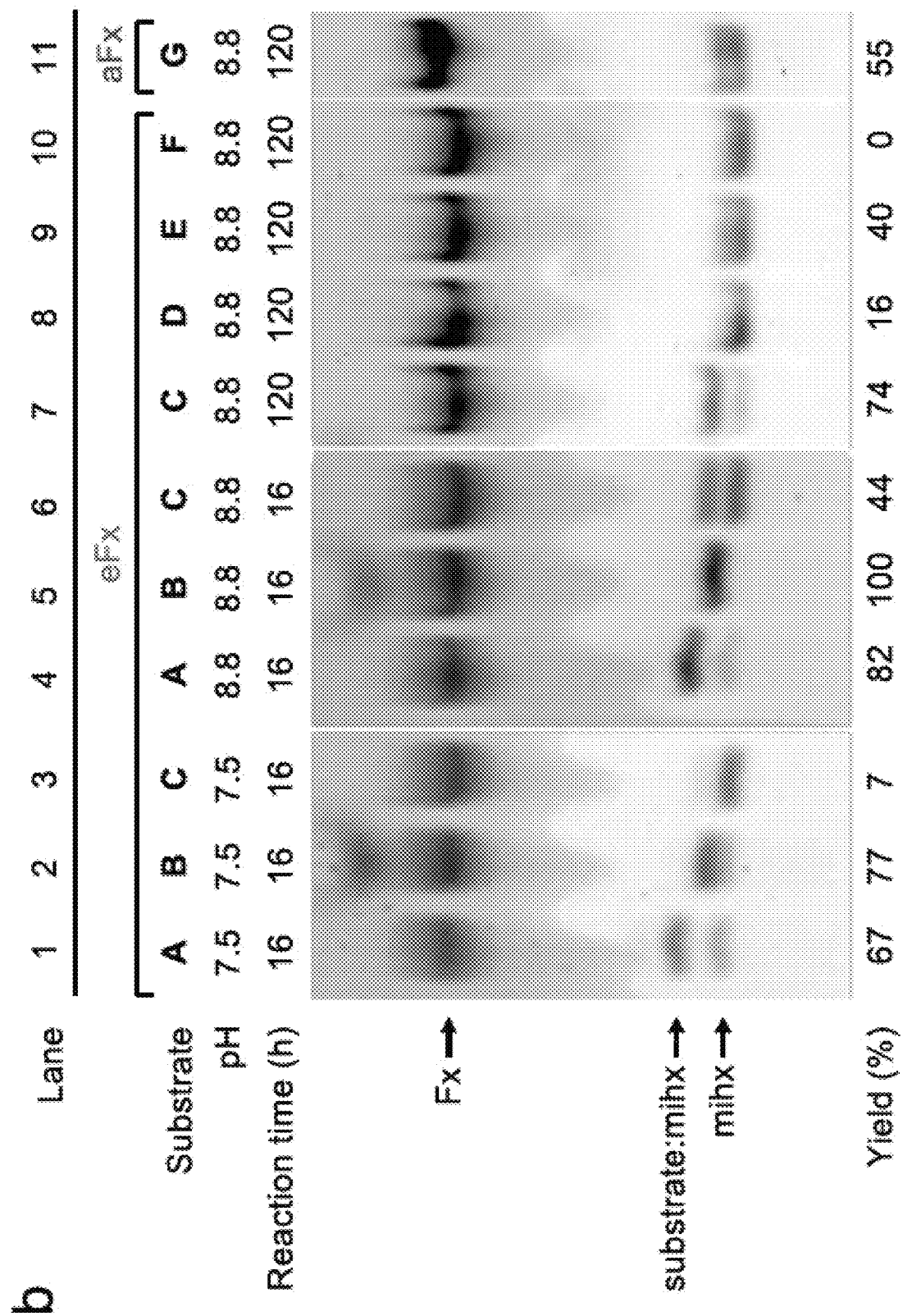
Figure 13:
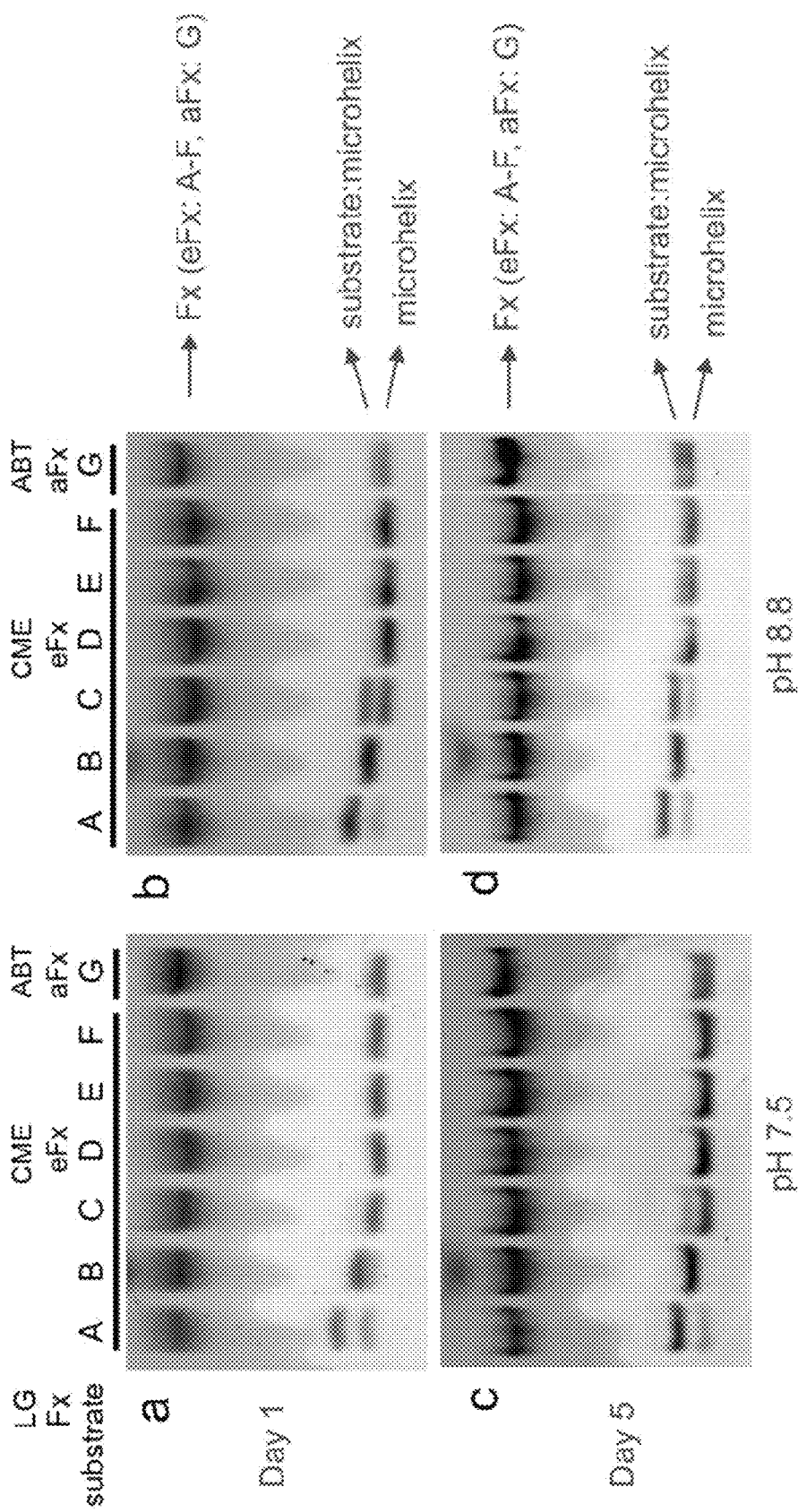
FIG. 13. Acylation of microhelix with the seed substrates. The Fx-catalyzed acylation reaction using the six representative substrates (Phe-CME (A), hcinA-CME (B), cinA-CME (C), benA-CME (D), PhAACME (E), penA-CME (F), penA-ABT (G) were monitored at two different pH (7.5 and 8.8) over 120 h. In general, high pH (pH 8.8) and long incubation time (120 h) gives high reaction yield. A part of FIG. 8*a* (lane A-C), 8b (lane A-C), and 8d (lane C-G) was used to produce FIG. 9. LG: leaving group, Fx: Flexizyme, CME: cyanomethylester, ABT: (2-aminoethyl)amidocarboxybenzyl thioester.
Figure 14:
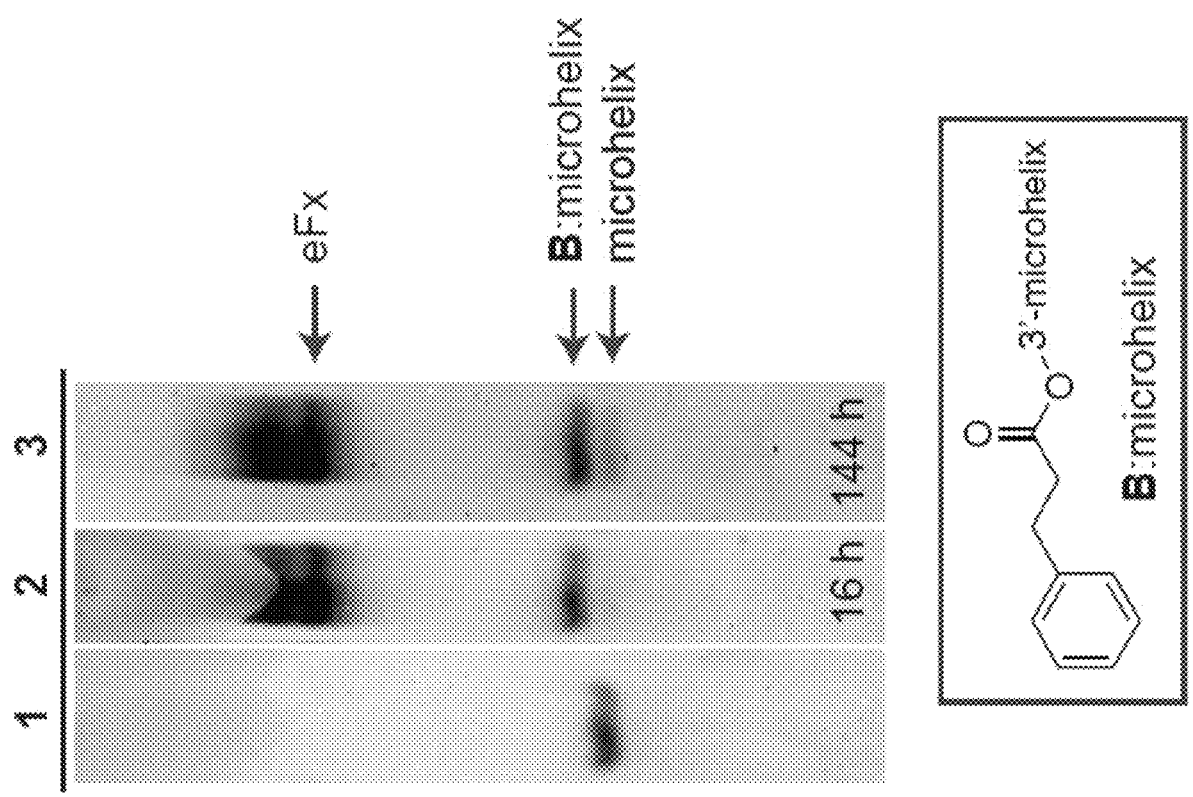
FIG. 14. Undesired hydrolysis of acylated microhelix. The microhelix charged by PhPA (B) was acylated at 16 h in a 100% yield, however, the acylation yield was found to decrease (76%) at 144 h, presumably because of unwanted hydrolysis by water on the ester linkage. Lane 1: microhelix; lane 2 and 3: crude acylated product observed at 16 h and 144 h, respectively. We limited the reaction time to 120 h based on this observation.

First, we determined the acylation efficiency of A to a small tRNA mimic, microhelix tRNA (mihx, 22 nt) by eFx using the previously reported standard acylation conditions (pH 7.5, 0° C.)[62] (FIG. 9a, top panel). Analysis of the reaction mixture by denaturing acidic polyacrylamide gel electrophoresis (PAGE) indicated that 67% of mihx was acylated with A (FIG. 9b, lane 1). With this benchmark established, we then screened substrate-eFx compatibility of the five substrates. eFx successfully acylated mihx with B in 77% yield, indicating that an amine functional group is not required for aminoacylation (FIG. 9b, lane 2). Moving further from the Phe structure proved difficult, as α,β-unsaturated substrate C was incompatible for mihx acylation via flexizyme under standard reaction conditions (FIG. 9b, lane 3). However, as we increased reaction pH and time (pH 7.5 to pH 8.8 and 16 h to 120 h, see FIGS. 13 and 14 for full details), mihx acylation with C improved yielding 44% and 74% after 16 and 120 h, respectively (FIG. 9b, lanes 6, 7). Notably, the newly established pH of 8.8 increased the yields for A and B to 82% and 100%, respectively (FIG. 9b, lanes 4, 5). Although to a minor extent, D and E were also acylated to the mihx in 16% and 40% yield, respectively (FIG. 9b, lane 8, 9). As expected, the aliphatic substrate F was not charged to the mihx by eFx, as the substrate does not contain an aryl group for substrate recognition by eFx (FIG. 9b, lane 10). However, changing the substrate's leaving group from CME to ABT and employing aFx in place of eFx enabled charging of the same aliphatic substrate G in 55% yield after 120 h (FIG. 9b, lane 11). Hence, using the newly established acylation conditions and utilizing the appropriate leaving group and Fx, all five substrates are successfully charged to the tRNA mimic.

Figure 10:
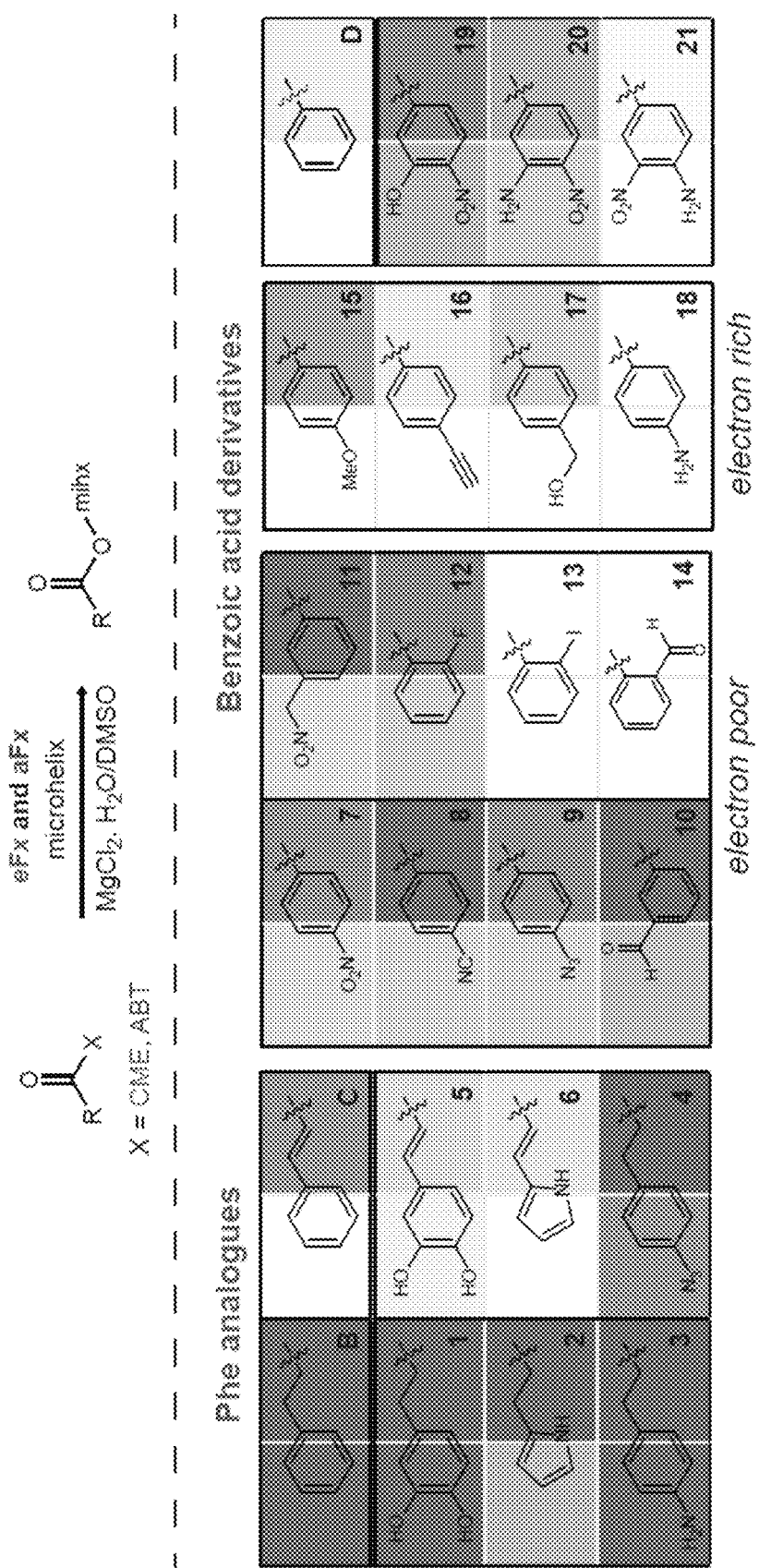
FIG. 10. Expanding the Fx substrate scope to analogues with various scaffolds. The range of noncanonical substrates compatible with Fx was further extended on four different monomer structure (Phe analogues, benzoic acid derivatives, heteroaromatic and aliphatic substrates). eFx and aFx charge a substrate by recognizing an aryl group of the substrate. The acylation reactions were performed using the microhelix RNA (22 nt) with the cognate Fx (eFx:45 nt, aFx:47 nt) and monitored over 120 h at two different pHs (7.5 vs. 8.8). Reaction condition: 50 mM HEPES (pH 7.5) or bicine (pH 8.8), 60 mM MgCl2, 1 µM microhelix, 5 µM Fx, and 5 mM substrates in 20% (v/v) DMSO solution. All acylation heat maps are shaded by percent conversion of microhelix. See FIG. 15 for the numerical values of acylation.
Figure 10:
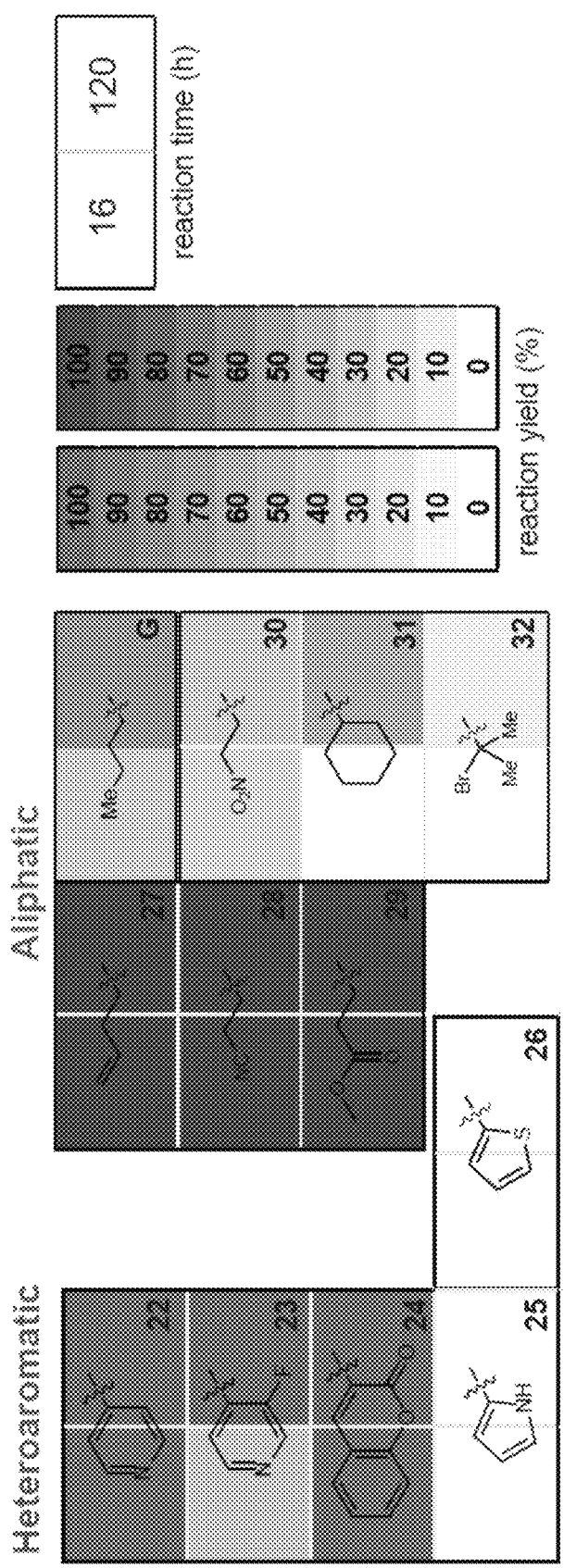

Next, we sought to further expand the substrate scope by elaborating the scaffolds of B, C, D, and G, to teach us about permissible substrates. Not only substrates that could be used by the Fx system, but also, later, the ribosome (see below). For this, we determined the mihx-acylation efficiency of eFx and aFx with four sets of scaffold analogues: Phe analogues harboring saturated and unsaturated aliphatic scaffolds with an aryl group, benzoic acid derivatives with a variety of functional groups, heteroaromatic scaffolds with different electronic properties, as well as aliphatic scaffolds with various steric hindrances (FIG. 10).

To investigate saturated and unsaturated aliphatic scaffolds containing an aryl group, we explored Phe analogues derived to bear a variety of functionalities (1-6) from the Fx substrates B and C.

Figure 16:
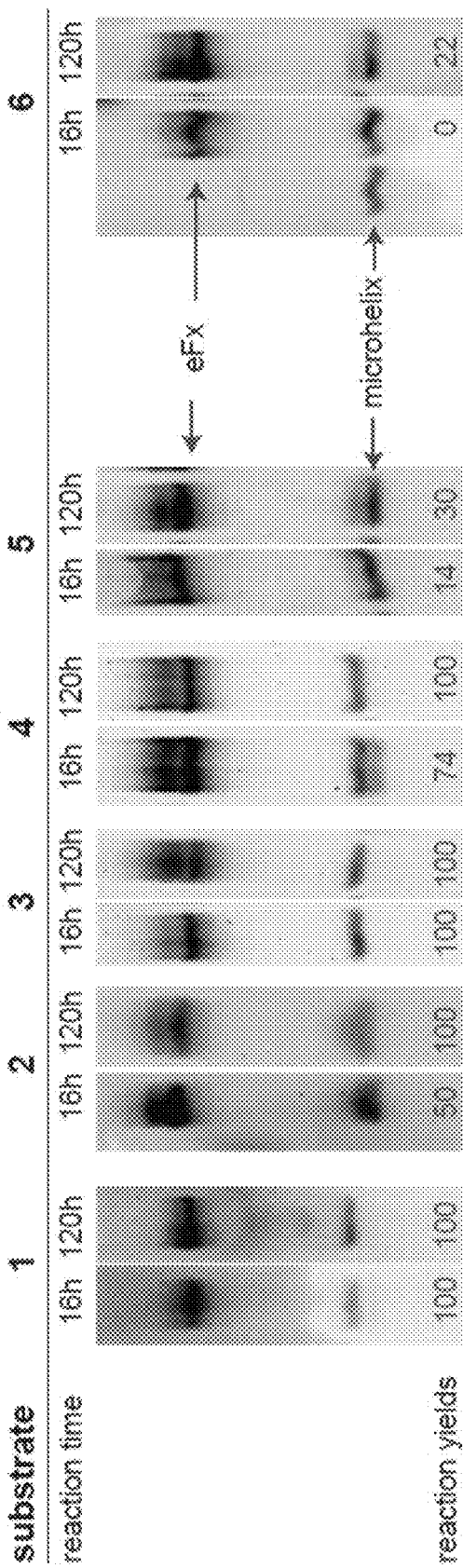
FIG. 16. Analysis of acylation with 1-6. The acylation yields were analyzed by electrophoresis on 20% polyacrylamide gel containing 50 mM NaOAc (pH 5.2). The crude products containing the chemical substrates (1-6) were loaded on the gel and separated by the electrophoretic mobility at 135 mV in cold room over 2-3 h. The reactions were monitored over 120 h and the yields were quantified using densiometric analysis (software: ImageJ).

Under optimal conditions, the substrates 1-4 were charged to the mihx by eFx in yields of 50-100% after 16 h and 100% after 120 h (FIGS. 15 and 16). Substrate 5 and 6 containing α,β-unsaturated scaffolds showed similar yield to their parent structure C. Both were charged by eFx at lower efficiencies (30% and 22% yield, respectively) than the saturated substrates, likely due to their increased structural rigidity hindering interaction with the Fx binding pocket.

Figure 17:
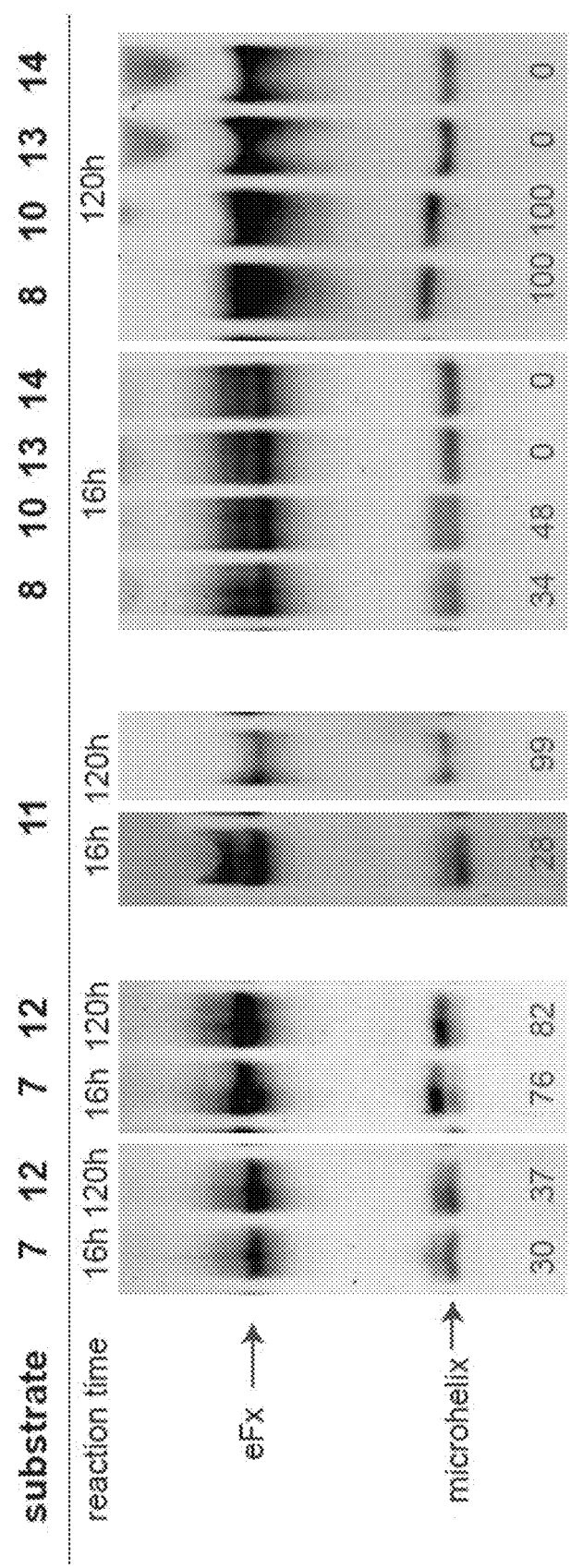
FIG. 17. Analysis of acylation with 7-21. The crude acylation reaction mixtures charged with the substrates (7-21) were analyzed by using the same methods described in FIG. 16.
Figure 17:
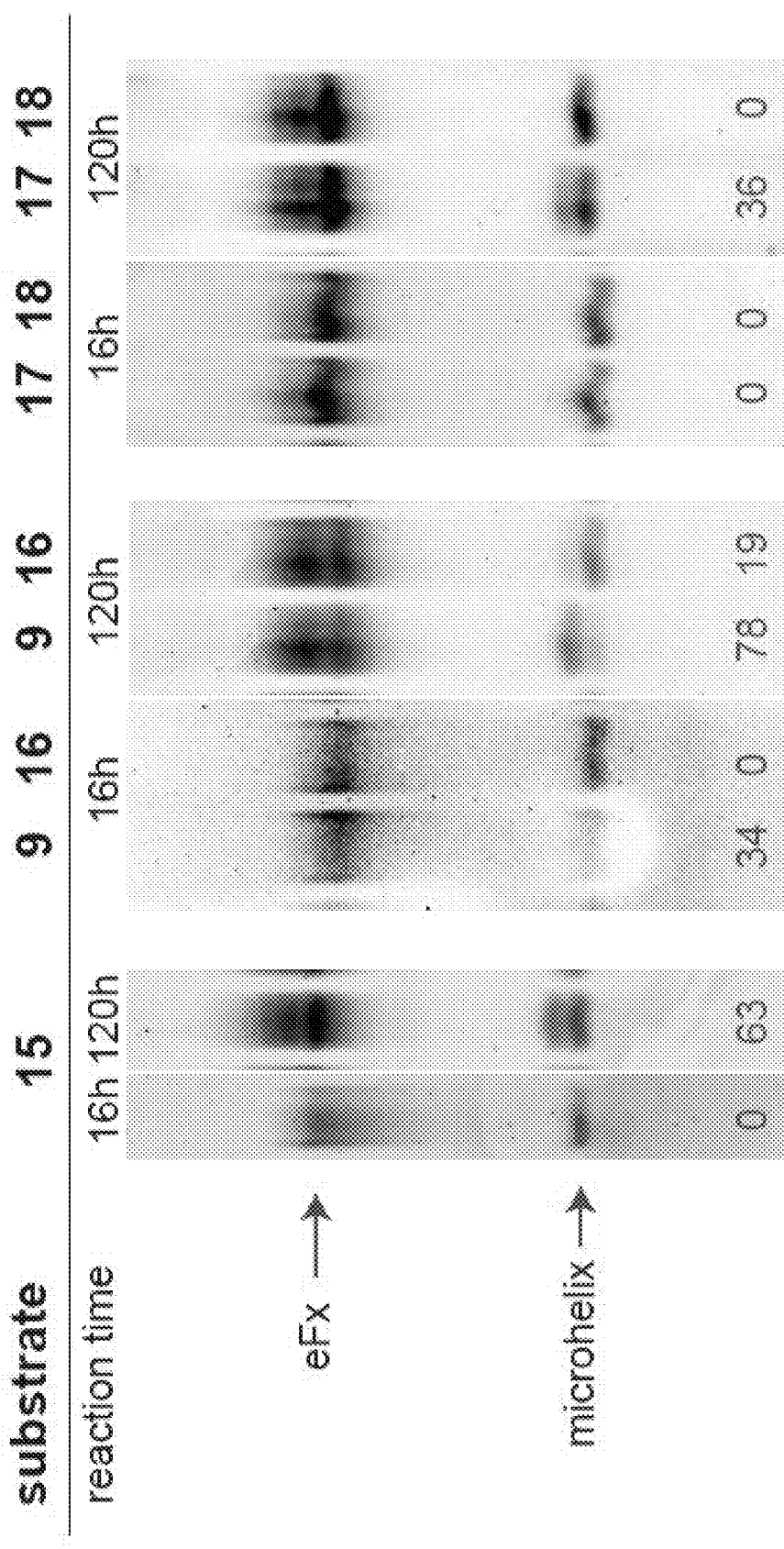
Figure 17:
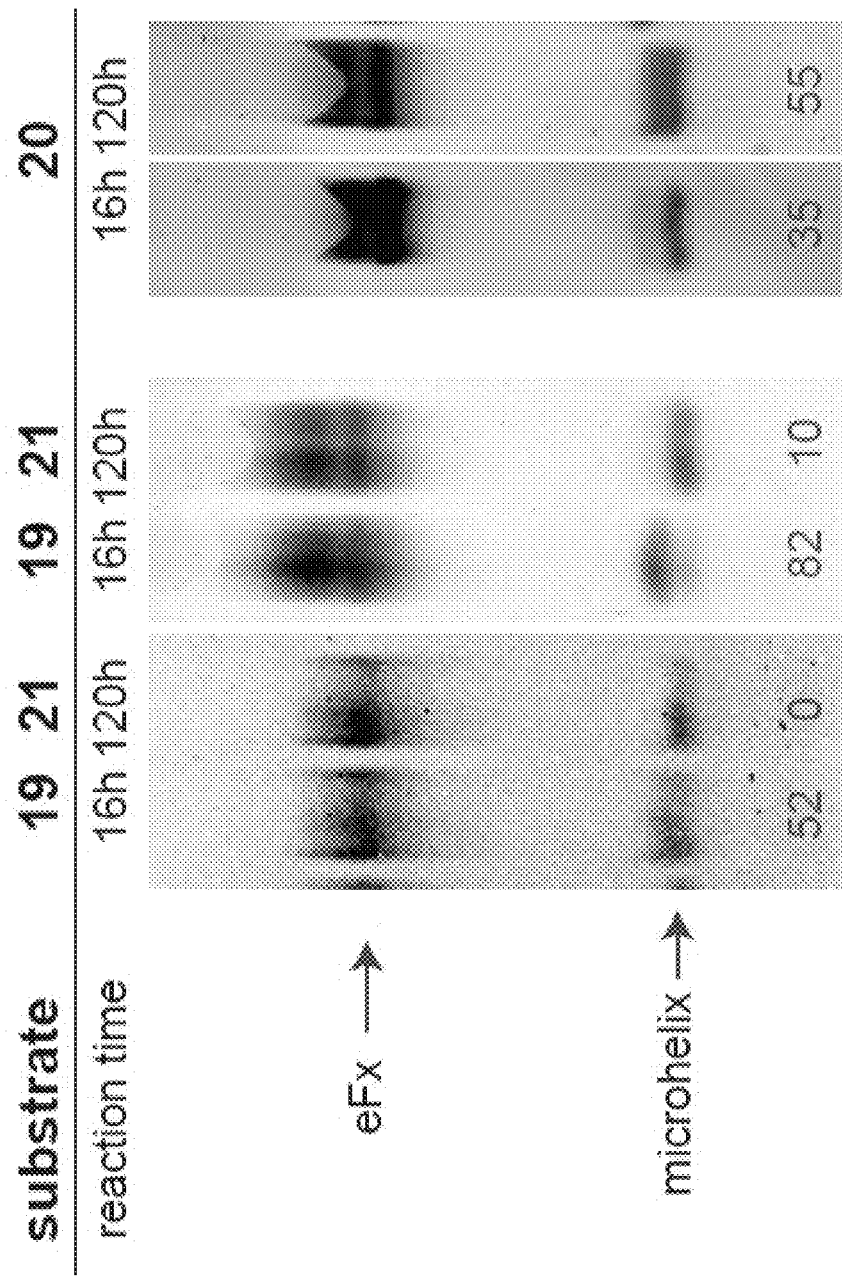
Figure 18:
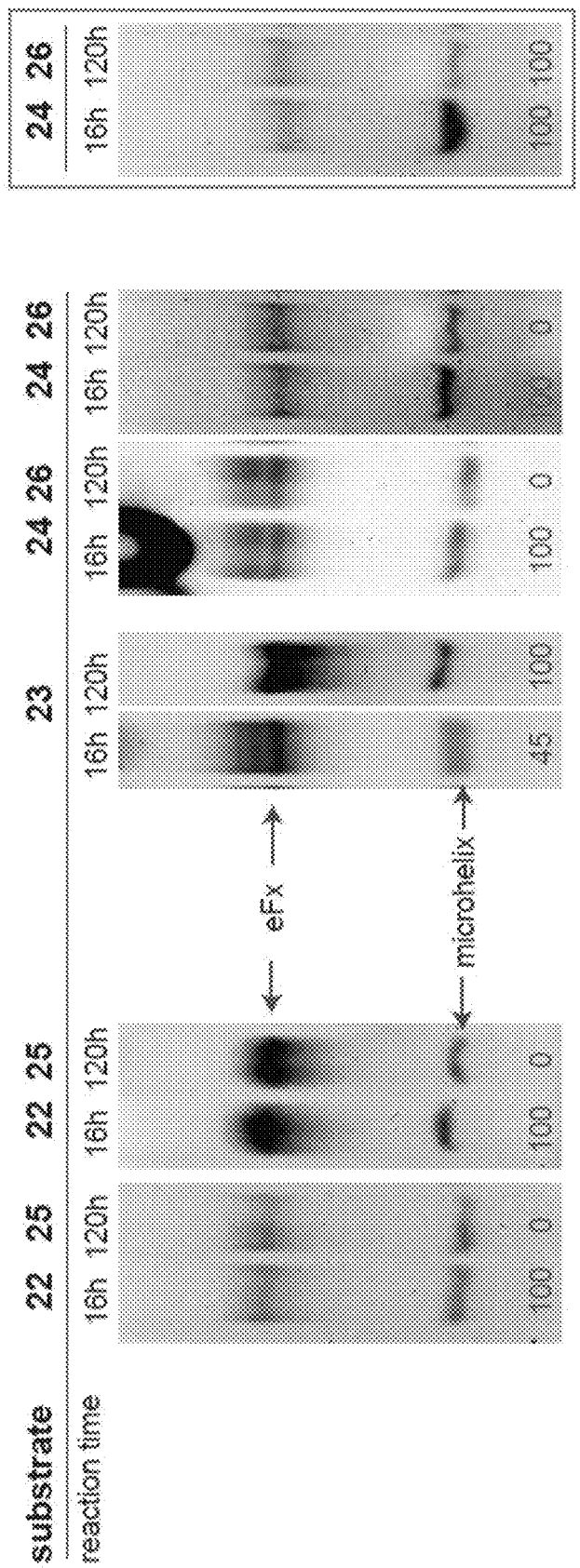
FIG. 18. Analysis of acylation with 22-32. The crude products charged with the chemical substrates (22-32) were analyzed. Gels were visualized by staining with GeRed (Biotium) and exposing on a filter of 630 nm for 20 s on a Gel Doc XR+ (Bio-Rad). The band containing the mihx charged with coumarin (24) in the orange box shows relatively higher intensity than the other nucleic acid bands when the gel is exposed in lower wavelength (560 nm). Note that the yields were obtained from the reaction with the substrate containing an CME and ABT leaving group, respectively. (coumarin excitation/emission wavelength: 380 nm/410-470 nm)
Figure 18:
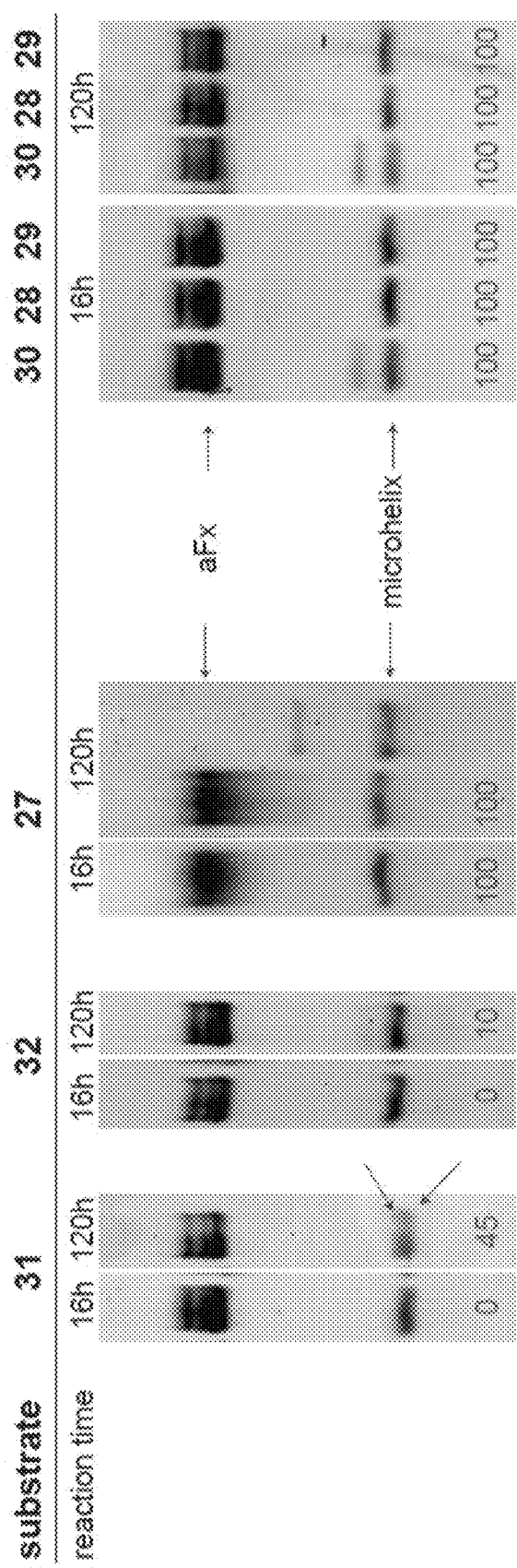

To further understand the substrate compatibility of eFx toward benzoic acid (D), we prepared a series of derivatives with altering electronic character (electron-poor: 7-14, electron-rich: 15-18) as well as substituent position (ortho, meta, para), performed Fx-catalyzed acylation reactions, and determined the acylation efficiency by acid denaturing PAGE and densiometric analysis (FIGS. 15, 17, and 18). For p-nitro-substituted substrate (7), determined acylation yield of eFx were 30% yield after 16 h and 76% after 120 h, and for unsubstituted substrate (D) 0% at 16 h, 16% at 120 h.

Similarly, high yields (28-48% at 16 h, 78-100% at 120 h) were observed for the electron-poor substrates (8-11) bearing a p-nitrile, p-azide, m-formyl group, and m-nitromethyl group, respectively. In contrast, the substrate with moderate electron-donating groups such as p-methoxy (15), p-ethynyl (16), and p-hydroxymethyl (17) showed lower reaction rate; no acylation was observed after 16 h and only with moderate yields after 120 h (19-63%). We observed no conversion after 120 h for electron-rich p-amino substrate 18. These results indicate a significant electronic effect; reaction rates generally increased for electron-poor substrates and decreased for electron-rich substrates.

Figure 19:
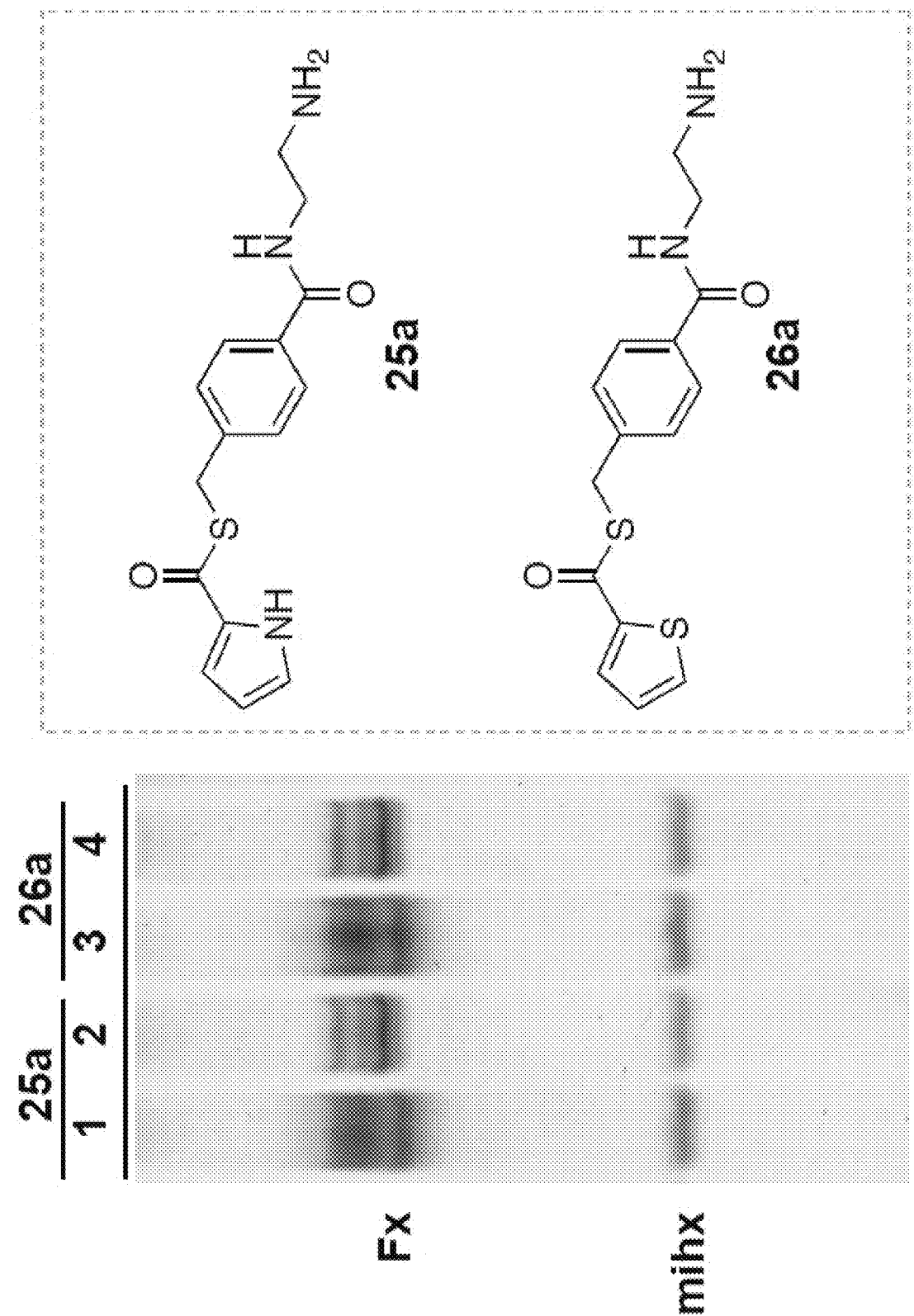
FIG. 19. Acylation test of pyrrole-ABT and thiophene-ABT. We tested additional substrates for the pyrrole and thiophene substrates (25a and 26a with ABT) in case that eFx did not recognize the small aromatic ring. However, we were not able to find a new band for substrate-charged microhelix in the gel. eFx and aFx was used for lane 1, 3 and 2, 4, respectively. (NMR spectroscopic data was generated but is not presented here).

We tested this hypothesis by installing an electron-withdrawing nitro-group at the meta position of the poor Fx substrate, 18, leading to substrate 21. As predicted, a slight improvement of 10% yield was observed after 120 h. Swapping the substituent pattern leading to substrate 20 (p-nitro and m-amine) further improved the reaction efficiency to 55% yield after 120 h, supporting the reactivity trend based on electronic character. In addition, we observed that ortho-substituted tolerance was governed by steric effects as o-fluoro 12 resulted in 82% yield after 120 h, while substrates with larger ortho substituents (o-iodo 13, o-formyl 14) were not charged to the mihx. The correlation between electronic character and Fx-catalyzed acylation was further confirmed by investigating the electron-poor heteroaromatic substrates pyridine 22, fluoro-pyridine 23, and coumarin 24. All three substrates were charged with high yields (45-100% at 16 h and 100% at 120 h) following the electronic trend. In contrast, five-membered electron-rich heteroaromatic substrates (pyrrole 25, 25a and thiophene 26, 26a; see FIG. 19 for 25a and 26a) did not show any reactivity in the Fx-catalyzed tRNA acylation reaction.

Finally, we investigated the substrate compatibility of aFx by exploring its catalytic activity toward aliphatic variants derived from its substrate G. We found that straight chain aliphatic acids are highly favored substrates; alkenyl (27), cyano (28) and ester (29) analogues were charged with 100% yield after 16 h. Nitroalkane (30) was a competent substrate, albeit in diminished yield (25%, 16 h and 30%, 120 h). In contrast, sterically hindered cyclohexyl (31) were charged at a slower rate (30% yield, 120 h). Moreover, bromopropane (32) was charged to only 10% after 120 h, indicating that increased steric bulk further decreases Fx-catalyzed acylation.

In summary, from the 38 tested analogues, 32 hitherto unknown Fx substrates were identified, significantly expanding the scope of the Fx-catalyzed aminoacylation reaction. Based on their molecular characteristics and efficiencies in Fx-catalyzed acylation, general design rules for potential Fx substrates are deduced with greatest success for: i) higher structural similarity to Phe for eFx, ii) electron-decreasing characteristics from the carbonyl region, and iii) less steric hindrance at the acylation site.

Figure 11:
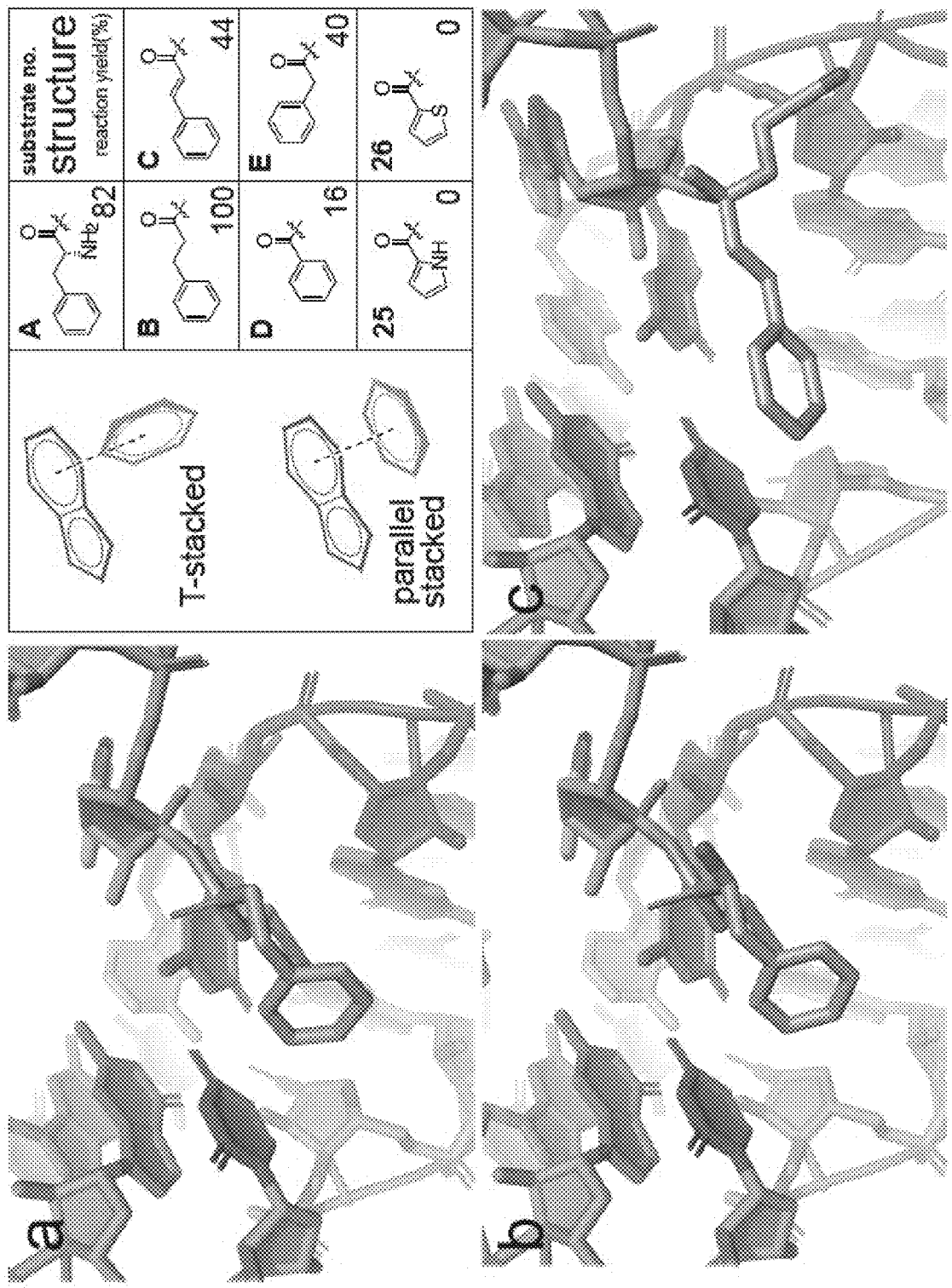
FIG. 11. Simulated molecular interactions between selected substrates and the binding pocket of eFx. Tetrahedral intermediate models of the CME esters were optimized and subjected to Monte Carlo energy optimization via Rosetta. a) Phe (A), b) hydrocinnamic acid (B), c) cinnamic acid (C), d) benzoic acid (D), e) phenylacetic acid (E); dark yellow. No strong interaction with the guanine residue is observed for f) pyrrole-2-carboxylic acid (25) and g) 2-thiophenecarboxylic acid (26).
Figure 11:
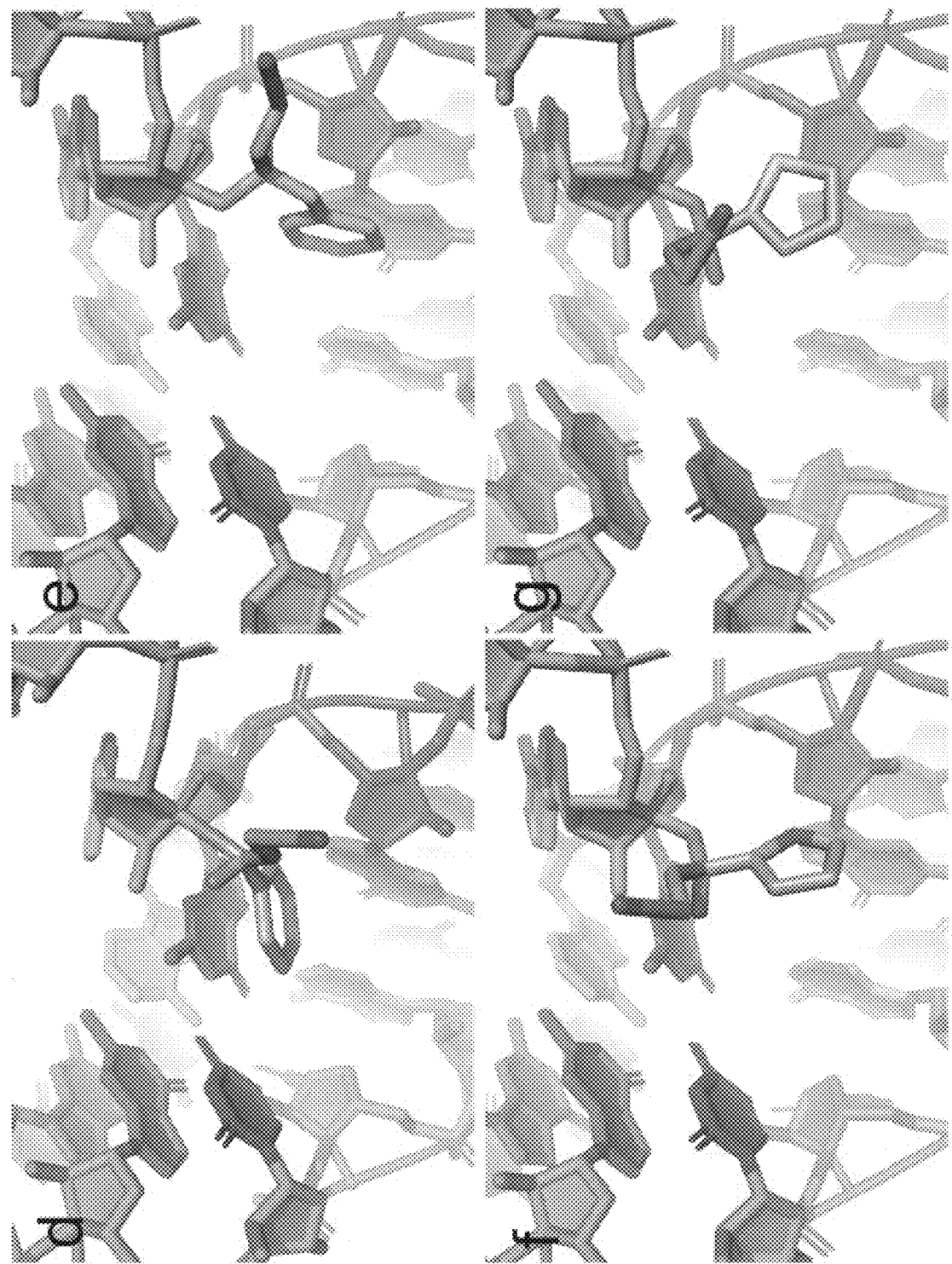

To gain further insights about possible constraints for using flexizyme to charge noncanonical chemical substrates onto tRNAs, we next used computational modeling to better understand our data. A previous crystallographic study[56] suggests that when an aromatic amino acid such as Phe is charged by Fx, the phenyl ring of the substrate stacks against the terminal J1a/3 base pair of Fx. Notably, the structure as crystallized (PDB: 3CUL and 3CUN) contains only residual density for a phenylalanyl-ethyl ester ligand, which is suggestive of a possible location for substrate conformation at the active site. To elucidate the molecular interaction of substrates in the binding pocket of Fx, using Rosetta[63], we generated models (data not shown) of the tetrahedral intermediates formed with tRNA by five representative substrates (A-E) as well as pyrrole-2-carboxylic acid (25, 25a) and 2-thiophenecarboxylic acid (26, 26a) that gives no acylation yield on Fx-catalysis (FIG. 11). The modeling supports either T-stacked interaction for Phe and hydrocinnamic acid (B) or parallel stacked interactions for cinnamic acid (C), benzoic acid (D), and phenylacetic acid (E). In contrast, pyrrole and thiophene groups are unable to form particularly favorable interactions with the terminal J1a/3 base pair. The absence of these interactions may explain our empirical observation that 25, 25a and 26, 26a containing an electron-rich heteroaromatic group are poor substrates for eFx.

The Novel Fx Substrates are Charged to tRNAs and Incorporated into Peptides.

Figure 12:
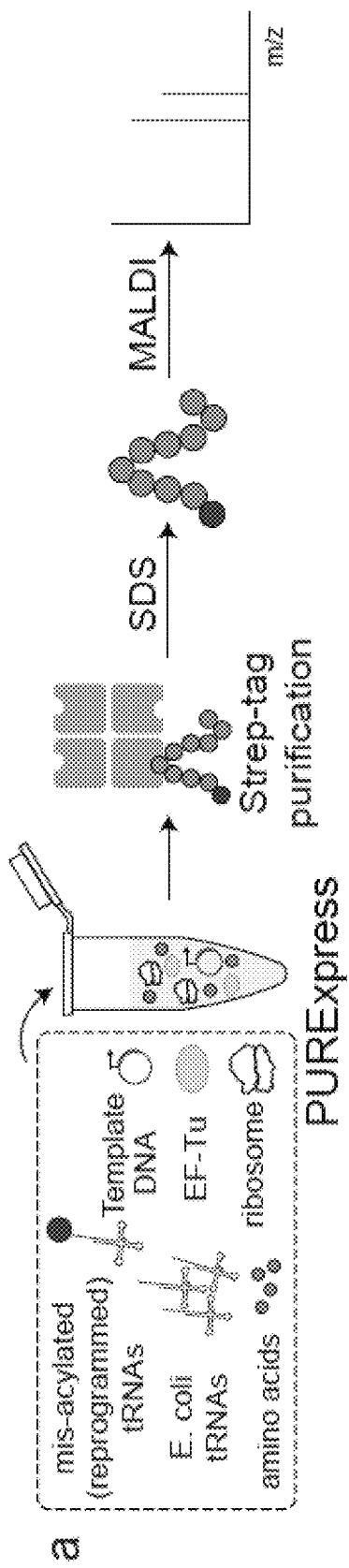
FIG. 12. Ribosomal synthesis of N-terminal functionalized peptides with noncanonical substrates. a) Schematic overview of peptide synthesis and characterization. N-terminal functionalized peptides were prepared in the PUREexpress™ system by using Fx-charged tRNA$^{fMet}$, purified via the Strep tag, denatured with SDS, and characterized by MALDI mass spectrometry. b) Mass spectrum of the peptide in the presence of all 20 natural amino acids and absence of Fx-charged tRNA. c) Mass spectrum of the peptide in the absence of methionine and Fx-charged tRNA. d-i) Mass spectra of peptides with N-terminally incorporated noncanonical substrates. *: A minor amount of peptide containing phenylalanine at the N-terminus was found to be unformylated. $NH_2$-FWSHPQFEKST-OH (SEQ ID NO:14); [M+Na]+=1415, A: phenylalanine, B: hydrocinnamic acid, C: cinnamic acid, D: benzoic acid, E: phenylacetic acid, G: propanoic acid.
Figure 12:
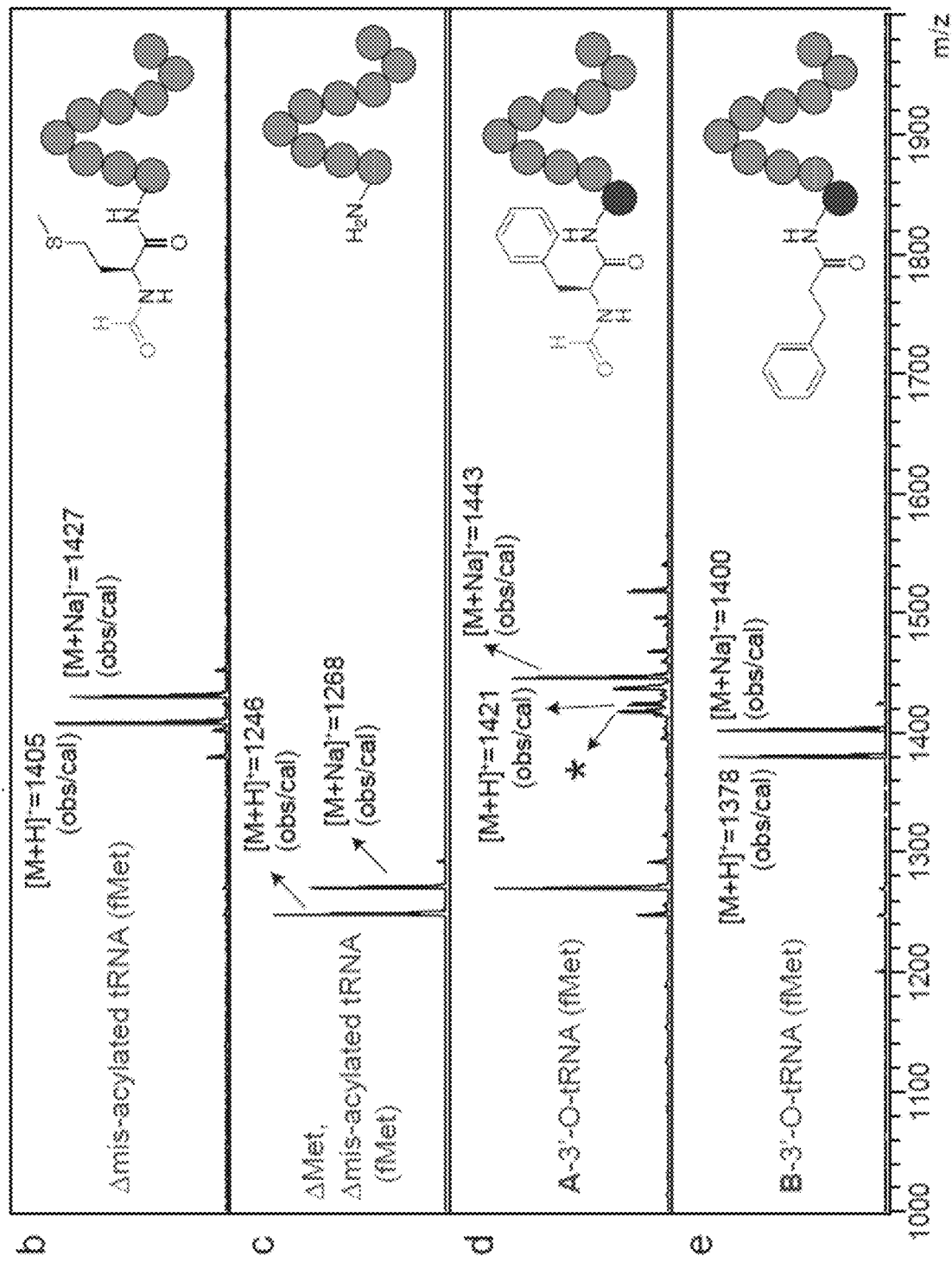
Figure 12:
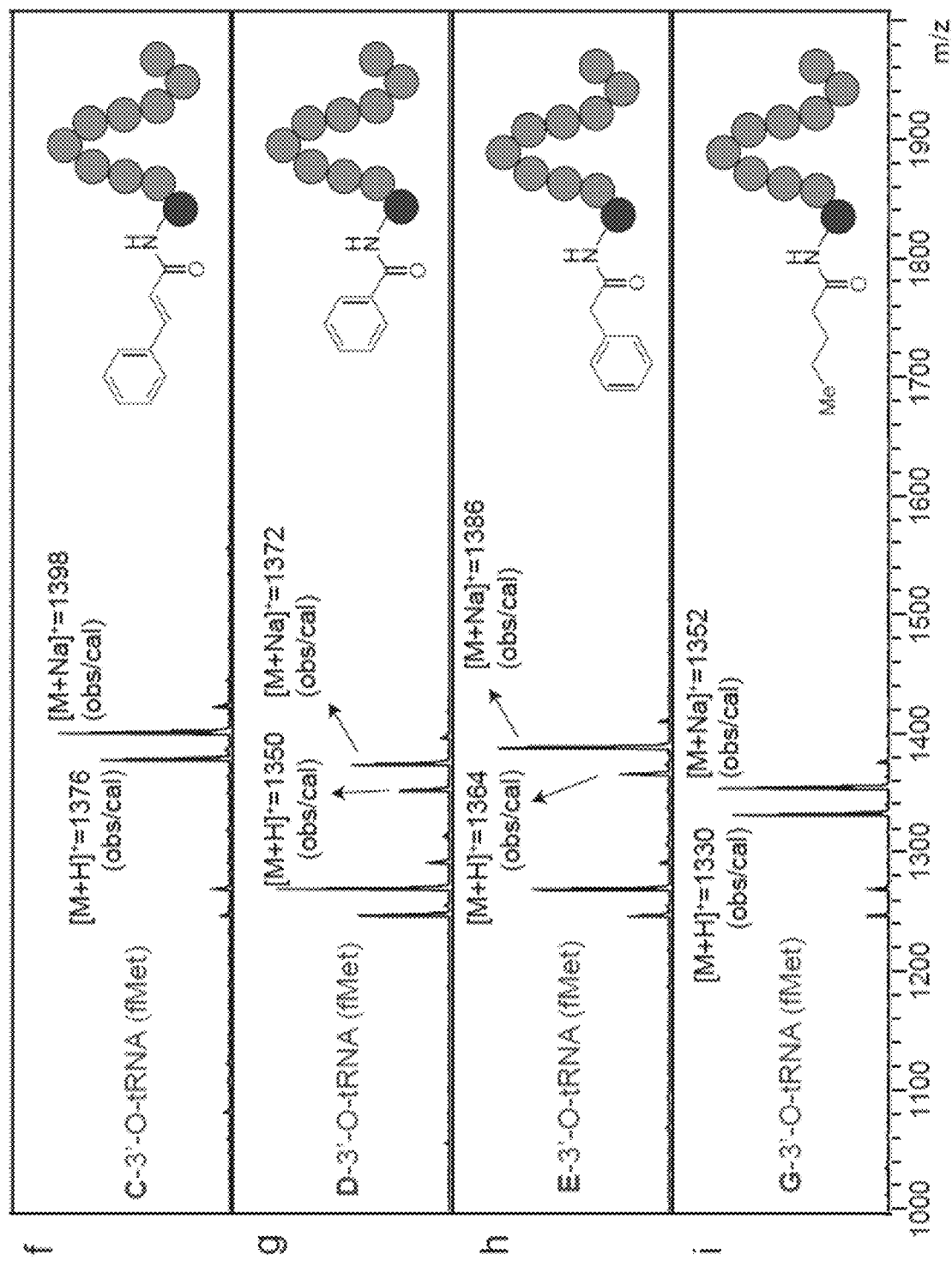

Next, we investigated whether the newly found Fx substrates that can be charged onto tRNAs are accepted by the natural protein translation machinery. Based on our optimized conditions, we performed Fx-catalyzed acylation reactions using Fx-optimized tRNAs[62] instead of the mihx. Then, we purified the tRNA-monomers and added them to a cell-free protein synthesis reaction, allowed translation to proceed, and determined the incorporation of the new substrates into a small reporter peptide by MALDI-TOF mass spectrometry (FIG. 12 and data not shown).

Initially, we attempted to use a well-established crude extract-based *Escherichia coli* cell-free protein synthesis (CFPS)[34, 64-67] which is capable of high-level incorporation of noncanonical amino acids. However, we were not able to characterize the reporter peptide, presumably because active peptidases in the extract digested the peptide. In order to circumvent possible undesired degradation, we turned to the commercially available (Protein synthesis Using Recombinant Elements) PURExpress™ system[68]. The PURExpress™ system contains the minimal set of components required for protein translation, thereby minimizing any undesired peptide degradation, and allows addition of custom sets of amino acids and tRNAs of interest.

Previous works from the Suga lab, among others, have shown this platform to be suitable for assessing peptide synthesis[69], especially for N-terminal incorporation of non-canonical monomers[25, 60]. As a reporter peptide, we designed a T7 promoter-controlled DNA template (pJL1_StrepII) encoding the translation initiation codon AUG for N-terminal incorporation of the novel Fx substrates, a Streptavidin (Strep) tag and a Ser and Thr codon (XMWHSPQFEKST (SEQ ID NO:15) (strep-tag: italicized), and where X indicates the position of the novel Fx substrate, for details, see SI). Peptide synthesis was performed using only the 9 amino acids that decode the initiation codon AUG and the purification tag (data not shown). We excluded the other 11 amino acids to prevent corresponding endogenous tRNAs from being aminoacylated and used in translation, thereby, eliminated competition between endogenous tRNAs and Fx-charged tRNAs during peptide synthesis. For this, PURExpress™ reactions were incubated at 37° C. for 4 h. The synthesized peptides were then purified using Strep-Tactin®-coated magnetic beads (IBA), denatured with SDS, and characterized by MALDI-TOF mass spectroscopy (FIG. 12a).

As a positive control experiment, we prepared a peptide in the presence of all 20 natural amino acids and absence of any Fx-charged tRNA, so that the reporter mRNA would be translated into MWHSPQFEKST (SEQ ID NO:16) according to the standard genetic code. Indeed, we detected two major peaks corresponding to the theoretical mass of the peptide ions. The Met residue at the N-terminus was found to be formylated (fM) (fMWHSPQFEKST, SEQ ID NO:17) by a formylase present in the PURE system[70]; [M+H]+ =1405 (observed, obs), 1405 Da (calculated, cal), [M+Na]+ =1427 (obs), 1427 Da (cal) (FIG. 12b).

As a negative control experiment, we performed a PURExpress™ reaction in the presence of only 9 amino acids encoding the residues downstream of the initiating codon (W, S, H, P, Q, F, E, K, and T); no Met or mis-acylated tRNAfMet was added to the reaction mixture. The MALDI spectrum shows only a single species for the synthesized peptide giving a mass of 1246 ([M+H]+) and 1268 Da ([M+Na]+) (FIG. 12c). The observed peaks correspond to the theoretical mass of a peptide with sequence WHSPQFEKST (SEQ ID NO:18), indicating that translation initiation can occur on the succeeding mRNA codon if the amino acid for the initiating codon is not present in CFPS system, a phenomenon previously reported[71].

For incorporation of the noncanonical substrates (B-E, and G) at the start codon, we used the tRNA$^{fMet}$ containing the CAU anticodon, corresponding to the AUG codon on the mRNA and charged all five substrates onto the tRNA separately. The same amount of precipitated tRNA containing a mixture of substrate-charged/uncharged tRNA was added to the PURExpress' reaction. Methionine was not added to the reaction so as to avoid the incorporation of Met at the start codon by Met-charged endogenous tRNA$^{fMet}$ produced in the PURE system. We discovered that all the peaks found in the MALDI spectra corresponded to a theoretical mass of peptide that contains the substrate on the N-terminus (FIG. 12d-i). It is notable that N-terminal Trp was found to be unformylated (FIG. 12c) in comparison with that the N-terminal Met in FIG. 12b, which was found to be completely formylated. The N-terminus Phe (FIG. 12d) was found to with formylation (f) and without formylation (F), suggesting that a larger side chain may prohibit the formylase from efficiently formylating the residue.

We carried out the same acylation reaction onto a tRNA$^{fMet}$ for the other noncanonical substrates (B-G and 1-32, except for the 6 substrates that showed no acylation; F, 13, 14, 18, 25, and 26) and subsequently synthesized 32 different peptides with each substrate on the N-terminus, indicating all the noncanonical substrates were incorporated into a peptide. MALDI spectra were generated for the purified peptide (data not shown). The substrates with higher acylation yields tend to show higher translation efficiency (data not shown), representing the concentration of mis-acylated tRNA is a limiting factor for the translation. To more rigorously characterize the N-terminal peptides, we additionally quantified peptide yields (data not shown). These data support our hypothesis that the system is limited by mis-acylated tRNA.

Ribosome-mediated polymerization of alternative A-B polycondensation reactions (i.e., non-ester and non-amide bonds) may offer new classes of sequence-defined polymers. Using a mis-acylated tRNA$^{GluE2}$(GGU) recognizing an ACC codon (Thr) on the mRNA, we tested incorporation of a few substrates at the C-terminus of a peptide, which would require formation of a covalent carbon-carbon bond. Unfortunately, our attempt to produce a biopolymer with such a bond was unsuccessful.

Conclusion

In this work, we set out to systematically expand the range of chemical substrates for translation though the identification of design rules for flexizyme-mediated charging of noncanonical monomers to tRNAs. Beyond commonly used amino- and hydroxy-acids, we showed that a diverse repertoire of substrates built from elaborating upon phenylalanine, benzoic acid, heteroaromatic, and aliphatic scaffolds could be acylated to tRNAs. Our rational approach to scaffold design allowed us to better identify design rules for using flexizymes to charge novel monomers onto tRNA. We found, as expected, that substrates that look more like phenylalanine are favorable for Fx catalyzed acylation reactions. We also found new guiding principles, for examples, that electron-poor substrates are favored over electron rich, and certain bulky groups are poorly not well tolerated near the acylation site. Additionally, by investigating the molecular interaction of key substrates in the binding pocket of flexizyme using computational modeling, we found that either T-stacked or parallel-stacked interactions seem to be key features that enable charging by flexizyme. Beyond these design rules, we also showed that tRNA-monomers from our expanded substrates successfully yield a wide variety of N-functionalized peptides in a PURExpress™ system through genetic code reprogramming. This is important because our data joins an emerging number of studies showing that the ribosome is capable of polymerizing a wide array of substrates, especially at the N-terminus. While the production of novel N-terminal peptides themselves was not our focus, they might be used directly by others in the field in multiple ways. For example, the peptides containing 4 and 27 at the N-terminus have the potential to combine the advantages of synthetic polymers and sequence-defined peptides by chemically attaching a molecule with a polymerizable unit, which could lead to novel hybrid materials. Looking forward, we anticipate that our work will enable the design and selection of new classes of noncanonical monomers for use in translation. For example, the monomers we describe also begin the march towards novel classes of sequenced defined polymers that are not polyesters or polyamides, perhaps even those with carbon-carbon bonds. However, since the shape, physiochemical, and dynamic properties of the ribosome and its active site have been evolutionarily optimized to operate with proteins built of ~20 canonical amino acids, such advances will need to be supported by additional efforts in engineering the translation apparatus[72,73].

REFERENCES

1. Edelmann, P. & Gallant, J. Mistranslation in *E. coli*. *Cell* 10, 131-137 (1977).
2. Precup, J., Ulrich, A. K., Roopnarine, O. & Parker, J. Context specific misreading of phenylalanine codons. *Mol Gen Genet* 218, 397-401 (1989).
3. Rodnina, M. V. & Wintermeyer, W. Fidelity of aminoacyl-tRNA selection on the ribosome: kinetic and structural mechanisms. *Annu Rev Biochem* 70, 415-435 (2001).
4. Cropp, T. A., Anderson, J. C. & Chin, J. W. Reprogramming the amino-acid substrate specificity of orthogonal aminoacyl-tRNA synthetases to expand the genetic code of eukaryotic cells. *Nature Protocols* 2, 2590-2600 (2007).
5. Morimoto, J., Hayashi, Y., Iwasaki, K. & Suga, H. Flexizymes: their evolutionary history and the origin of catalytic function. *Acc Chem Res* 44, 1359-1368 (2011).
6. Albayrak, C. & Swartz, J. R. Cell-free co-production of an orthogonal transfer RNA activates efficient site-specific non-natural amino acid incorporation. *Nucleic Acids Res* 41, 5949-5963 (2013). 7. Chin, J. W. Expanding and reprogramming the genetic code. *Nature* 550, 53-60

(2017). 8. Mukai, T., Lajoie, M. J., Englert, M. & Soll, D. Rewriting the genetic code. *Annu Rev Microbiol* 71, 557-577 (2017).

9. Voller, J. S. & Budisa, N. Coupling genetic code expansion and metabolic engineering for synthetic cells. *Curr Opin Biotech* 48, 1-7 (2017).

10. Vargas-Rodriguez, O., Sevostyanova, A., Soll, D. & Crnkovic, A. Upgrading aminoacyltRNA synthetases for genetic code expansion. *Curr Opin Chem Biol* 46, 115-122 (2018).

11. Arranz-Gibertt, P., Vanderschurent, K. & Isaacs, F. J. Next-generation genetic code expansion. *Curr Opin Chem Biol* 46, 203-211 (2018).

12. Tajima, K., Katoh, T. & Suga, H. Genetic code expansion via integration of redundant amino acid assignment by finely tuning tRNA pools. *Curr Opin Chem Biol* 46, 212-218 (2018).

13. Rogers, J. M. & Suga, H. Discovering functional, non-proteinogenic amino acid containing, peptides using genetic code reprogramming. *Org Biomol Chem* 13, 9353-9363 (2015).

14. Obexer, R., Walport, L. J. & Suga, H. Exploring sequence space: harnessing chemical and biological diversity towards new peptide leads. *Curr Opin Chem Biol* 38, 52-61 (2017).

15. Fujino, T., Goto, Y., Suga, H. & Murakami, H. Ribosomal synthesis of peptides with multiple beta-amino acids. *J Am Chem Soc* 138, 1962-1969 (2016).

16. Ohshiro, Y. et al. Ribosomal synthesis of backbone-macrocyclic peptides containing gamma-amino acids. *Chem Bio Chem* 12, 1183-1187 (2011).

17. Goto, Y., Murakami, H. & Suga, H. Initiating translation with D-amino acids. *RNA* 14, 1390-1398 (2008).

18. Katoh, T., Tajima, K. & Suga, H. Consecutive elongation of D-amino acids in translation. *Cell Chem Biol* 24, 46-54 (2017).

19. Kawakami, T., Ishizawa, T. & Murakami, H. Extensive reprogramming of the genetic code for genetically encoded synthesis of highly N-alkylated polycyclic peptidomimetics. *J Am Chem Soc* 135, 12297-12304 (2013).

20. Iwane, Y. et al. Expanding the amino acid repertoire of ribosomal polypeptide synthesis via the artificial division of codon boxes. *Nat Chem* 8, 317-325 (2016).

21. Terasaka, N., Iwane, Y., Geiermann, A. S., Goto, Y. & Suga, H. Recent developments of engineered translational machineries for the incorporation of non-canonical amino acids into polypeptides. *Int J Mol Sci* 16, 6513-6531 (2015).

22. Ohta, A., Murakami, H., Higashimura, E. & Suga, H. Synthesis of polyester by means of genetic code reprogramming. *Chem Biol* 14, 1315-1322 (2007).19

23. Ohta, A., Murakami, H. & Suga, H. Polymerization of alpha-hydroxy acids by ribosomes. *Chem Bio Chem* 9, 2773-2778 (2008).

24. Goto, Y. & Suga, H. Translation initiation with initiator tRNA charged with exotic peptides. *J Am Chem Soc* 131, 5040-5041 (2009).

25. Rogers, J. M. et al. Ribosomal synthesis and folding of peptide-helical aromatic foldamer hybrids. *Nat Chem* 10, 405-412 (2018).

26. Torikai, K. & Suga, H. Ribosomal synthesis of an amphotericin-B inspired macrocycle. *J Am Chem Soc* 136, 17359-17361 (2014).

27. Kawakami, T., Ogawa, K., Hatta, T., Goshima, N. & Natsume, T. Directed evolution of a cyclized peptoid-peptide chimera against a cell-free expressed protein and proteomic profiling of the interacting proteins to create a protein-protein interaction inhibitor. *ACS Chem Biol* 11, 1569-1577 (2016).

28. Kanter, G. et al. Cell-free production of scFv fusion proteins: an efficient approach for personalized lymphoma vaccines. *Blood* 109, 3393-3399 (2007).

29. Cho, H. et al. Optimized clinical performance of growth hormone with an expanded genetic code. *Proc Natl Acad Sci USA* 108, 9060-9065 (2011).

30. Axup, J. Y. et al. Synthesis of site-specific antibody-drug conjugates using unnatural amino acids. *Proc Natl Acad Sci USA* 109, 16101-16106 (2012).

31. Zimmerman, E. S. et al. Production of site-specific antibody-drug conjugates using optimized non-natural amino acids in a cell-free expression system. *Bioconjug Chem* 25, 351-361 (2014).

32. Raucher, D. & Ryu, J. S. Cell-penetrating peptides: strategies for anticancer treatment. *Trends Mol Med* 21, 560-570 (2015).

33. Despanie, J., Dhandhukia, J. P., Hamm-Alvarez, S. F. & MacKay, J. A. Elastin-like polypeptides: Therapeutic applications for an emerging class of nanomedicines. *J Control Release* 240, 93-108 (2016).

34. Martin, R. W. et al. Development of a CHO-based cell-free platform for synthesis of active monoclonal antibodies. *ACS Synth Biol* 6, 1370-1379 (2017).

35. Heckler, T. G. et al. T4 RNA ligase mediated preparation of novel "chemically misacylated" tRNAPheS. *Biochemistry* 23, 1468-1473 (1984).

36. Robertson, S. A., Noren, C. J., Anthony-Cahill, S. J., Griffith, M. C. & Schultz, P. G. The use of 5'-phospho-2 deoxyribocytidylylriboadenosine as a facile route to chemical aminoacylation of tRNA. *Nucleic Acids Res* 17, 9649-9660 (1989).

37. Robertson, S. A., Ellman, J. A. & Schultz, P. G. A general and efficient route for chemical aminoacylation of transfer RNAs. *J Am Chem Soc* 113, 2722-2729 (1991).

38. Kwiatkowski, M., Wang, J. F. & Forster, A. C. Facile synthesis of N-acyl-aminoacyl-pCpA for preparation of mischarged fully ribo tRNA. *Bioconjug Chem* 25, 2086-2091 (2014).

39. Wang, J. F., Kwiatkowski, M. & Forster, A. C. Ribosomal peptide syntheses from activated substrates reveal rate limitation by an unexpected step at the peptidyl site. *J Am Chem Soc* 138, 15587-15595 (2016).

40. Yamanaka, K., Nakata, H., Hohsaka, T. & Sisido, M. Efficient synthesis of non-natural mutants in *Escherichia coli* S30 in vitro protein synthesizing system. *J Biosci Bioeng* 97, 395-399 (2004).

41. Liu, D. R. & Schultz, P. G. Progress toward the evolution of an organism with an expanded genetic code. *Proc Natl Acad Sci USA* 96, 4780-4785 (1999).

42. Wang, L., Brock, A., Herberich, B. & Schultz, P. G. Expanding the genetic code of *Escherichia coli*. *Science* 292, 498-500 (2001).

43. Nozawa, K. et al. Pyrrolysyl-tRNA synthetase-tRNA (Pyl) structure reveals the molecular basis of orthogonality. *Nature* 457, 1163-1167 (2009).20

44. Hancock, S. M., Uprety, R., Deiters, A. & Chin, J. W. Expanding the genetic code of yeast for incorporation of diverse unnatural amino acids via a pyrrolysyl-tRNA synthetase/tRNA pair. *J Am Chem Soc* 132, 14819-14824 (2010).

45. Neumann, H., Slusarczyk, A. L. & Chin, J. W. De novo generation of mutually orthogonal aminoacyl-tRNA synthetase/tRNA pairs. *J Am Chem Soc* 132, 2142-2144 (2010).

46. Chin, J. W. Expanding and reprogramming the genetic code of cells and animals. *Annu Rev Biochem* 83, 379-408 (2014).
47. Ellefson, J. W. et al. Directed evolution of genetic parts and circuits by compartmentalized partnered replication. *Nat Biotechnol* 32, 97-101 (2014).
48. Schmied, W. H., Elsasser, S. J., Uttamapinant, C. & Chin, J. W. Efficient multisite unnatural amino acid incorporation in mammalian cells via optimized pyrrolysyl tRNA synthetase/tRNA expression and engineered eRF1. *J Am Chem Soc* 136, 15577-15583 (2014).
49. Amiram, M. et al. Evolution of translation machinery in recoded bacteria enables multi-site incorporation of nonstandard amino acids. *Nat Biotechnol* 33, 1272-1279 (2015).
50. Willis, J. C. W. & Chin, J. W. Mutually orthogonal pyrrolysyl-tRNA synthetase/tRNA pairs. *Nat Chem* 10, 831-837 (2018).
51. Saito, H. & Suga, H. A ribozyme exclusively aminoacylates the 3'-hydroxyl group of the tRNA terminal adenosine. *J Am Chem Soc* 123, 7178-7179 (2001).
52. Lee, N., Bessho, Y., Wei, K., Szostak, J. W. & Suga, H. Ribozyme-catalyzed tRNA aminoacylation. *Nat Struct Biol* 7, 28-33 (2000).
53. Murakami, H., Saito, H. & Suga, H. A versatile tRNA aminoacylation catalyst based on RNA. *Chem Biol* 10, 655-662 (2003).
54. Ramaswamy, K., Saito, H., Murakami, H., Shiba, K. & Suga, H. Designer ribozymes: programming the tRNA specificity into flexizyme. *J Am Chem Soc* 126, 11454-11455 (2004).
55. Murakami, H., Ohta, A., Ashigai, H. & Suga, H. A highly flexible tRNA acylation method for non-natural polypeptide synthesis. *Nat Methods* 3, 357-359 (2006).
56. Xiao, H., Murakami, H., Suga, H. & Ferre-D'Amare, A. R. Structural basis of specific tRNA aminoacylation by a small in vitro selected ribozyme. *Nature* 454, 358-361 (2008).
57. Passioura, T. & Suga, H. Flexizyme-mediated genetic reprogramming as a tool for noncanonical peptide synthesis and drug discovery. *Chemistry* 19, 6530-6536 (2013).
58. Niwa, N., Yamagishi, Y., Murakami, H. & Suga, H. A flexizyme that selectively charges amino acids activated by a water-friendly leaving group. *Bioorg Med Chem Lett* 19, 3892-3894 (2009).
59. Saito, H., Watanabe, K. & Suga, H. Concurrent molecular recognition of the amino acid and tRNA by a ribozyme. *RNA* 7, 1867-1878 (2001).
60. Goto, Y. et al. Reprogramming the translation initiation for the synthesis of physiologically stable cyclic peptides. *ACS Chem Biol* 3, 120-129 (2008).
61. Saito, H., Kourouklis, D. & Suga, H. An in vitro evolved precursor tRNA with aminoacylation activity. *EMBO J* 20, 1797-1806 (2001).
62. Goto, Y., Katoh, T. & Suga, H. Flexizymes for genetic code reprogramming. *Nat Protoc* 6, 779-790 (2011).
63. Das, R. & Baker, D. Macromolecular modeling with Rosetta. *Annu Rev Biochem* 77, 363-382 (2008).
64. Carlson, E. D., Gan, R., Hodgman, C. E. & Jewett, M. C. Cell-free protein synthesis: applications come of age. *Biotechnol Adv* 30, 1185-1194 (2012).
65. Kwon, Y. C. & Jewett, M. C. High-throughput preparation methods of crude extract for robust cell-free protein synthesis. *Sci Rep* 5, 8663 (2015).21
66. Jaroentomeechai, T. et al. Single-pot glycoprotein biosynthesis using a cell-free transcription-translation system enriched with glycosylation machinery. *Nat Commun* 9 (2018).
67. Kightlinger, W. et al. Design of glycosylation sites by rapid synthesis and analysis of glycosyltransferases. *Nat Chem Biol* 14, 627-635 (2018).
68. Shimizu, Y. et al. Cell-free translation reconstituted with purified components. *Nat Biotechnol* 19, 751-755 (2001).
69. Iwane, Y., Katoh, T., Goto, Y. & Suga, H. Artificial division of codon boxes for expansion of the amino acid repertoire of ribosomal polypeptide synthesis. *Methods Mol Biol* 1728, 17-47 (2018).
70. Udagawa, T., Shimizu, Y. & Ueda, T. Evidence for the translation initiation of leaderless mRNAs by the intact 70 S ribosome without its dissociation into subunits in eubacteria. *J Biol Chem* 279, 8539-8546 (2004).
71. Oza, J. P. et al. Robust production of recombinant phosphoproteins using cell-free protein synthesis. *Nat Commun* 6 (2015).
72. Liu, Y., Kim, D. S. & Jewett, M. C. Repurposing ribosomes for synthetic biology. *Curr Opin Chem Biol* 40, 87-94 (2017).
73. d'Aquino, A. E., Kim, D. S. & Jewett, M. C. Engineered ribosomes for basic science and synthetic biology. *Annu Rev Chem Biomol Eng* 9, 311-340 (2018).

Materials and Methods

All reagents and solvents were commercial grade and purified prior to use when necessary. Dichloromethane was dried by passage through a column of activated alumina as described by Grubbs.[1] Phenylalanine cyanomethyl ester (A) was prepared as recently described.[2] Tert-butyl (2-(4-(mercaptomethyl)benzamido)ethyl) carbamate (ABT) was prepared according to the standard procedure.[3] All organic solutions were dried over $MgSO_4$. Thin layer chromatography (TLC) was performed using glass-backed silica gel (250 m) plates. Flash chromatography was performed on a Biotage Isolera One automated purification system. UV light, and/or the use of KMnO4 were used to visualize products. Nuclear magnetic resonance spectra (NMR) were acquired on a Bruker Advance III-500 (500 MHz) or Varian Unity 500 (500 MHz) instrument. Chemical shifts are measured relative to residual solvent peaks as an internal standard set to δ 7.26 and δ 77.0 (CDCl3), and δ 2.50 and δ 39.5 (DMSO-$d_6$). Mass spectra were recorded on a Bruker AmaZon SL or Waters Q-TOF Ultima (ESI) and Impact-II or Waters 70-VSE (EI), spectrometers by use of the ionization method noted.

General Procedure for Formation of Cyanomethyl Ester

To a glass vial with a stir bar was added carboxylic acid (1 equiv.), CH2Cl2 (1.0 M), trimethylamine (1.5 equiv.), and chloroacetonitrile (1.2 equiv.). After stirring for 16 h at 25° C. the reaction mixture was diluted with EtOAc and washed with water or brine. The organic phase was dried and concentrated to provide the crude product. The product was purified by flash column chromatography if necessary.

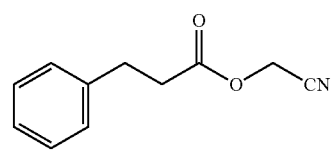 [SMILES: N#CCOC(=O)CCc1ccccc1]

Cyanomethyl 3-phenylpropanoate (B)

Prepared according to the general procedure using 3-phenylpropanoic acid (100 mg, 0.66 mmol), trimethylamine (140 μL, 0.99 mmol), chloroacetonitrile (53 μL, 0.79 mmol) and dichloromethane (0.7 mL). The product was obtained as a clear oil (95 mg, 77%). $^1$H NMR (500 MHz, CDCl3) δ 7.33 (t, J=7.6 Hz, 2H), 7.28-7.21 (m, 3H), 4.72 (s, 2H), 3.01 (t, J=7.8 Hz, 2H), 2.76 (t, J=7.8 Hz, 2H); 13C NMR (125 MHz, CDCl3) ppm 171.2, 139.5, 128.6, 128.2, 126.6, 114.3, 48.2, 35.1, 30.5; HRMS (EI): Exact mass calcd for C11H11NO2 [M]+ 189.07898, found 189.07881.

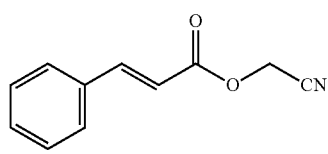 [SMILES: N#CCOC(=O)/C=C/c1ccccc1]

Cyanomethyl Trans-Cinnamate (C)

Prepared according to the general procedure using trans-cinnamic acid (98 mg, 0.66 mmol), triethylamine (140 μL, 0.99 mmol), chloroacetonitrile (53 μL, 0.79 mmol) and dichloromethane (0.7 mL). The product was obtained as a white solid (78 mg, 63%). 1H NMR (500 MHz, CDCl3) δ 7.80 (d, J=16.0 Hz, 1H), 7.57-7.53 (m, 2H), 7.44-7.40 (m, 3H), 6.46 (d, J=16.1 Hz, 1H), 4.86 (s, 2H); 13C NMR (125 MHz, CDCl3) ppm 165.1, 147.7, 133.6, 131.1, 129.0, 128.4, 115.2, 114.5, 48.4; HRMS (EI): Exact mass calcd for C11H9NO2 [M]+ 187.0633, found 187.0633.

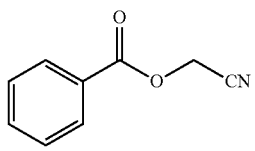 [SMILES: N#CCOC(=O)c1ccccc1]

Cyanomethyl Benzoate (D)

Prepared according to the general procedure using benzoic acid (81 mg, 0.66 mmol), triethylamine (140 μL, 0.99 mmol), chloroacetonitrile (53 μL, 0.79 mmol) and dichloromethane (0.7 mL). The product was obtained as a clear oil (87 mg, 82%). 1H NMR (500 MHz, CDCl3) δ 8.06 (dd, J=8.3, 1.4 Hz, 2H), 7.67-7.59 (m, 1H), 7.49 (t, J=7.8 Hz, 2H), 4.97 (s, 2H); 13C NMR (125 MHz, CDCl3) ppm 164.9, 134.1, 130.0, 128.7, 127.8, 114.4, 48.8; HRMS (EI): Exact mass calcd for C9H7NO2 [M]+ 161.0477, found 161.0475.

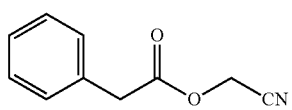 [SMILES: N#CCOC(=O)Cc1ccccc1]

Cyanomethyl 2-phenylacetate (E)

Prepared according to the general procedure using phenylacetic acid (90 mg, 0.66 mmol), triethylamine (140 μL, 0.99 mmol), chloroacetonitrile (53 μL, 0.79 mmol) and dichloromethane (0.7 mL). The product was obtained as a white solid (79 mg, 68%). 1H NMR (500 MHz, CDCl3) δ 7.35-7.23 (m, 5H), 4.70 (s, 2H), 3.70 (s, 2H); 13C NMR (125 MHz, CDCl3) ppm 169.9, 132.2, 129.2, 128.8, 127.6, 114.2, 48.6, 40.4; HRMS (EI): Exact mass calcd for C10H9NO2 [M]+ 175.0633, found 175.0634.

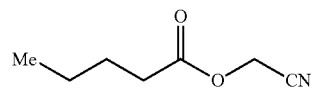

Cyanomethyl Pentanoate (F)

Prepared according to the general procedure using valeric acid (72 μL, 0.66 mmol), triethylamine (140 μL, 0.99 mmol), chloroacetonitrile (53 μL, 0.79 mmol) and dichloromethane (0.7 mL). The product was obtained as a clear oil (65 mg, 70%). 1H NMR (500 MHz, CDCl3) δ 4.71 (s, 2H), 2.41 (t, J=7.5 Hz, 2H), 1.67-1.60 (m, 2H), 1.41-1.30 (m, 2H), 0.92 (t, J=7.4 Hz, 3H); 13C NMR (125 MHz, CDCl3) ppm 172.1, 114.5, 48.1, 33.1, 26.6, 22.1, 13.6; HRMS (CI): Exact mass calcd for C7H12NO2 [M+H]+ 142.0868, found 142.0867.

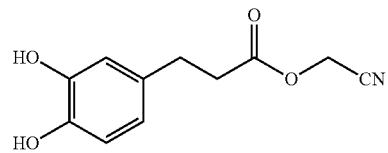 [SMILES: N#CCOC(=O)CCc1ccc(O)c(O)c1]

Cyanomethyl 3-(3,4-dihydroxyphenyl)propanoate (1)

Prepared according to the general procedure using 3-(3,4-dihydroxyphenyl)propanoic acid (60 mg, 0.33 mmol), triethylamine (70 μL, 0.5 mmol), chloroacetonitrile (26.5 μL, 0.4 mmol) and dichloromethane (0.2 mL). The product was obtained as a brown solid (40 mg, 55%). 1H-NMR (500 MHz, DMSO-d6) δ 8.73 (s, 1H), 8.67 (s, 1H), 6.61 (d, J=8.1 Hz, 1H), 6.58 (d, J=1.9 Hz, 1H), 6.46-6.44 (m, 1H), 4.94 (s, 2H), 2.69-2.68 (m, 2H), 2.66-2.64 (m, 2H); 13C NMR (125 MHz, DMSO-d6) ppm 171.9, 145.5, 144.0, 131.3, 119.2, 116.4, 116.1, 115.9, 49.3, 35.2, 29.8; HRMS (EI): Exact mass calcd for C11H11NO4: [M]+ 221.0688, found 221.0690.

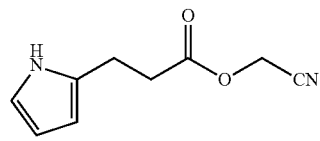 [SMILES: N#CCOC(=O)CCc1ccc[nH]1]

Cyanomethyl 3-(1H-pyrrol-2-yl)propanoate (2)

Prepared according to the general procedure using 3-(1H-pyrrol-2-yl)propanoic acid (46 mg, 0.33 mmol), triethylamine (70 μL, 0.5 mmol), chloroacetonitrile (26.5 μL, 0.4 mmol) and dichloromethane (0.2 mL). The product was obtained as a brown solid (45 mg, 77%). 1H-NMR (500 MHz, DMSO-d6) δ 10.54 (s, 1H), 6.58 (d, J=2.0 Hz, 1H), 5.88 (q, J=2.7, 3.0, 2.6 Hz, 1H), 5.74 (m, 1H), 4.96 (s, 2H), 2.81 (t, J=8 Hz, 2H), 2.70 (t, J=7 Hz, 2H); 13C NMR (125 MHz, DMSO-d6) ppm 171.9, 130.0, 116.8, 116.5, 107.6, 105.0, 49.4, 33.6, 22.8; HRMS (EI): Exact mass calcd for C9H10N2O2: [M]+ 178.0742, found 178.0743.

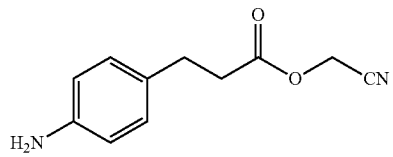 [SMILES: N#CCOC(=O)CCc1ccc(N)cc1]

Cyanomethyl 3-(4-aminophenyl)propanoate (3)

Prepared according to the general procedure using 3-(4-aminophenyl)propanoic acid (109 mg, 0.66 mmol), triethylamine (140 μL, 0.99 mmol), chloroacetonitrile (53 μL, 0.79 mmol) and dichloromethane (0.7 mL). The product was obtained as a white solid (123 mg, 55%). 1H NMR (500 MHz, CDCl3) δ 6.98 (d, J=8.2 Hz, 2H), 6.63 (d, J=8.2 Hz, 2H), 4.68 (s, 2H), 3.48 (br s, 2H), 2.87 (t, J=7.7 Hz, 2H), 2.67 (t, J=7.7 Hz, 2H); 13C NMR (125 MHz, CDCl3) ppm 171.4, 144.8, 129.5, 129.0, 115.3, 114.4, 48.1, 35.5, 29.8; HRMS (EI): Exact mass calcd for C11H12N2O2 [M]+ 204.0899, found 204.0897.

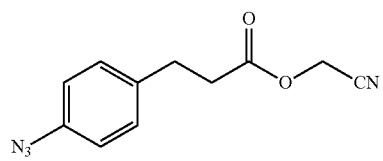 [SMILES: N#CCOC(=O)CCc1ccc(N=[N+]=[N-])cc1]

Cyanomethyl 3-(4-azidophenyl)propanoate (4)

Prepared according to the general procedure using 3-(4-azidophenyl)propanoic acid (126 mg, 0.66 mmol), triethylamine (140 μL, 0.99 mmol), chloroacetonitrile (53 μL, 0.79 mmol) and dichloromethane (0.7 mL). The product was obtained as a red oil (123 mg, 81%). 1H NMR (500 MHz, CD3CN) δ 7.25 (d, J=8.5 Hz, 2H), 7.00 (d, J=8.4 Hz, 2H), 4.72 (s, 2H), 2.91 (t, J=7.6 Hz, 2H), 2.70 (t, J=7.6 Hz, 2H); 13C NMR (125 MHz, CD3CN) ppm 172.4, 139.0, 138.1, 130.8, 119.9, 116.2, 49.6, 35.4, 30.3; HRMS (EI): Exact mass calcd for C11H10N4O2 [M]+ 230.0804, found 230.0794.

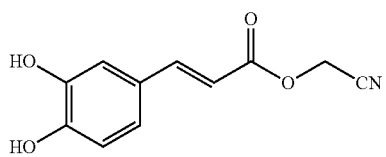 [SMILES: N#CCOC(=O)/C=C/c1ccc(O)c(O)c1]

Cyanomethyl (E)-3-(3,4-dihydroxyphenyl)acrylate (5)

Prepared according to the general procedure using (E)-3-(3,4-dihydroxyphenyl)acrylic acid (59 mg, 0.33 mmol), triethylamine (70 μL, 0.5 mmol), chloroacetonitrile (26.5 μL, 0.4 mmol) and dichloromethane (0.2 mL). The product was obtained as a pink solid (41 mg, 57%). 1H-NMR (500 MHz, DMSO-d6) δ 9.71 (s, 1H), 9.20 (s, 1H), 7.61 (m, 1H), 7.10 (d, J=1.8 Hz, 1H), 7.07 (dd, J=8.3, 1.7 Hz, 1H), 6.78 (d, J=8.4 Hz, 1H), 6.35 (d, J=16.3 Hz, 1H), 5.06 (s, 2H); 13C NMR (125 MHz, DMSO-d6) ppm 165.9, 149.5, 147.9, 146.1, 125.6, 122.5, 116.7, 116.2, 115.6, 112.0, 49.3; HRMS (EI): Exact mass calcd for C11H9NO4: [M]+ 219.0532, found 219.0531.

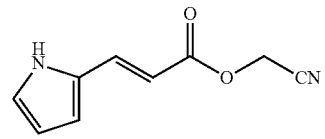 [SMILES: N#CCOC(=O)/C=C/c1ccc[nH]1]

Cyanomethyl (E)-3-(1H-pyrrol-2yl)acrylate (6)

Prepared according to the general procedure using (E)-3-(1H-pyrrol-2-yl)acrylic acid (45 mg, 0.33 mmol), triethylamine (70 μL, 0.5 mmol), chloroacetonitrile (26.5 μL, 0.4 mmol) and dichloromethane (0.2 mL). The product was obtained as a brown solid (24 mg, 43%). 1H-NMR (500 MHz, DMSO-d6) δ 11.65 (s, 1H), 7.56 (d, J=15.6 Hz, 1H), 7.11 (m, 1H), 6.67 (m, 1H), 6.24 (d, J=15.8 Hz, 1H), 6.22-6.20 (m, 1H), 5.02 (s, 2H); 13C NMR (125 MHz, DMSO-d6) ppm 166.2, 137.3, 128.4, 125.0, 116.8, 116.7, 110.9, 107.8, 49.2; HRMS (EI): Exact mass calcd for C9H8N2O2: [M]+ 176.0586, found 176.0586.

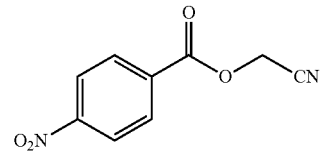 [SMILES: N#CCOC(=O)c1ccc([N+](=O)[O-])cc1]

Cyanomethyl 4-nitrobenzoate (7)

Prepared according to the general procedure using 4-nitrobenzoic acid (110 mg, 0.66 mmol), triethylamine (140 μL, 0.99 mmol), chloroacetonitrile (53 μL, 0.79 mmol) and dichloromethane (0.7 mL). The product was obtained as a beige solid (69 mg, 51%). 1H NMR (500 MHz, CDCl3) δ 8.34 (d, J=8.9 Hz, 2H), 8.26 (d, J=9.0 Hz, 2H), 5.03 (s, 2H); 13C NMR (125 MHz, CDCl3) ppm 163.2, 151.2, 133.1, 131.2, 123.9, 113.8, 49.5; HRMS (EI): Exact mass calcd for C9H6N2O4 [M]+ 206.03276, found 206.03188.

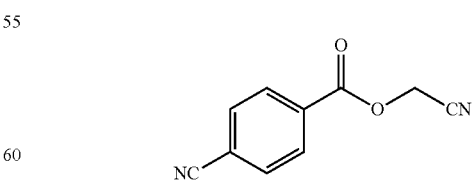

Cyanomethyl 4-cyanobenzoate (8)

Prepared according to the general procedure using 4-cyanobenzoic acid (97 mg, 0.66 mmol), triethylamine (140 μL, 0.99 mmol), chloroacetonitrile (53 μL, 0.79 mmol) and dichloromethane (0.7 mL). The product was obtained as a white solid (101 mg, 82%). 1H NMR (500 MHz, CDCl3) δ 8.18 (d, J=8.5 Hz, 2H), 7.80 (d, J=8.5 Hz, 2H), 5.01 (s, 2H); 13C NMR (125 MHz, CDCl3) ppm 163.4, 132.5, 131.6, 130.5, 124.8, 117.6, 113.9, 49.4; HRMS (EI): Exact mass calcd for C10H6N2O2 [M]+ 186.0429, found 186.0426.

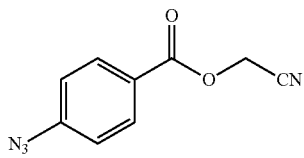 [SMILES: N#CCOC(=O)c1ccc(N=[N+]=[N-])cc1]

Cyanomethyl 4-azidobenzoate (9)

Prepared according to the general procedure using 4-azidobenzoic acid (108 mg, 0.66 mmol), triethylamine (140 μL, 0.99 mmol), chloroacetonitrile (53 μL, 0.79 mmol) and dichloromethane (0.7 mL). The product was obtained as a red oil (89 mg, 67%). 1H NMR (500 MHz, CD3CN) δ 8.02 (d, J=8.7 Hz, 2H), 7.17 (d, J=8.7 Hz, 2H), 4.97 (s, 2H); 13C NMR (125 MHz, CD3CN) ppm 165.2, 146.8, 132.4, 125.6, 120.2, 116.2, 50.3; HRMS (EI): Exact mass calcd for C9H6N4O2 [M]+ 202.0491, found 202.0487.

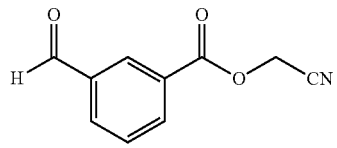 [SMILES: N#CCOC(=O)c1cccc(C=O)c1]

Cyanomethyl 3-formylbenzoate (10)

Prepared according to the general procedure using 3-formylbenzoic acid (99 mg, 0.66 mmol), triethylamine (140 μL, 0.99 mmol), chloroacetonitrile (53 μL, 0.79 mmol) and dichloromethane (0.7 mL). The product was obtained as a clear oil (95 mg, 69%). 1H NMR (500 MHz, CDCl3) δ 10.09 (s, 1H), 8.55 (t, J=1.7 Hz, 1H), 8.32 (d, J=7.8 Hz, 1H), 8.16 (d, J=7.7 Hz, 1H), 7.69 (t, J=7.7 Hz, 1H), 5.02 (s, 2H); 13C NMR (125 MHz, CDCl3) ppm 190.9, 163.9, 136.7, 135.4, 134.3, 131.4, 129.7, 129.0, 114.1, 49.2; HRMS (EI): Exact mass calcd for C10H6NO3 [M]+ 189.0347, found 189.0344.

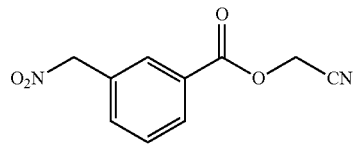 [SMILES: N#CCOC(=O)c1cccc(C[N+](=O)[O-])c1]

Cyanomethyl 3-(nitromethyl)benzoate (11)

Prepared according to the general procedure using 3-bromobenzoic acid (500 mg, 2.49 mmol), triethylamine (520 μL, 3.74 mmol), chloroacetonitrile (188 μL, 2.99 mmol) and dichloromethane (2.5 mL). The product was obtained as a white oily solid (579 mg, 97%). 1H NMR (500 MHz, CDCl3) δ 8.20 (dd, J=1.8, 1.8 Hz, 1H), 8.00 (ddd, J=7.8, 1.7, 1.1 Hz, 1H), 7.76 (ddd, J=8.0, 2.0, 1.1 Hz, 1H), 7.38 (dd, J=7.9, 7.9 Hz, 1H), 4.97 (s, 2H); 13C NMR (125 MHz, CDCl3) ppm 163.5, 136.9, 132.7, 130.2, 129.6, 128.4, 122.6, 114.2, 49.0; HRMS (EI): Exact mass calcd for C9H6NO2Br [M]+ 238.95818, found 238.95761. According to literature procedure, to a flame-dried glass vial under an argon atmosphere was added cyanomethyl 3-bromobenzoate (192 mg, 0.80 mmol), K3PO4 (204 mg, 0.96 mmol), XPhos (23.9 mg, 0.05 mmol), Pd2dba3 (18.3 mg, 0.02 mmol), nitromethane (430 μL, 8.0 mmol) and dioxane (3.6 mL). The reaction mixture was stirred at 70° C. for 24 h. After cooling to room temperature, the mixture was diluted with CH2Cl2 and washed with 1 M HCl. The organic phase was dried (MgSO4) and concentrated. Flash column chromatography (SiO2, 10-35% ethyl acetate in hexanes) yielded the product as a yellow oil (120 mg, 68%). 1H NMR (500 MHz, CDCl3) δ 8.16 (s, 1H), 8.15 (d, J=8.7 Hz, 1H), 7.74 (d, J=7.8 Hz, 1H), 7.59 (dd, J=7.7, 7.7 Hz, 1H), 5.51 (s, 2H), 4.99 (s, 2H); 13C NMR (125 MHz, CDCl3) ppm 164.0, 135.5, 131.6, 131.5, 130.3, 129.7, 128.9, 114.2, 79.1, 49.1; HRMS (CI): Exact mass calcd for C10H9N2O4 [M+H]+ 221.0562, found 221.0558.

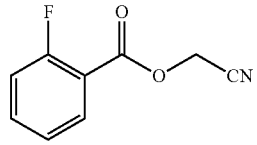

Cyanomethyl 2-fluorobenzoate (12)

Prepared according to the general procedure using 2-fluorobenzoic acid (92 mg, 0.66 mmol), triethylamine (140 μL, 0.99 mmol), chloroacetonitrile (53 μL, 0.79 mmol) and dichloromethane (0.7 mL). The product was obtained as a red oil (66 mg, 56%). 1H NMR (500 MHz, CDCl3) δ 7.98 (td, J=7.5, 1.8 Hz, 1H), 7.61 (tdd, J=7.0, 5.9, 3.3 Hz, 1H), 7.26 (td, J=7.7, 1.1 Hz, 1H), 7.19 (ddd, J=10.7, 8.4, 1.1 Hz, 1H), 4.98 (s, 2H); 13C NMR (125 MHz, CDCl3) ppm 162.6 (d, 3JCF=3.6 Hz), 162.2 (d, 1JCF=262.4 Hz), 135.9 (d, 3JCF=9.1 Hz), 132.3, 124.2 (d, 3JCF=4.0 Hz), 117.2 (d, 2JCF=21.9 Hz), 116.3 (d, 2JCF=9.3 Hz), 114.2, 48.8; HRMS (EI): Exact mass calcd for C9H6FNO2 [M]+ 179.0383, found 179.0383.

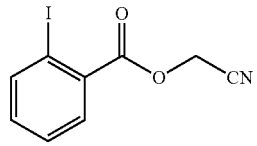 [SMILES: N#CCOC(=O)c1ccccc1I]

Cyanomethyl 2-iodobenzoate (13)

Prepared according to the general procedure using 2-iodobenzoic acid (164 mg, 0.66 mmol), triethylamine (140 μL, 0.99 mmol), chloroacetonitrile (53 μL, 0.79 mmol) and dichloromethane (0.7 mL). The product was obtained as a red oil (129 mg, 68%). 1H NMR (500 MHz, CDCl3) δ 8.05 (dd, J=8.0, 1.2 Hz, 1H), 7.88 (dd, J=7.8, 1.7 Hz, 1H), 7.45

(td, J=7.6, 1.2 Hz, 1H), 7.23 (td, J=7.7, 1.7 Hz, 1H), 4.97 (s, 2H); 13C NMR (125 MHz, CDCl3) ppm 164.4, 141.9, 133.8, 132.2, 131.6, 128.1, 114.1, 94.7, 49.1; HRMS (EI): Exact mass calcd for C9H6INO2 [M]+286.9443, found 286.9448.

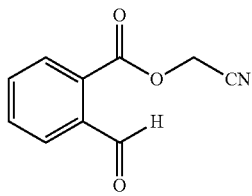 [SMILES: N#CCOC(=O)c1ccccc1C=O]

Cyanomethyl 2-formylbenzoate (14)

Prepared according to the general procedure using 2-formylbenzoic acid (150 mg, 1.00 mmol), trimethylamine (153 μL, 1.10 mmol), chloroacetonitrile (191 μL, 3.00 mmol) and dichloromethane (2.0 mL). The product was obtained as a clear oil (146 mg, 77%). 1H NMR (500 MHz, CDCl3) δ 10.58 (s, 1H), 7.99 (d, J=7.5 Hz, 2H), 7.73 (m, 2H), 5.01 (s, 2H); 13C NMR (125 MHz, CDCl3) ppm 191.2, 164.7, 137.2, 133.5, 133.2, 130.5, 129.4, 124.7, 114.0, 49.3; HRMS (EI): Exact mass calcd for C10H6NO3 [M]+ 189.0348, found 189.0363.

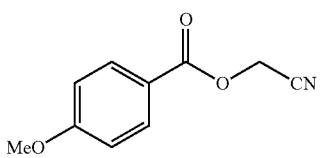 [SMILES: COc1ccc(C(=O)OCC#N)cc1]

Cyanomethyl 4-methoxybenzoate (15)

Prepared according to the general procedure using 4-methoxybenzoic acid (100 mg, 0.66 mmol), trimethylamine (140 μL, 0.99 mmol), chloroacetonitrile (53 μL, 0.79 mmol) and dichloromethane (0.7 mL). The product was obtained as a white solid (102 mg, 81%). 1H NMR (500 MHz, CDCl3) δ 8.01 (d, J=9.0 Hz, 2H), 6.95 (d, J=8.9 Hz, 2H), 4.93 (s, 2H), 3.88 (s, 3H); 13C NMR (125 MHz, CDCl3) ppm 164.6, 164.3, 132.2, 120.1, 114.7, 114.0, 55.5, 48.6; HRMS (EI): Exact mass calcd for C10H9NO3 [M]+ 191.0582, found 191.0581.

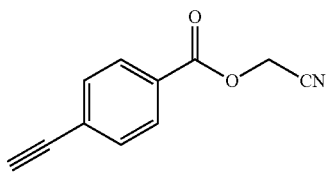

Cyanomethyl 4-ethynylbenzoate (16)

Prepared according to the general procedure using 4-ethynylbenzoic acid (96 mg, 0.66 mmol), trimethylamine (140 μL, 0.99 mmol), chloroacetonitrile (53 μL, 0.79 mmol) and dichloromethane (0.7 mL). The product was obtained as a white solid (87 mg, 76%). 1H NMR (500 MHz, CDCl3) δ 8.02 (d, J=8.5 Hz, 2H), 7.59 (d, J=8.4 Hz, 2H), 4.97 (s, 2H), 3.29 (s, 1H); 13C NMR (125 MHz, CDCl3) ppm 164.3, 132.4, 129.9, 128.1, 127.7, 114.3, 82.4, 81.0, 49.0; HRMS (EI): Exact mass calcd for C11H7NO2 [M]+ 185.0477, found 185.0476.

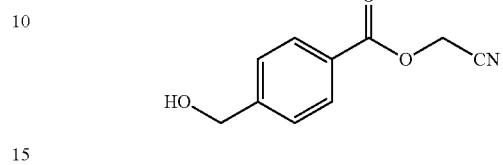

Cyanomethyl 4-(hydroxymethyl)benzoate (17)

Prepared according to the general procedure using 4-(hydroxymethyl)benzoic acid (500 mg, 3.29 mmol), triethylamine (700 μL, 4.94 mmol), chloroacetonitrile (266 μL, 3.95 mmol) and dichloromethane (1.2 mL). The product was obtained as a white solid (470 mg, 75%). 1H NMR (500 MHz, CDCl3) δ 8.03 (d, J=8.0 Hz, 1H), 7.47 (d, J=7.9 Hz, 1H), 4.96 (s, 2H), 4.79 (s, 2H), 2.10 (br s, 1H); 13C NMR (125 MHz, CDCl3) ppm 164.8, 147.4, 130.3, 126.9, 126.6, 114.5, 64.4, 48.8; HRMS (ESI): Exact mass calcd for C10H9NNaO3 [M+Na]+214.0480, found 214.0486.

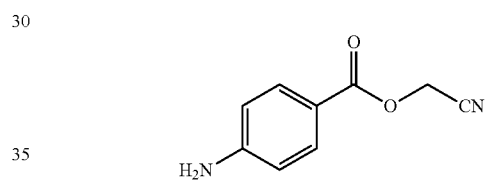

Cyanomethyl 4-aminobenzoate (18)

Prepared according to the general procedure using 4-(Boc-amino)benzoic acid (78 mg, 0.33 mmol), triethylamine (70 μL, 0.5 mmol), chloroacetonitrile (26.5 μL, 0.4 mmol) in DMF (0.4 mL). The product was obtained as a white solid (39 mg, 68%) 1H-NMR (500 MHz, DMSO-d6) δ 7.66 (td, J=8.7 Hz, 2H), 6.59 (td, J=8.6 Hz, 2H), 6.18 (s, 2H), 5.08 (s, 2H); 13C NMR (125 MHz, DMSO-d6) ppm 165.1, 154.9, 132.2, 117.0, 113.9, 113.3, 49.3; Exact mass calcd for C9H8N2O2 [M]+176.0586, found 176.0585.

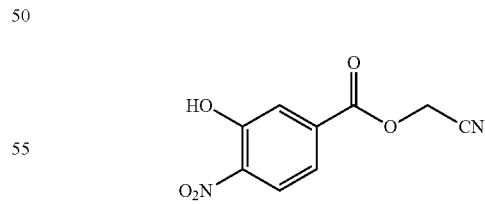

Cyanomethyl 3-hydroxy-4-nitrobenzoate (19)

Prepared according to the general procedure using 3-hydroxy-4-nitrobenzoic acid (200 mg, 1.09 mmol), triethylamine (232 μL, 1.64 mmol), chloroacetonitrile (88 μL, 1.31 mmol) and dichloromethane (1.2 mL). The product was obtained as a yellow solid (92 mg, 38%). 1H NMR (500 MHz, CDCl3) δ 10.51 (s, 1H), 8.23 (d, J=8.8 Hz, 1H), 7.87

(d, J=1.9 Hz, 1H), 7.65 (dd, J=8.8, 1.8 Hz, 1H), 5.00 (s, 2H); 13C NMR (125 MHz, CDCl3) ppm 162.9, 154.7, 136.4, 135.4, 125.7, 122.3, 120.8, 113.7, 49.5; HRMS (EI): Exact mass calcd for C9H6N2O5 [M]+ 222.0276, found 222.0272.

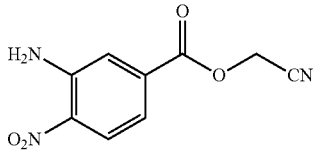

Cyanomethyl 3-amino-4-nitrobenzoate (20)

Prepared according to the general procedure using 3-amino-4-nitrobenzoic acid (198 mg, 1.09 mmol), triethylamine (232 µL, 1.64 mmol), chloroacetonitrile (88 µL, 1.31 mmol) and dichloromethane (1.2 mL). The product was obtained as a yellow solid (210 mg, 87%). 1H NMR (500 MHz, d6-DMSO) δ 8.10 (dd, J=9.0, 1.0 Hz, 1H), 7.74 (d, J=1.9 Hz, 1H), 7.65 (s, 2H), 7.09 (dd, J=8.9, 1.9 Hz, 1H), 5.24 (s, 2H); 13C NMR (125 MHz, d6-DMSO) ppm 163.7, 145.7, 133.6, 132.5, 126.5, 121.5, 115.9, 114.5, 50.4; HRMS (ESI): Exact mass calcd for C9H7N3NaO4 [M+Na]+ 244.0334, found 244.0335.

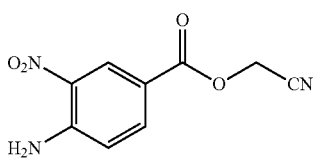 [SMILES: N#CCOC(=O)c1ccc(N)c([N+](=O)[O-])c1]

Cyanomethyl 4-amino-3-nitrobenzoate (21)

Prepared according to the general procedure using 4-amino-3-nitrobenzoic acid (198 mg, 1.09 mmol), triethylamine (232 µL, 1.64 mmol), chloroacetonitrile (88 µL, 1.31 mmol) and dichloromethane (1.2 mL). The product was obtained as a yellow solid (120 mg, 49%). 1H NMR (500 MHz, d6-acetone) δ 8.74 (d, J=1.9 Hz, 1H), 7.96 (dd, J=8.9, 2.0 Hz, 1H), 7.68 (s, 2H), 7.19 (d, J=9.0 Hz, 1H), 5.17 (s, 2H); 13C NMR (125 MHz, d6-acetone) ppm 164.3, 150.2, 136.0, 129.9, 120.3, 120.2, 116.3, 116.2, 49.9; HRMS (ESI): Exact mass calcd for C9H7N3NaO4 [M+Na]+244.0334, found 244.0329.

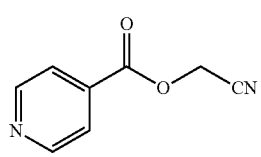 [SMILES: N#CCOC(=O)c1ccncc1]

Cyanomethyl Isonicotinate (22)

Prepared according to the general procedure using isonicotinic acid (81 mg, 0.66 mmol), triethylamine (140 µL, 0.99 mmol), chloroacetonitrile (53 µL, 0.79 mmol) and dichloromethane (0.7 mL). The product was obtained as a red oil (50 mg, 47%). 1H NMR (500 MHz, CDCl3) δ 8.85 (d, J=3.9 Hz, 2H), 7.87 (d, J=6.1 Hz, 2H), 5.01 (s, 2H); 13C NMR (125 MHz, CDCl3) ppm 163.7, 150.9, 135.0, 122.9, 113.8, 49.4; HRMS (EI): Exact mass calcd for C8H6N2O4 [M]+ 162.0429, found 162.0430.

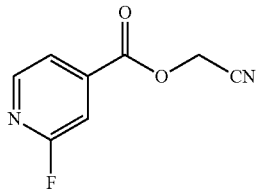 [SMILES: N#CCOC(=O)c1ccnc(F)c1]

Cyanomethyl 2-fluoroisonicotinate (23)

Prepared according to the general procedure using 2-fluoroisonicotinic acid (93 mg, 0.66 mmol), trimethylamine (140 µL, 0.99 mmol), chloroacetonitrile (53 µL, 0.79 mmol) and dichloromethane (0.7 mL). The product was obtained as a white solid (102 mg, 86%). 1H NMR (500 MHz, CDCl3) δ 8.43 (d, J=5.1 Hz, 1H), 7.77 (m, 1H), 7.52 (dd, J=2.6, 1.2 Hz, 1H), 5.02 (s, 2H); 13C NMR (125 MHz, CDCl3) ppm 164.4 (d, 1JCF=241.1 Hz), 162.7 (d, 4JCF=4.5 Hz), 149.4 (d, 3JCF=14.6 Hz), 140.6 (d, 3JCF=7.8 Hz), 121.1 (d, 4JCF=4.9 Hz), 113.8, 110.4 (d, 2JCF=39.7 Hz), 49.9; HRMS (EI): Exact mass calcd for C8H5FN2O2 [M]+ 180.0335, found 180.0332.

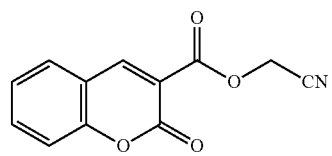 [SMILES: N#CCOC(=O)c1cc2ccccc2oc1=O]

Cyanomethyl 2-oxo-2H-chromene-3-carboxylate (24)

Prepared according to the general procedure using 2-oxo-2H-chromene-3-carboxylic acid (125 mg, 0.66 mmol), triethylamine (140 µL, 0.99 mmol), chloroacetonitrile (53 µL, 0.79 mmol) and dichloromethane (0.7 mL). The product was obtained as a white solid (118 mg, 78%). 1H NMR (500 MHz, CDCl3) δ 8.67 (s, 1H), 7.72 (dd, J=8.0, 7.5 Hz, 1H), 7.67 (d, J=7.2 Hz, 1H), 7.40 (d, J=8.0 Hz, 1H), 7.39 (dd, J=8.0, 7.5 Hz, 1H), 4.99 (s, 2H); 13C NMR (125 MHz, CDCl3) ppm 161.5, 156.0, 155.5, 150.9, 135.5, 130.0, 125.2, 117.5, 117.0, 115.7, 113.9, 49.3; HRMS (EI): Exact mass calcd for C12H7NNO4 [M]+ 229.0375, found 229.0382.

Cyanomethyl 1H-pyrrole-2-carboxylate (25)

Prepared according to the general procedure using 1H-pyrrole-2-carboxylic acid (37 mg, 0.33 mmol), triethylamine (70 L, 0.5 mmol), chloroacetonitrile (26.5 μL, 0.4 mmol) and dichloromethane (0.2 mL). The product was obtained as a white solid (24 mg, 49%). 1H-NMR (500 MHz, DMSO-d6) δ 12.15 (s, 1H), 7.13 (m, 1H), 6.91 (m, 1H), 6.23 (m, 1H), 5.12 (s, 2H); 13C NMR (125 MHz, DMSO-d6) ppm 159.4, 126.2, 120.3, 117.2, 116.7, 110.6, 49.2; ESI-MS; calculated mass for C7H6N2O2: [M]+ 150.0429, found 150.0432.

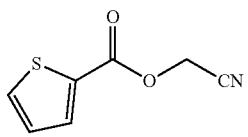 [SMILES: N#CCOC(=O)c1cccs1]

Cyanomethyl thiophene-2-carboxylate (26)

Prepared according to the general procedure using thiophene-2-carboxylic acid (84 mg, 0.66 mmol), triethylamine (140 L, 0.99 mmol), chloroacetonitrile (53 μL, 0.79 mmol) and dichloromethane (0.7 mL). The product was obtained as a brown oil (72 mg, 79%). 1H NMR (500 MHz, CDCl3) δ 7.89 (dd, J=3.8, 1.3 Hz, 1H), 7.67 (dd, J=5.0, 1.3 Hz, 1H), 7.15 (dd, J=4.9, 3.8 Hz, 1H), 4.94 (s, 2H); 13C NMR (125 MHz, CDCl3) ppm 160.4, 135.2, 134.3, 130.7, 128.2, 114.2, 48.7; HRMS (EI): Exact mass calcd for C7H5NO2S [M]+ 167.0041, found 167.0038.

General Procedure for Formation of ABT Ester

According to standard procedure[3], to a glass vial equipped with a stir bar was added tert-butyl (2-(4-(mercaptomethyl)benzamido)ethyl) carbamate (ABT) (1 equiv.), carboxylic acid (1.4 equiv.), CH2Cl2 (0.3 M), DMAP (2.8 equiv.), and EDC·HCl (2.8 equiv.). After stirring for 3 h at 25° C., the reaction was evaporated under reduced pressure, diluted with EtOAc, and washed with 1M HCl and saturated NaHCO3. The organic phase was dried and concentrated to provide the crude Bocprotected product. The Boc-protected product was purified by flash column chromatography. The purified product was dissolved in 4M HCl·dioxane and stirred for 1 h. Concentration under reduced pressure provided the product in sufficient purity.

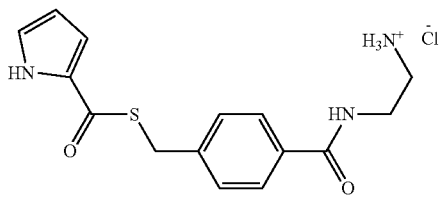 [SMILES: [NH3+]CCNC(=O)c1ccc(CSC(=O)c2ccc[nH]2)cc1 ; Cl]

2-(4-(((1H-pyrrole-2-carbonyl)thio)methyl)benzamido)ethan-1-aminium chloride (25a)

Prepared according to the general procedure using 1H-pyrrole-2-carboxylic acid (50 mg, 0.45 mmol), ABT (100 mg, 0.32 mmol), DMAP (109 mg, 0.9 mmol), EDC·HCl (171 mg, 0.9 mmol) and dichloromethane (2.0 mL). Flash column chromatography (SiO2 30%-50% ethyl acetate in hexanes) yielded the Boc-protected product as a white solid (60 mg, 15%). Bocdeprotection with 4M HCl·dioxane provided the product, which was used without further purification and characterization. Boc-25a: 1H NMR (500 MHz, CDCl3) δ 9.26 (s, 1H), 7.77 (d, J=7.9 Hz, 2H), 7.43 (d, J=8.1 Hz, 2H), 7.14 (s, 1H), 7.03 (d, J=11.4 Hz, 2H), 6.29 (d, J=3.0 Hz, 1H), 4.97 (s, 1H), 4.31 (s, 2H), 3.57 (q, J=5.1 Hz, 2H), 3.45-3.38 (m, 2H), 1.44 (s, 9H). 13C NMR (125 MHz, CDCl3) ppm 180.48, 167.37, 133.06, 129.71, 129.02, 127.32, 123.84, 115.37, 110.92, 42.09, 40.00, 31.91, 28.34. HRMS (ESI): Exact mass calcd for C20H26N3O4S [M+H]+ 404.1644, found 404.1632.

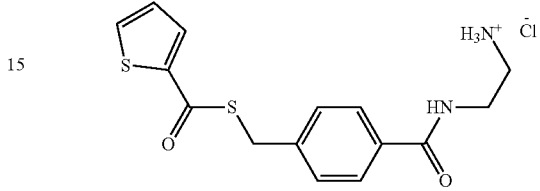

2-(4-(((thiophene-2-carbonyl)thio)methyl)benzamido)ethan-1-aminium chloride (26a)

Prepared according to the general procedure using thiophene-2-carboxylic acid (57 mg, 0.45 mmol), ABT (100 mg, 0.32 mmol), DMAP (109 mg, 0.9 mmol), EDC·HCl (171 mg, 0.9 mmol) and dichloromethane (2.0 mL). Flash column chromatography (SiO2 30%-50% ethyl acetate in hexanes) yielded the Boc-protected product as a white solid (150 mg, 76%). Boc-deprotection with 4M HCl·dioxane provided the product, which was used without further purification and characterization. Boc-26a: 1H NMR (500 MHz, CDCl3) δ 7.84-7.75 (m, 3H), 7.65 (dd, J=4.9, 1.1 Hz, 1H), 7.44 (d, J=8.1 Hz, 2H), 7.22 (br, 1H), 7.13 (dd, J=4.9, 3.9 Hz, 1H), 5.00 (s, 1H), 4.35 (s, 2H), 3.56 (q, J=5.1 Hz, 2H), 3.45-3.37 (m, 2H), 1.44 (s, 9H). 13C NMR (125 MHz, CDCl3) ppm 182.92, 167.32, 157.50, 141.52, 141.06, 133.22, 132.98, 131.34, 129.11, 128.38, 128.32, 127.96, 127.39, 126.09, 42.12, 39.99, 32.99, 28.34. HRMS (ESI): Exact mass calcd for C20H25N2O4S2 [M+H]+ 421.1256, found 421.1249.

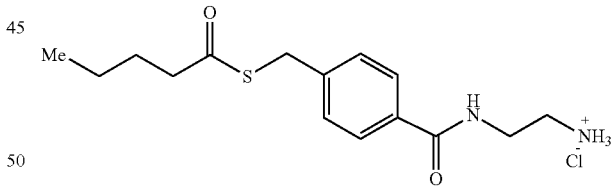

2-(4-((Pentanoylthio)methyl)benzamido)ethan-1-aminium chloride (G)

Prepared according to the general procedure using valeric acid (47 μL, 0.43 mmol), ABT (93 mg, 0.30 mmol), DMAP (105 mg, 0.86 mmol), EDC·HCl (165 mg, 0.86 mmol) and dichloromethane (1.0 mL). Flash column chromatography (SiO2 30%-50% ethyl acetate in hexanes) yielded the Boc-protected product as a white solid (66 mg, 56%). Bodeprotection with 4M HCl·dioxane provided the product, which was used without further purification and characterization. Boc-G: 1H NMR (500 MHz, CDCl3) δ 7.73 (d, J=7.9 Hz, 2H), 7.30 (d, J=8.0 Hz, 2H), 7.28 (br s, 1H), 5.14 (br s, 1H), 4.11 (s, 2H), 3.52 (q, 5.3 Hz, 2H), 3.37 (m, 2H), 2.56 (t, J=7.5 Hz, 2H), 1.63 (p, J=7.5 Hz, 2H), 1.40 (s, 9H), 1.33 (p, J=7.5 Hz, 2H), 0.89 (t, J=7.4 Hz, 3H); 13C NMR (125 MHz, CDCl3) ppm 198.6, 167.4, 157.5 141.4, 133.0, 128.8, 127.3, 79.9, 43.5, 42.0, 39.9, 32.7, 28.3, 27.6, 22.0, 13.7; HRMS (ESI): Exact mass calcd for C20H31N2O4S [M+H]+ 395.2005, found 395.2009.

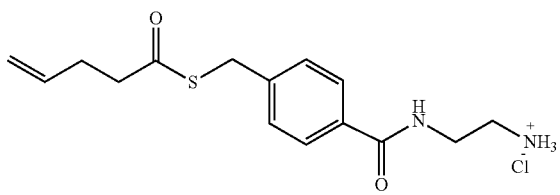 [SMILES: C=CCCC(=O)SCCc1ccc(C(=O)NCCN)cc1 ; Cl]

2-(4-((Pent-4-enoylthio)methyl)benzamido)ethan-1-aminium chloride (27)

Prepared according to the general procedure using 4-pentenoic acid (44 µL, 0.43 mmol), ABT (93 mg, 0.30 mmol), DMAP (105 mg, 0.86 mmol), EDC·HCl (165 mg, 0.86 mmol) and dichloromethane (1.0 mL). Flash column chromatography (SiO2 30%-50% ethyl acetate in hexanes) yielded the Boc-protected product as a white solid (61 mg, 52%). Boc-deprotection with 4M HCl·dioxane provided the product, which was used without further purification and characterization. Boc-15: 1H NMR (500 MHz, CDCl3) δ 7.73 (d, J=8.0 Hz, 2H), 7.30 (d, J=8.3 Hz, 2H), 7.29 (br s, 1H), 5.77 (ddt, J=16.8, 10.2, 6.5 Hz, 1H), 5.16 (br s, 1H), 5.04 (dd, J=17.1, 1.7 Hz, 1H), 4.99 (dd, J=10.2, 5.1 Hz, 1H), 4.12 (s, 2H), 3.52 (q, 5.2 Hz, 2H), 3.37 (m, 2H), 2.65 (dd, J=8.3, 6.7 Hz, 2H), 2.40 (tdd, J=8.5, 5.9, 3.5 Hz, 2H), 1.40 (s, 9H); 13C NMR (125 MHz, CDCl3) ppm 197.8, 167.4, 157.5, 141.3, 135.9, 133.0, 128.8, 127.3, 115.9, 79.9, 42.8, 42.0, 39.9, 32.7, 29.3, 28.3; HRMS (ESI): Exact mass calcd for C20H29N2O4S [M+H]+ 393.1848, found 393.1850.

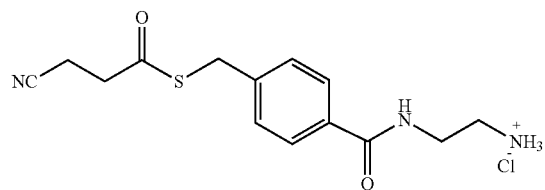 [SMILES: N#CCCC(=O)SCCc1ccc(C(=O)NCCN)cc1 ; Cl]

2-(4-(((3-Cyanopropanoyl)thio)methyl)benzamido)ethan-1-aminium chloride (28)

Prepared according to the general procedure using 3-cyanopropanoic acid (43 mg, 0.43 mmol), ABT (93 mg, 0.30 mmol), DMAP (105 mg, 0.86 mmol), EDC·HCl (165 mg, 0.86 mmol) and dichloromethane (1.0 mL). Flash column chromatography (SiO2 30%-50% ethyl acetate in hexanes) yielded the Boc-protected product as a white solid (42 mg, 36%). Bocdeprotection with 4M HCl·dioxane provided the product, which was used without further purification and characterization. Boc-16: 1H NMR (500 MHz, CDCl3) δ 7.75 (d, J=7.9 Hz, 2H), 7.32 (d, J=8.2 Hz, 2H), 7.27 (br s, 1H), 5.07 (br s, 1H), 4.18 (s, 2H), 3.53 (q, 5.1 Hz, 2H), 3.38 (q, J=5.8 Hz, 2H), 2.94 (dd, J=7.7, 6.7 Hz, 2H), 2.68 (dd, J=7.7, 6.7 Hz, 2H), 1.42 (s, 9H); 13C NMR (125 MHz, CDCl3) ppm 194.5, 167.2, 157.5, 140.3, 133.4, 128.9, 127.4, 118.0, 80.0, 42.1, 39.9, 38.3, 33.0, 28.3, 12.8; HRMS (ESI): Exact mass calcd for C19H26N3O4S [M+H]+ 392.1644, found 392.1658.

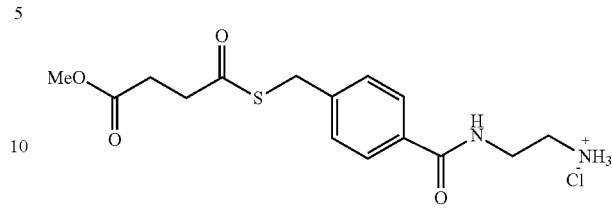

2-(4-(((4-Methoxy-4-oxobutanoyl)thio)methyl)benzamido)ethan-1-aminium chloride (29)

Prepared according to the general procedure using monomethyl succinic acid (57 mg, 0.43 mmol), ABT (93 mg, 0.30 mmol), DMAP (105 mg, 0.86 mmol), EDC·HCl (165 mg, 0.86 mmol) and dichloromethane (1.0 mL). Flash column chromatography (SiO2 30%-50% ethyl acetate in hexanes) yielded the Boc-protected product as a white solid (57 mg, 45%). Boc-deprotection with 4M HCl·dioxane provided the product, which was used without further purification and characterization. Boc-17: 1H NMR (500 MHz, CDCl3) δ 7.73 (d, J=7.9 Hz, 2H), 7.30 (d, J=8.0 Hz, 2H), 7.29 (br s, 1H), 5.14 (br s, 1H), 4.13 (s, 2H), 3.67 (s, 3H), 3.51 (q, 5.3 Hz, 2H), 3.37 (m, 2H), 2.89 (t, J=6.9 Hz, 2H), 2.66 (t, J=6.9 Hz, 2H), 1.41 (s, 9H); 13C NMR (125 MHz, CDCl3) ppm 196.8, 172.3, 167.3, 157.5, 141.0, 133.1, 128.9, 127.3, 79.9, 51.9, 42.0, 39.9, 38.1, 32.8, 28.9, 28.3; HRMS (ESI): Exact mass calcd for C20H29N2O6S [M+H]+ 425.1746, found 425.1759.

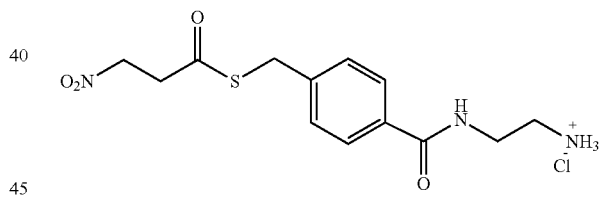

2-(4-(((3-Nitropropanoyl)thio)methyl)benzamido)ethan-1-aminium chloride (30)

Prepared according to the general procedure using 3-nitropropionic acid (51 mg, 0.43 mmol), ABT (93 mg, 0.30 mmol), DMAP (105 mg, 0.86 mmol), EDC·HCl (165 mg, 0.86 mmol) and dichloromethane (1.0 mL). Flash column chromatography (SiO2 30%-50% ethyl acetate in hexanes) yielded the Boc-protected product as a white solid (57 mg, 46%). Bocdeprotection with 4M HCl·dioxane provided the product, which was used without further purification and characterization. Boc-13: 1H NMR (500 MHz, CDCl3) δ 7.76 (d, J=8.0 Hz, 2H), 7.33 (d, J=8.2 Hz, 2H), 7.19 (br s, 1H), 4.97 (br s, 1H), 4.70 (t, J=6.2 Hz, 2H), 4.19 (s, 2H), 3.54 (q, 5.2 Hz, 2H), 3.40 (m, 2H), 3.25 (t, J=6.2 Hz, 2H), 1.43 (s, 9H); 13C NMR (125 MHz, CDCl3) ppm 194.0, 167.2, 157.6, 140.3, 133.4, 129.0, 127.4 80.1, 69.3, 42.2, 39.9, 39.3, 33.0, 28.3; HRMS (ESI): Exact mass calcd for C18H26N3O6S [M+H]+ 244.0334, found 412.1531.

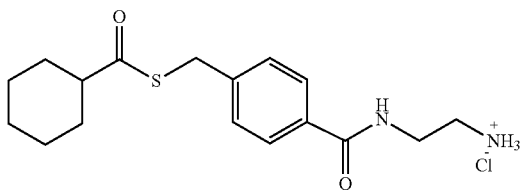 [SMILES: NCCNC(=O)c1ccc(CCSC(=O)C2CCCCC2)cc1 ; Cl]

2-(4-((((Cyclohexanecarbonyl)thio)methyl)benzamido)ethan-1-aminium chloride (31)

Prepared according to the general procedure using cyclohexanecarboxylic acid (53 μL, 0.43 mmol), ABT (93 mg, 0.30 mmol), DMAP (105 mg, 0.86 mmol), EDC·HCl (165 mg, 0.86 mmol) and dichloromethane (1.0 mL). Flash column chromatography (SiO2 30%-50% ethyl acetate in hexanes) yielded the Boc-protected product as a white solid (77 mg, 61%). Boc-deprotection with 4M HCl·dioxane provided the product, which was used without further purification and characterization. Boc-12: 1H NMR (500 MHz, CDCl3) δ 7.72 (d, J=8.1 Hz, 2H), 7.30 (d, J=8.2 Hz, 2H), 7.29 (br s, 1H), 5.15 (br s, 1H), 4.08 (s, 2H), 3.52 (q, 5.2 Hz, 2H), 3.37 (m, 2H), 2.48 (tt, J=11.5, 3.6 Hz, 1H), 1.90 (dd, J=12.9, 3.3 Hz, 2H), 1.76 (dt, J=12.7, 3.4 Hz, 2H), 1.69-1.57 (m, 1H), 1.45 (qd, J=12.0, 3.1 Hz, 2H), 1.40 (s, 9H), 1.31-1.12 (m, 3H); 13C NMR (125 MHz, CDCl3) ppm 202.0, 167.4, 157.4, 141.6, 132.9, 128.8, 127.3, 79.9, 52.7, 41.9, 39.9, 32.3, 29.5, 28.3, 25.5, 25.4; HRMS (ESI): Exact mass calcd for C22H33N2O4S [M+H]+ 421.2161, found 421.2151.

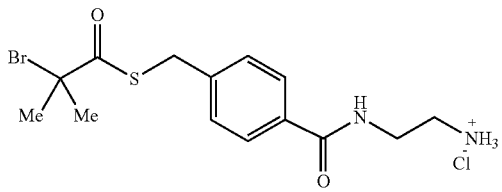 [SMILES: CC(C)(Br)C(=O)SCCc1ccc(C(=O)NCCN)cc1 ; Cl]

2-(4-(((2-Bromo-2-methylpropanoyl)thio)methyl)benzamido)ethan-1-aminium chloride (32)

Prepared according to the general procedure using α-bromoisobutyric acid (72 mg, 0.43 mmol), ABT (93 mg, 0.30 mmol), DMAP (105 mg, 0.86 mmol), EDC·HCl (165 mg, 0.86 mmol) and dichloromethane (1.0 mL). Flash column chromatography (SiO2 30%-50% ethyl acetate in hexanes) yielded the Boc-protected product as a white solid (93 mg, 68%). Boc-deprotection with 4M HCl·dioxane provided the product, which was used without further purification and characterization. Boc-14: 1H NMR (500 MHz, CDCl3) δ 7.74 (d, J=8.0 Hz, 2H), 7.33 (d, J=8.4 Hz, 2H), 7.29 (br s, 1H), 5.16 (br s, 1H), 4.12 (s, 2H), 3.52 (q, 5.3 Hz, 2H), 3.38 (m, 2H), 1.93 (s, 6H), 1.40 (s, 9H); 13C NMR (125 MHz, CDCl3) ppm 199.1, 167.4, 157.5, 140.4, 133.2, 128.9, 127.4, 79.9, 63.9, 42.0, 39.9, 34.2, 31.3 28.3; HRMS (ESI): Exact mass calcd for C19H28BrN2O4S [M+H]+ 459.0953, found 459.0964.

Preparation of DNA Templates for RNAs

The DNA templates were synthesized by using the following primers as previously described[4].

1) Extension (Generation of Fx Derivatives by Extending Different 3'-Ends.

A. Flexizymes

Fx_F:
(SEQ ID NO: 1)
5'-GTAATACGACTCACTATAGGATCGAAAGATTTCCGC-3' eFx_R1:
(SEQ ID NO: 2)
5'-ACCTAACGCTAATCCCCTTTCGGGGCCGCGGAAATCTTTCGATCC-3' dFx_R1:
(SEQ ID NO: 3)
5'-ACCTAACGCCATGTACCCTTTCGGGGATGCGGAAATCTTTCGATCC-3' aFx_R1:
(SEQ ID NO: 4)
5'-ACCTAACGCCACTTACCCTTTCGGGGGTGCGGAAATCTTTCGATCC-3'

0.5 μL of 200 μM Fx_F primer and 0.5 μL of 200 μM of Fx_R1 primer (eFx_R1, dFx_R1, and aFx_R1 were used for eFx, dFx, and aFx generation, respectively) were added to 99 μL of a master mix containing 9.9 μL of 10×PCR buffer (500 mM KCl, 100 mM Tris-HCL (pH 9.0), and 1% of Triton X-100), 0.99 μL of 250 mM MgCl2, 4.95 μL of 5 mM dNTPs, 0.66 μL of Taq DNA polymerase (NEB), and 82.5 μL of water in a PCR tube. The thermocycling conditions were: 1 min at 95° C. followed by 5 cycles of 50° C. for 1 min and 72° C. for 1 min. The sizes of products were checked in 3% (w/v) agarose gel.

2) PCR Amplification

A. Flexizyme

5 μL of the extension product was used as a PCR template. 200 μL of 5× OneTaq® Standard buffer, 20 μL of 10 mM dNTP, 5 μL of 200 μM Fx_T7F primer and 5 μL of 200 μM Fx_R2 (eFx_R2, dFx_R2, and aFx_R2 were used for eFx, dFx, and aFx generation, respectively), 10 μL of OneTaq® polymerase and 755 μL of nuclease-free water was mixed in a 1.5 mL microcentrifuge tube. The mixture was transferred to 10 PCR tubes and the DNA was amplified by the following thermocycling conditions: 1 min at 95° C. followed by 12 cycles of 95° C. for 40 s and 50° C. for 40 s, and 72° C. for 40 s. Products were checked in 3% (w/v) agarose gel.

Fx_T7F:
(SEQ ID NO: 5)
5'-GGCGTAATACGACTCACTATAG-3' eFx_R2:
(SEQ ID NO: 6)
5'-ACCTAACGCTAATCCCCT-3' dFx_R2:
(SEQ ID NO: 7)
5'-ACCTAACGCCATGTACCCT-3' aFx_R2:
(SEQ ID NO: 8)
5'-ACCTAACGCCACTTACCCC-3'

Sequence of the Final DNA Templates Produced by the PCR Reactions eFx
(SEQ ID NO: 9)
5'-GTAATACGACTCACTATAGGATCGAAAGATTTCCGCGGCCCCGAAAG
GGGATTAGCGTTAGGT-3' dFx
(SEQ ID: 10)
5'-TAATACGACTCACTATAGGATCGAAAGATTTCCGCATCCCCGAAAGG
GTACATGGCGTTAGGT-3' aFx
(SEQ ID NO: 11)
5'-GTAATACGACTCACTATAGGATCGAAAGATTTCCGCACCCCCGAAAG
GGGTAAGTGGCGTTAGGT-3'

B. tRNA

The DNA template for tRNA preparation was directly amplified from the full-length oligo by a pair of the primers corresponding to both 5'- and 3'-ends of the template (GluE2_fwd: 5'-GTAATACGACTCACTATAGTCC-3' (SEQ ID NO:19); GluE2_rev: 5'-TGGCGTCCCCTAGGG-GATTCG-3' (SEQ ID NO:20)). 5 µL of the DNA template (100 µM) for tRNA was mixed with 5 µL of 200 µM GluE2_fwd and Glu_E2_rev, 200 µL of 5× HF buffer, 10 µL of Phusion polymerase (NEB), 20 µL of 10 mM dNTPs, and 755 µL of water. The thermocycling conditions were: 1 min at 95° C. followed by 35 cycles of 95° C. for 5 sec, 60° C. for 10 sec, and 72° C. 10 sec, and final elongation at 72° C. for 1 min. The sizes of products were checked in 3% (w/v) agarose gel.

Sequence of the Final DNA Templates Produced by the PCR Reactions

GluE2_GGU
(SEQ ID NO: 12)
5'-GTAATACGACTCACTATAGTCCCCTTCGTCTAGAGGCCCAGGACACC
GCCTTGGTAAGGCGGTAACAGGGGTTCGAATCCCCTAGGGGACGCCA fMet_CAU
(SEQ ID NO: 13)
5'-GTAATACGACTCACTATAGGCGGGGTGGAGCAGCCTGGTAGCTCGTC
GGGCTCATAACCCGAAGATCGTCGGTTCAAATCCGGCCCCCGCAACCA

3) DNA Precipitation

PCR products were combined, extracted using phenol/chloroform/isoamyl alcohol and precipitated and washed with EtOH. Sample were dried at room temperature for 5 min and resuspended in 100 µL nuclease-free water. DNA concentrations were determined spectrophotometrically (Thermo Scientific NanoDrop 2000C spectrophotometer).

In-Vitro Transcription.

The microhelix (5'-rGrGrCrUrCrUrGrUrUrCrGrCrAr-GrArGrCrCrGrCrA-3' (SEQ ID NO:21)) was obtained from Integrated DNA Technologies (IDT) and directly used. Flexizymes and tRNAs were prepared using a HiScribe T7 high yield RNA synthesis kit (NEB). For in vitro transcription, 5 g of DNA template was used with 10 µL of each of OX T7 Reaction Buffer, ATP, CTP, GTP, UTP, T7 RNA polymerase mix, and nuclease-free water up to 100 µL. The mixture was incubated at 37° C. overnight.

Digestion of DNA Templates.

The DNA templates were removed by adding 5 µL of DNase I (NEB) and 20 µL of DNase I reaction buffer into the 100 µL of transcription reaction products. The reaction mixture was incubated for 1 h at 37° C.

Purification of In-Vitro Transcribed RNA.

The digested transcription reactions were mixed with 100 µL 2×RNA loading dye[4], and loaded onto a 15% TBE-Urea gel (Invitrogen). The gel was run in Tris-Borate-EDTA (89 mM Tris, 89 mM boric acid, 2 mM EDTA, and pH 8.3) buffer at 160 V for 2.5 h at room temperature. The gel was placed on a cling film covering a 20 cm×20 cm TLC silica gel glass plate (EMD Millipore) coated with a fluorescent indicator and the transcribed RNAs were visualized by irradiating with UV lamp (260 nm). A sheet of cling film was covered on the gel and the band with desired size was marked on the film. The RNA products were excised from the gel and added to 2 mL of water. The gels were crushed and then shaken in the cold room for 4 h. The gels were transferred to a centrifugal filter (EMD Millipore) and centrifuged at 4,000 g for 2 min. The flow-through was collected and added to the solution of 120 µL of 5 M NaCl and 5 mL of 100% EtOH and. The solution was placed in −20° C. for 16 h and centrifuged at 15,000 g for 45 min at 4° C. The supernatant was removed and the pellet was dried for 5 min at room temperature. The dried RNA pellet was dissolved in nuclease-free water and the concentration was determined from the absorbance measured on a Thermo Scientific NanoDrop 2000C spectrophotometer.

Acylation of Microhelix.

The experiment using microhelix was performed using two flexizymes (eFx and aFx). The coupling reaction of activated ester with microhelix was carried out as follows: 1 µL of 0.5 M HEPES (pH 7.5) or bicine (pH 8.8), 1 µL of 10 µM microhelix, and 3 µL of nuclease-free water were mixed in a PCR tube with 1 µL of 10 M eFx, dFx, and aFx, respectively. The mixture was heated for 2 min at 95° C. and cooled down to room temperature over 5 min. 2 µL of 300 mM MgCl2 was added to the cooled mixture and incubated for 5 min at room temperature. Followed by the incubation of the reaction mixture on ice for 2 min, 2 µL of 25 mM activated ester substrate in DMSO was then added to the reaction mixture. The reaction mixture was further incubated for 6-120 h on ice in cold room.

Acidic PAGE Analysis.

1 µL of crude reaction mixture was aliquoted at a desired time point and the reaction was quenched by the aliquot with 4 µL of acidic loading buffer (150 mM NaOAc, pH 5.2, 10 mM EDTA, 0.02% BPB, 93% formamide). The crude mixture was loaded on 20% polyacrylamide gel containing 50 mM NaOAc (pH 5.2) without further RNA precipitation process. The electrophoresis was carried out in cold room using 50 mM NaOAc (pH 5.2) as a running buffer. The gel was stained with GeRed (Biotium) and visualized on a Bio-Rad Gel Doc XR+. The acylation yield was determined by quantifying the intensity of the microhelix bands using ImageJ (NIH).

Acylation of tRNA.

The acylation reaction of tRNA was carried out as follows: 2 µL of 0.5 M HEPES (pH 7.5), 2 µL of 250 µM tRNA, 2 µL of 250 µM of a Fx selected on the microhelix experiment and 6 µL of nuclease free water were mixed in a PCR tube. The mixture was heated for 2 min at 95° C. and cooled down to room temperature over 5 min. 4 µL of 300 mM MgCl2 was added to the cooled mixture and incubated for 5 min at room temperature. Followed by the incubation of the reaction mixture on ice for 2 min, 4 µL of 25 mM activated ester substrate in DMSO was then added to the reaction mixture. The reaction mixture was further incubated for the optimal time determined on the microhelix experiment on ice in cold room.

Precipitation of tRNA.

Into a 1.5 mL of microcentrifuge tube containing 100 L of EtOH and 40 μL of 0.3 M NaOAc (pH 5.2), the mixture from coupling reaction was added and mixed to quench the reaction. The mixture was centrifuged at 21,000 g for 15 min at room temperature and the supernatant was removed. The RNA pellet was washed with 50 L of 70% (v/v) ethanol containing 0.1 M NaOAc (pH 5.2) was resuspended into the solution by vortexing and subsequently centrifuged at 21,000 g for 5 min at room temperature. The washing step was repeated twice. After the supernatant was discarded, the pellet was resuspended in 50 μL of 70% (v/v) ethanol resuspended and centrifuged at 21,000 g for 3 min at room temperature. The supernatant was removed and the pellet was dissolved by 1 μL of 1 mM NaOAc (pH 5.2).

In-Vitro Translation.

The produced using the reprogrammed genetic code approach was produced by the PURExpress (Δ aa, Δ tRNA, E6840) system. 6 μg of the misacylted tRNA dissolved in 1 μL of 1 mM NaOAc (pH 5.2) was added into a 9 μL solution mixture containing a 2 μL of Solution A, 1 μL of tRNA, 3 μL of Solution B, 1 μL of DNA template (130 ng/μL), 1 μL of nuclease-free water, and 1 μL of 5 mM amino acid mixtures in 20 mM Tris buffer (pH 7.5). The reaction mixture was incubated in 37° C. for 4 h.

Peptide Purification.

The peptides produced in the PURExpress were produced by using an affinity tag purification technique. 2 μL of MagStrep (type3) XT beads 5% suspension (iba) was washed twice with 200 and 100 μL of Strep-Tactin XT Wash buffer (1×) in a 1.5 mL microcentrifuge tube. The buffer was discarded by placing the tube on a magnetic rack. 10 μL of PURExpress reaction material was mixed with the wet magnetic beads and the tube containing the mixture was placed on ice for 30 min. The mixture was vortexed for 5 sec every 10 min. The tube was placed back on a magnetic rack and the supernatant was removed. The beads were washed twice with 200 and 100 μL of the wash buffer and the buffer was discarded. The beads were mixed with 10 μL of 0.1% SDS solution (v/v in water) and transferred to a PCR tube and heated at 95° C. for 2 min. The SDS solution was separated from the beads on a 96-well magnetic rack and further analyzed by mass spectrum.

For calculation of peptide (NH2-WSHPQFEKST-OH; SEQ ID NO:14) yield, the his-tagged enzymes resent in the PURExpress were removed using Ni-NTA-coated magnetic beads (His-Select® Nickel magnetic agarose beads, Sigma). 2 μL of beads suspension (iba) was washed twice with 200 and 100 μL of Strep-Tactin XT Wash buffer (1×) in a 1.5 mL microcentrifuge tube. The reaction mixture was added to the beads and vortexed for 10 min at room temperature. The beads were washed on a magnetic rack and the supernatant was collected. The supernatant was added to a C18 spin column (Pierce C18 columns, Thermo Fisher Scientific) to remove residual nucleic acids and buffers. The column was washed twice with 20% MeCN/water (5% TFA) solution. The peptide was eluted using 80% MeCN/water (5% TFA) solution.

Characterization of Peptides.

1.5 μL of the peptides purified by the strep affinity tag was mixed on a MALDI plate with 1 μL of saturated α-cyano-4-hydroxycinnamic acid (CHCA) in THE containing 0.1% TFA. The samples were dried at room temperature for 30 min. MALDI-TOF mass spectra of the peptides were obtained on a Bruker Autoflex III using the positive reflectron mode.

Example 4—Further Example if Substrate Synthesis

Materials and Method

All reagents and solvents were commercial grade and purified prior to use when necessary. Dichloromethane was dried by passage through a column of activated alumina Tert-butyl (2-(4-(mercaptomethyl)benzamido)ethyl) carbamate (ABT) was prepared according to the standard procedure.[3] All organic solutions were dried over $MgSO_4$. Thin layer chromatography (TLC) was performed using glass-backed silica gel (250 m) plates. Flash chromatography was performed on a Biotage Isolera One automated purification system. UV light, and/or the use of KMnO4 were used to visualize products.

Nuclear magnetic resonance spectra (NMR) were acquired on a Bruker Advance III-500 (500 MHz) or Varian Unity 500 (500 MHz) instrument and processed by MestReNova. Chemical shifts are measured relative to residual solvent peaks as an internal standard set to δ 7.26 and δ 77.0 ($CDCl_3$), and δ 2.50 and δ 39.5 (DMSO-$d_6$). Mass spectra were recorded on a Bruker AmaZon SL or Waters Q-TOF Ultima (ESI) and Impact-II or Waters 70-VSE (EI), spectrometers by use of the ionization method noted.

General Procedure A for Formation of Dinitrobenzyl Esters & Boc Deprotection.

To a glass vial with a stir bar was added carboxylic acid (1 equiv.), $CH_2C2$ (1.0 M), triethylamine (1.5 equiv.), and 3,5-dinotrobenzyl chloride (1.2 equiv.). After stirring for 16 h at room temperature, the reaction mixture was diluted with EtOAc and washed with HCl (0.5 M aq.), $NaHCO_3$(4% (w/v) in water), brine, and dried over $MgSO_4$. The organic phase was concentrated to provide the crude product. The product was purified by flash column chromatography. The resulting fraction containing product was collected in a 100 mL flask and the solvent was removed under reduced pressure. 2 mL of HCl (4N in anhydrous dioxane) was added and let stir for 1 h in room temperature. The resulting product was transferred to a 20 mL glass vial and dried under high vacuum overnight to give final product.

General Procedure B for Formation of Dinitrobenzyl Esters & Boc Deprotection.

To a flame-dried vial with septa and stir bar was added carboxylic acid (1.0 equiv.), 1-ethyl-3-(3-dimethylaminopropyl) carbodiimide hydrochloride (EDCI) (2.0 equiv.), dimethylamino pyridine (2.0 equiv.), evacuated and flushed with $N_{2(g)}$ three times, then anhydrous $CH_2C2$ (0.1 M) was added via syringe. The reaction was then let stir for 10 minutes before dinitrobenzyl alcohol (0.1M in anhydrous $CH_2Cl_2$) was added dropwise via syringe over 60 seconds. The reaction was then stirred at 22° C. for 16 h. The reaction was diluted with DCM, added to a separatory funnel, rinsed with HCl (1.0 M aq.), $H_2O$, $NaHCO_3$(3.0 M aq.), dried with $NaSO_4$, filtered, then silica ($SiO_2$) was added and condensed under reduced pressure. The compound/Silica mixture was then dry loaded and purified by silica gel column chromatography [Solvent System:Hexanes-Ethyl Acetate; 9:1-2:8].

The resulting oil or solid was placed in a 20 mL scintillation vial with stir bar and 2 mL of HCl (4N in anhydrous Dioxane) was added and let stir for 4 h. The solution condensed under reduced pressure, then 5 mL of diethyl ether was added and the heterogenous mixture was sonicated for 5 minutes. The mixture was filtered, and the filter cake rinsed with diethyl ether. The solid was collected and dried under vacuum to give final product.

General Procedure C for Formation of 4-((2-aminoethyl) carbamoyl)benzyl Thioates & Boc Deprotection.

To a flame-dried vial with septa and stir bar was added carboxylic acid (1.0 equiv.), 1-ethyl-3-(3-dimethylaminopropyl) carbodiimide hydrochloride (EDCI) (2.0 equiv.), dimethylamino pyridine (2.0 equiv.), evacuated and flushed with $N_{2(g)}$ three times, then anhydrous $CH_2Cl_2$ (0.1 M) was added via syringe. The reaction was then let stir for 10 minutes before Tert-butyl (2-(4-(mercaptomethyl)benzamido)ethyl) carbamate (0.1M in anhydrous $CH_2Cl_2$) was added dropwise via syringe over 60 seconds. The reaction was then stirred at 22° C. for 16 h. The reaction was diluted with DCM, added to a separatory funnel, rinsed with HCl (1.0 M aq.), $H_2O$, $NaHCO_3$(3.0 M aq.), dried with $NaSO_4$, filtered, then silica ($SiO_2$) was added and condensed under reduced pressure. The compound/Silica mixture was then dry loaded and purified by silica gel column chromatography [Solvent System:Hexanes-Ethyl Acetate; 8:3-1:9].

The resulting oil or solid was placed in a 20 mL scintillation vial with stir bar and 2 mL of HCl (4N in anhydrous Dioxane) was added and let stir for 4 h. The solution condensed under reduced pressure, then 5 mL of diethyl ether was added and the heterogenous mixture was sonicated for 5 minutes. The mixture was filtered, and the filter cake rinsed with diethyl ether. The solid was collected and dried under vacuum to give final product.

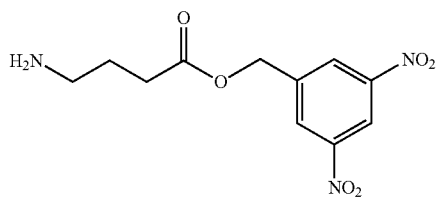 [SMILES: NCCCC(=O)OCCc1cc([N+](=O)[O-])cc([N+](=O)[O-])c1]

3,5-dinitrobenzyl-amino-4-butanoate

Prepared according to general procedure A using N-Boc-4-aminobutanoic acid (61.5 mg, 0.33 mmol), triethylamine (70 μL, 0.50 mmol), 3,5-dinitrobenzyl chloride (86 mg, 0.40 mmol) and dichloromethane (0.5 mL). The product was obtained as a white powder (65 mg, 70%). $^1$H NMR (500 MHz, 500 MHz, DMSO-d$_6$) δ 8.80 (t, J=2.3 Hz, 1H), 8.59 (d, J=2.1 Hz, 2H), 5.37 (s, 2H), 2.86-2.79 (m, 2H), 2.58 (t, J=7.5 Hz, 2H), 1.85 (q, J=7.6, 7.7, 2H); $^{13}$C NMR (125 MHz, DMSO-d$_6$) ppm 172.4, 148.5 (2C), 141.0, 128.7 (2C), 118.6, 64.2, 38.4, 30.6, 22.7; HRMS (EI): Exact mass calcd for $C_{11}H_{13}N_3O_6$ [M+H]$^+$ 204.24, found 204.12.

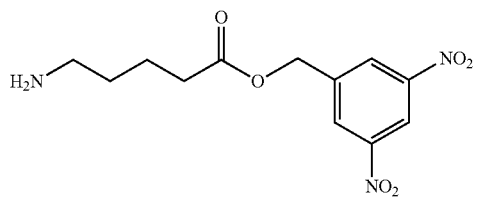 [SMILES: NCCCCC(=O)OCCc1cc([N+](=O)[O-])cc([N+](=O)[O-])c1]

3,5-dinitrobenzyl 5-aminopentanoate

Prepared according to general procedure A using Boc-5-Ava-OH (72 mg, 0.33 mmol), triethylamine (70 μL, 0.50 mmol), 3,5-dinitrobenzyl chloride (86 mg, 0.40 mmol) and dichloromethane (0.5 mL). The product was obtained as a yellow oil (51 mg, 53%). $^1$H NMR (500 MHz, DMSO-d6) δ 8.80 (t, J=2.1 Hz, 1H), 8.67 (d, J=2.0 Hz, 2H), 5.36 (s, 2H), 2.82-2.77 (m, 2H), 2.49 (t, J=7.2 Hz, 2H), 1.66-1.54 (m, 4H); $^{13}$C NMR (125 MHz, DMSO-d$_6$) ppm 172.8, 148.5 (2C), 141.0, 128.6 (2C), 118.5, 64.0, 38.8, 33.0, 26.8, 21.7; HRMS (CI): Exact mass calcd for $C_{12}H_{16}N_3O_6$ [M+H]$^+$ 298.27, found 298.11.

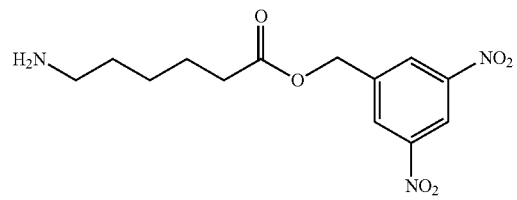 [SMILES: NCCCCCC(=O)OCCc1cc([N+](=O)[O-])cc([N+](=O)[O-])c1]

3,5-dinitrobenzyl 6-aminohexanoate

Prepared according to general procedure A using Boc-5-Ahx-OH (76 mg, 0.33 mmol), triethylamine (70 μL, 0.50 mmol), 3,5-dinitrobenzyl chloride (86 mg, 0.40 mmol) and dichloromethane (0.5 mL). The product was obtained as a white solid (64 mg, 62%). $^1$H NMR (500 MHz, CDCl$_3$) δ 8.80 (t, J=2.1 Hz, 1H), 8.66 (d, J=2.0 Hz, 2H), 5.36 (s, 2H), 2.78-2.72 (m, 2H), 2.45 (t, J=7.6 Hz, 2H), 1.62-1.53 (m, 4H), 1.38-1.31 (m, 2H); $^{13}$C NMR (125 MHz, DMSO-d$_6$) ppm 173.0, 148.5 (2C), 141.9, 128.5 (2C), 118.5, 63.9, 38.9, 33.5, 27.0, 25.7, 24.2; HRMS (CI): Exact mass calcd for $C_{13}H_{17}N_3O_6$ [M+H]$^+$ 312.29, found 312.13.

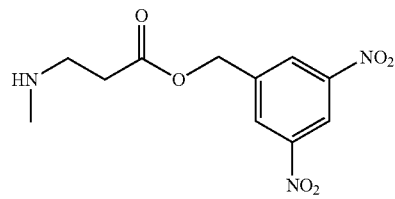 [SMILES: CNCCC(=O)OCCc1cc([N+](=O)[O-])cc([N+](=O)[O-])c1]

3,5-dinitrobenzyl 4-(methylamino)butanoate

Prepared according to general procedure A using 4-((boc-(methyl)amino)butanoic acid (67 mg, 0.33 mmol), triethylamine (70 μL, 0.50 mmol), 3,5-dinitrobenzyl chloride (86 mg, 0.40 mmol) and dichloromethane (0.5 mL). The product was obtained as a yellow powder (70 mg, 72%). $^1$H NMR (500 MHz, DMSO-d$_6$) δ 8.72 (s, 1H), 8.59 (s, 2H), 4.76 (s, 2H), 1.82 (q, J=7.5, 7.5 Hz, 2H); $^{13}$C NMR (125 MHz, DMSO-d$_6$) ppm 173.9, 148.4, 147.9, 128.6, 126.7 (2C), 117.4, 61.5, 47.9, 32.7 30.9, 21.3; HRMS (EI): Exact mass calcd for $C_{12}H_{15}N_3O_6$ [M+H]$^+$ 298.10, found 298.14.

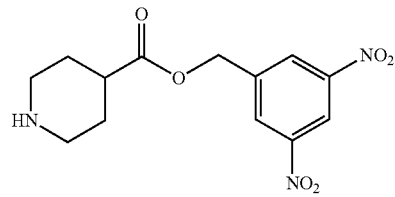 [SMILES: O=C(OCCc1cc([N+](=O)[O-])cc([N+](=O)[O-])c1)C1CCNCC1]

3,5-dinitrobenzyl piperidine-4-carboxylate

Prepared according to general procedure A using N-Boc-piperidine-4-carboxylic acid (76 mg, 0.33 mmol), triethylamine (70 μL, 0.50 mmol), 3,5-dinitrobenzyl chloride (86 mg, 0.40 mmol) and dichloromethane (0.5 mL). The product was obtained as a yellow powder (43 mg, 46%). $^1$H NMR (500 MHz, 500 MHz, DMSO-$d_6$) δ 8.77 (s, 1H), 8.59 (s, 2H), 4.76 (s, 2H), 3.20 (d, J=6.8, 2H), 2.90 (q, J=11.4, 10.9 Hz, 2H), 2.60-2.54 (m, 1H), 2.14 (s, 1H), 1.97 (d, J=14.9, 2H), 1.73 (qd, J=11.4, 14.9, 4.0, 2H); $^{13}$C NMR (125 MHz, DMSO-d6) ppm 175.2, 148.4, 148.0, 129.7, 126.7 (2C), 117.3, 61.5, 42.7 (2C), 38.1, 24.9 (2C); HRMS (EI): Exact mass calcd for $C_{13}H_{15}N_3O_6$ [M+H]$^+$ 310.10, found 310.02.

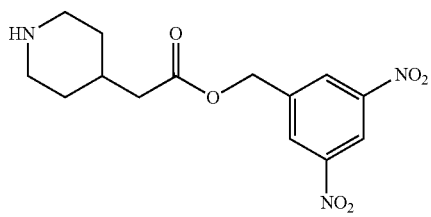 [SMILES: O=C(CC1CCNCC1)OCCc1cc([N+](=O)[O-])cc([N+](=O)[O-])c1]

3,5-dinitrobenzyl 2-(piperidin-4-yl)acetate

Prepared according to general procedure A using N-Boc-4-piperidineacetic acid (80 mg, 0.33 mmol), triethylamine (70 μL, 0.50 mmol), dinitrobenzyl chloride (86 mg, 0.40 mmol) and dichloromethane (0.3 mL). The product was obtained as a yellow oil (66 mg, 62%). $^1$H NMR (500 MHz, DMSO-$d_6$) δ; 8.72 (t, J=2.0 Hz, 1H), 8.59 (d, J=1.7 Hz, 2H), 3.15 (d, J=12.4 Hz, 2H), 2.79 (td, J=12.7, 2.8 Hz, 2H), 2.37 (d, 2H), 1.99-1.90 (m, 1H), 1.74 (d, J=14.0 Hz, 2H), 1.33 (qd, J=12.8, 4.1 Hz, 2H); $^{13}$C NMR (125 MHz, DMSO-$d_6$) ppm 171.7, 148.5 (2C), 141.0, 128.5 (2C), 118.5, 64.0, 43.2 (2C), 30.6, 28.4 (2C); HRMS (EI): Exact mass calcd for $C_{14}H_{17}N_3O_6$ [M+H]$^+$ 324.31, found 324.09.

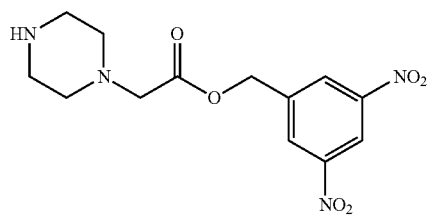 [SMILES: O=C(CN1CCNCC1)OCc1cc([N+](=O)[O-])cc([N+](=O)[O-])c1]

3,5-dinitrobenzyl 2-(piperazin-1-yl)acetate

Prepared according to general procedure A using 2-(4-Boc-1-piperazinyl)acetic acid (80 mg, 0.33 mmol), triethylamine (70 μL, 0.50 mmol), 3,5-dinitrobenzyl chloride (86 mg, 0.40 mmol) and dichloromethane (0.3 mL). The product was obtained as a white powder (87 mg, 82%). $^1$H NMR (500 MHz, DMSO-$d_6$) δ; 2.69 (t, J=4.9 Hz, 4H), 2.98 (t, J=5.1 Hz, 4H), 3.41 (s, 2H), 5.31 (s, 2H), 8.61 (d, J=1.1 Hz, 2H), 8.73 (t, J=2.1, 1H); $^{13}$C NMR (125 MHz, DMSO-$d_6$) 170.0, 148.5 (2C), 140.9, 128.8 (2C), 118.8, 64.0, 57.9, 49.1 (2C), 43.3 (2C); HRMS (EI): Exact mass calcd for $C_{13}H_{16}N_4O_6$ [M+H]$^+$ 325.11, found 325.22.

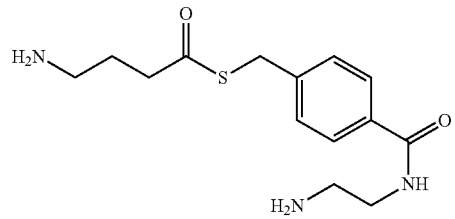 [SMILES: NCCCC(=O)SCc1ccc(C(=O)NCCN)cc1]

S-(4-((2-aminoethyl)carbamoyl)benzyl) 4-aminobutanethioate

Prepared according to general procedure C using 7-((tert-butoxycarbonyl)amino) butanoic acid (50.8 mg, 0.25 mmol), 1-ethyl-3-(3-dimethylaminopropyl) carbodiimide hydrochloride (EDCI) (95.9 mg, 0.50 mmol), dimethylamino pyridine (61.1 mg, 0.50 mmol), tert-butyl (2-(4-(mercaptomethyl)benzamido)ethyl) carbamate (84.6 mg, 0.25 mmol). The product was obtained as a white powder (40.7 mg, 55%). Silica gel column chromatography [Solvent System:Hexanes-Ethyl Acetate; 1:1, Rf=0.1]. $^1$H NMR (500 MHz, 500 MHz, DMSO-$d_6$) $^{13}$C NMR (125 MHz, DMSO-$d_6$) HRMS (EI): Exact mass calcd for $C_{14}H_{22}N_3O_2S$ [M+H]$^+$ 296.1433, found 296.1435.

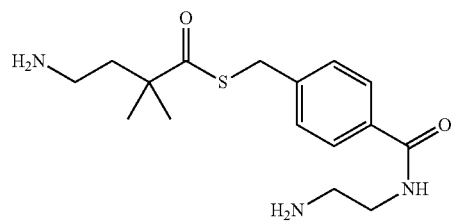 [SMILES: CC(C)(CCN)C(=O)SCc1ccc(C(=O)NCCN)cc1]

S-(4-((2-aminoethyl)carbamoyl)benzyl) 4-amino-2,2-dimethylbutanethioate

Prepared according to general procedure C using 4-((tert-butoxycarbonyl)amino)-2,2-dimethylbutanoic acid (57.8 mg, 0.25 mmol), 1-ethyl-3-(3-dimethylaminopropyl) carbodiimide hydrochloride (EDCI) (95.9 mg, 0.50 mmol), dimethylamino pyridine (61.1 mg, 0.50 mmol), tert-butyl (2-(4-(mercaptomethyl)benzamido)ethyl) carbamate (84.6 mg, 0.25 mmol). The product was obtained as a white powder (51.7 mg, 64%). Silica gel column chromatography [Solvent System:Hexanes-Ethyl Acetate; 1:1, Rf=0.1]. $^1$H NMR (500 MHz, 500 MHz, DMSO-$d_6$) 13C NMR (125 MHz, DMSO-$d_6$) HRMS (EI): Exact mass calcd for $C_{16}H_{25}N_3O_2S$ [M+H]$^+$ 323.1667, found 323.1669.

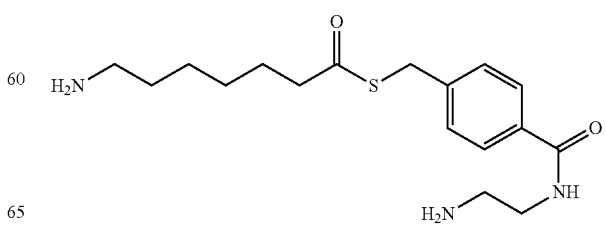

S-(4-((2-aminoethyl)carbamoyl)benzyl) 7-aminoheptanethioate

Prepared according to general procedure C using 7-((tert-butoxycarbonyl)amino) heptanoic acid (105.5 mg, 0.43 mmol), 1-ethyl-3-(3-dimethylaminopropyl) carbodiimide hydrochloride (EDCI) (165.1 mg, 0.86 mmol), dimethylamino pyridine (105.2 mg, 0.86 mmol), tert-butyl (2-(4-(mercaptomethyl)benzamido)ethyl) carbamate (145 mg, 0.43 mmol). The product was obtained as a white powder (133.7 mg, 92%). Silica gel column chromatography [Solvent System:Hexanes-Ethyl Acetate; 1:1, Rf=0.1]. $^1$H NMR (500 MHz, 500 MHz, DMSO-$d_6$) $^{13}$C NMR (125 MHz, DMSO-$d_6$) HRMS (EI): Exact mass calcd for $C_{17}H_{28}N_3O_2S$ [M+H]$^+$ 338.1902, found 338.1902.

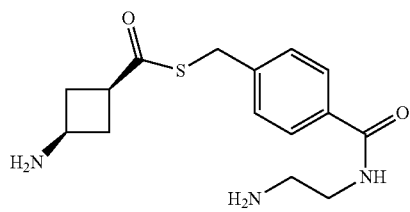 [SMILES: NCCNC(=O)c1ccc(CSC(=O)[C@H]2C[C@@H](N)C2)cc1]

S-(4-((2-aminoethyl)carbamoyl)benzyl) (1s,3s)-3-aminocyclobutane-1-carbothioate Prepared according to general procedure C using (1s,3s)-3-((tert-butoxycarbonyl)amino)cyclobutane-1-carboxylic acid (92.5 mg, 0.43 mmol), 1-ethyl-3-(3-dimethylaminopropyl) carbodiimide hydrochloride (EDCI) (165.1 mg, 0.86 mmol), dimethylamino pyridine (105.2 mg, 0.86 mmol), tert-butyl (2-(4-(mercaptomethyl)benzamido)ethyl) carbamate (145 mg, 0.43 mmol). The product was obtained as a white powder (103.3 mg, 78%). Silica gel column chromatography [Solvent System:Hexanes-Ethyl Acetate; 1:1, Rf=0.1]. $^1$H NMR (500 MHz, 500 MHz, DMSO-$d_6$) $^{13}$C NMR (125 MHz, DMSO-d6) HRMS (EI): Exact mass calcd for $C_{15}H_{22}N_3O_2S$ [M+H]$^+$ 308.1433, found 308.1437.

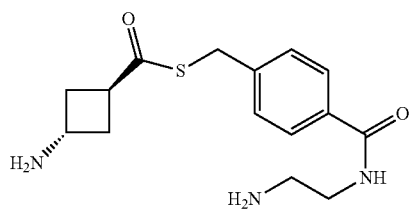 [SMILES: NCCNC(=O)c1ccc(CSC(=O)[C@H]2C[C@H](N)C2)cc1]

S-(4-((2-aminoethyl)carbamoyl)benzyl) (1r,3r)-3-aminocyclobutane-1-carbothioate Prepared according to general procedure C using (1r,3r)-3-((tert-butoxycarbonyl)amino)cyclobutane-1-carboxylic acid (92.9 mg, 0.43 mmol), 1-ethyl-3-(3-dimethylaminopropyl) carbodiimide hydrochloride (EDCI) (165.6 mg, 0.86 mmol), dimethylamino pyridine (105.4 mg, 0.86 mmol), tert-butyl (2-(4-(mercaptomethyl)benzamido)ethyl) carbamate (145 mg, 0.43 mmol). The product was obtained as a white powder (100.7 mg, 76%). Silica gel column chromatography [Solvent System:Hexanes-Ethyl Acetate; 1:1, Rf=0.1]. $^1$H NMR (500 MHz, 500 MHz, DMSO-$d_6$) $^{13}$C NMR (125 MHz, DMSO-$d_6$) HRMS (EI): Exact mass calcd for $C_{15}H_{22}N_3O_2S$ [M+H]$^+$ 308.1433, found 308.1436.

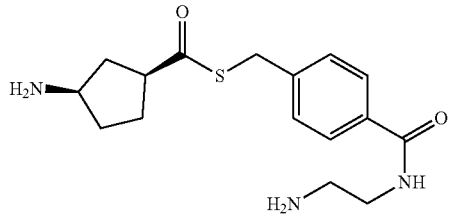 [SMILES: NCCNC(=O)c1ccc(CSC(=O)[C@H]2CC[C@@H](N)C2)cc1]

S-(4-((2-aminoethyl)carbamoyl)benzyl) (1S,3R)-3-aminocyclopentane-1-carbothioate Prepared according to general procedure C using (1S,3R)-3-((tert-butoxycarbonyl)amino)cyclopentane-1-carboxylic acid (98.6 mg, 0.43 mmol), 1-ethyl-3-(3-dimethylaminopropyl) carbodiimide hydrochloride (EDCI) (165.1 mg, 0.86 mmol), dimethylamino pyridine (105.2 mg, 0.86 mmol), tert-butyl (2-(4-(mercaptomethyl)benzamido)ethyl) carbamate (145 mg, 0.43 mmol). The product was obtained as a white powder (91.4 mg, 66%). Silica gel column chromatography [Solvent System:Hexanes-Ethyl Acetate; 1:1, Rf=0.1]. $^1$H NMR (500 MHz, 500 MHz, DMSO-$d_6$) $^{13}$C NMR (125 MHz, DMSO-$d_6$) HRMS (EI): Exact mass calcd for $C_{16}H_{24}N_3O_2S$ [M+H]$^+$ 322.1589 found 322.1591.

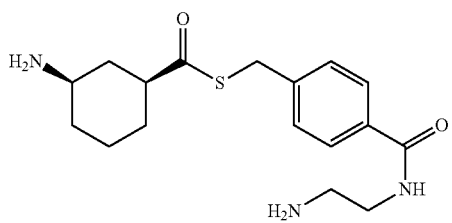 [SMILES: NCCNC(=O)c1ccc(CSC(=O)[C@H]2CCC[C@@H](N)C2)cc1]

S-(4-((2-aminoethyl)carbamoyl)benzyl) (1S,3R)-3-aminocyclohexane-1-carbothioate Prepared according to general procedure C using (1S,3R)-3-((tert-butoxycarbonyl)amino)cyclohexane-1-carboxylic acid (104.6 mg, 0.43 mmol), 1-ethyl-3-(3-dimethylaminopropyl) carbodiimide hydrochloride (EDCI) (165.1 mg, 0.86 mmol), dimethylamino pyridine (105.2 mg, 0.86 mmol), tert-butyl (2-(4-(mercaptomethyl)benzamido)ethyl) carbamate (145 mg, 0.43 mmol). The product was obtained as a white powder (99.7 mg, 69%). Silica gel column chromatography [Solvent System:Hexanes-Ethyl Acetate; 1:1, Rf=0.1]. $^1$H NMR (500 MHz, 500 MHz, DMSO-$d_6$) $^{13}$C NMR (125 MHz, DMSO-$d_6$) HRMS (EI): Exact mass calcd for $C_{17}H_{26}N_3O_2S$ [M+H]$^+$ 336.1746, found 336.1746.

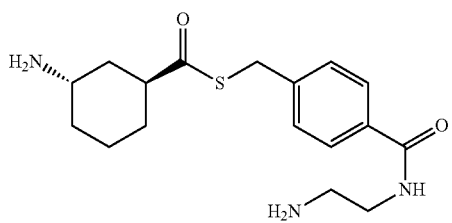 [SMILES: NCCNC(=O)c1ccc(CSC(=O)[C@H]2CCC[C@H](N)C2)cc1]

S-(4-((2-aminoethyl)carbamoyl)benzyl) (1S,3S)-3-aminocyclohexane-1-carbothioate Prepared according to general procedure C using (1S,3S)-3-((tert-butoxycarbonyl)amino)cyclohexane-1-carboxylic acid 104.1 mg, 0.43 mmol), 1-ethyl-3-(3-dimethylaminopropyl) carbodiimide hydrochloride (EDCI) (165.1 mg, 0.86 mmol), dimethylamino pyridine (105.2 mg, 0.86 mmol), tert-butyl (2-(4-(mercaptomethyl)benzamido)ethyl) carbamate (145 mg, 0.43 mmol). The product was obtained as a yellow powder (95.4 mg, 62%). Silica gel column chromatography [Solvent System:Hexanes-Ethyl Acetate; 1:1, Rf=0.1]. $^1$H NMR (500 MHz, 500 MHz, DMSO-d$_6$) $^{13}$C NMR (125 MHz, DMSO-d$_6$) HRMS (EI): Exact mass calcd for $C_{17}H_{26}N_3O_2S$ [M+H]$^+$ 336.1746, found 336.1749.

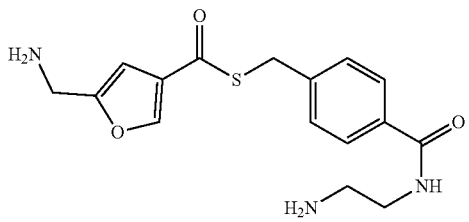 [SMILES: NCCNC(=O)c1ccc(CSC(=O)c2coc(CN)c2)cc1]

S-(4-((2-aminoethyl)carbamoyl)benzyl) 5-(aminomethyl)furan-3-carbothioate

Prepared according to general procedure C using 5-(((tert-butoxycarbonyl)amino)methyl)furan-3-carboxylic acid (60.3 mg, 0.25 mmol), 1-ethyl-3-(3-dimethylaminopropyl) carbodiimide hydrochloride (EDCI) (95.9 mg, 0.50 mmol), dimethylamino pyridine (61.1 mg, 0.50 mmol), tert-butyl (2-(4-(mercaptomethyl)benzamido)ethyl) carbamate (84.6 mg, 0.25 mmol). The product was obtained as a yellow powder (68.5 mg, 82%). Silica gel column chromatography [Solvent System:Hexanes-Ethyl Acetate; 1:1, Rf=0.1]. $^1$H NMR (500 MHz, 500 MHz, DMSO-d6)$^{13}$C NMR (125 MHz, DMSO-d$_6$) HRMS (EI): Exact mass calcd for $C_{16}H_{20}N_3O_3S$ [M+H]$^+$ 334.1225 found 334.1225.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

---

We claim:

1. An acylated tRNA molecule having a formula defined as:

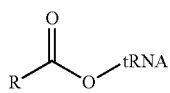

wherein:
tRNA is a transfer RNA linked via a 3' terminal ribonucleotide;
R is selected from the group consisting of cycloalkyl substituted with amino; heterocycloalkyl; and alkylheterocycloalkyl; and
wherein R has a primary amine group or a secondary amine group in a gamma position or a delta position.

2. The acylated tRNA molecule of claim 1, wherein R is the cycloalkyl substituted with amino.

3. The acylated tRNA molecule of claim 1, wherein R is selected from the group consisting of aminocyclobutyl, aminocyclopentyl, and aminocyclohexyl.

4. The acylated tRNA molecule of claim 1, wherein R is selected from the group consisting of

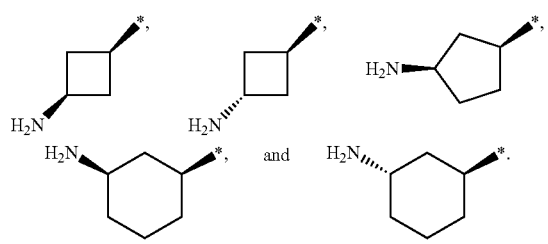

5. The acylated tRNA molecule of claim 1, wherein R comprises a cyclic secondary amine.

6. The acylated tRNA molecule of claim 1, wherein R comprises a piperidinyl or piperazinyl.

7. The acylated tRNA molecule of claim 1, wherein R is selected from the group consisting of piperidin-4-yl, (piperidin-4-yl)methyl, piperazin-4-yl, and (piperazin-4-yl)methyl.

8. A method for preparing a sequence defined polymer, wherein the sequence defined polymer is prepared via translating an mRNA comprising a codon corresponding to an anticodon of the acylated tRNA molecule of claim 1 and the R group of the acylated tRNA molecule is incorporated in the sequence defined polymer during translation of the mRNA.

9. The method of claim 8, wherein the method is performed in vitro.

10. The method of claim 8, wherein the method is performed in vivo.

11. The method of claim 8, wherein the codon is the start codon (AUG) of the mRNA.

12. The method of claim 8, wherein the codon is selected from a codon for threonine, a codon for isoleucine, and a codon for alanine.

13. The method of claim 8, wherein the sequence defined polymer is a polymer selected from γ-amino acid polymer or δ-amino acid polymers.

14. A method for preparing an acylated tRNA molecule having a formula defined as:

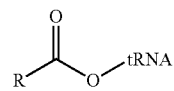

wherein:
tRNA is a transfer RNA linked via a 3' terminal ribonucleotide; and
R is selected from the group consisting of cycloalkyl substituted with amino; heterocycloalkyl; and alkylheterocycloalkyl; and wherein R has a primary amine group or a secondary amine group in a gamma position or a delta position;
the method comprising reacting in a reaction mixture:
(i) a flexizyme (Fx);
(ii) the tRNA molecule; and
(iii) a donor molecule having a formula:

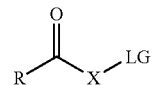

wherein:
R is as defined above;
LG is a leaving group;
X is O or S; and the Fx catalyzes an acylation reaction between the 3' terminal ribonucleotide of the tRNA and the donor molecule to prepare the acylated tRNA molecule.

15. The method of claim 14, wherein the Fx is selected from the group consisting of aFx, dFx, and eFx.

16. The method of claim 14, wherein the tRNA comprises an anticodon selected from the anticodon CAU, the anticodon GGU, the anticodon GAU, or the anticodon GGC.

17. The method of claim 14, wherein LG comprises a cyanomethyl moiety and the donor molecule comprises a cyanomethylester (CME).

18. The method of claim 14, wherein LG comprises a dinitrobenzyl moiety and the donor molecule comprises a dinitrobenzylester (DNB).

19. The method of claim 14, wherein LG comprises a (2-aminoethyl)amidocarboxybenzyl moiety and the donor molecule comprises a (2-aminoethyl)amidocarboxybenzyl thioester (ABT).

20. The method of claim 14, wherein the method is performed under reaction conditions such that at least about 50% of the tRNA in the reaction mixture is acylated after reacting the reaction mixture for 120 hours.

* * * * *

UNITED STATES PATENT AND TRADEMARK OFFICE
CERTIFICATE OF CORRECTION

PATENT NO. : 11,814,621 B2
APPLICATION NO. : 15/734182
DATED : November 14, 2023
INVENTOR(S) : Michael Christopher Jewett et al.

It is certified that error appears in the above-identified patent and that said Letters Patent is hereby corrected as shown below:

On the Title Page

Item (71) Applicants should appear as follows:
--Northwestern University, Evanston, IL (US)
The Board of Trustees of the University of Illinois, Urbana, IL (US)--.

In the Claims

Claim 13, Column 72, Line 34, "$\gamma$-amino acid polymer" should be --$\gamma$-amino acid polymers--.

Signed and Sealed this
Twenty-seventh Day of February, 2024

Katherine Kelly Vidal
*Director of the United States Patent and Trademark Office*

SEQUENCE LISTING

```
<160> NUMBER OF SEQ ID NOS: 22

<210> SEQ ID NO 1
<211> LENGTH: 36
<212> TYPE: DNA
<213> ORGANISM: Artificial Sequence
<220> FEATURE:
<223> OTHER INFORMATION: synthetic

<400> SEQUENCE: 1
gtaatacgac tcactatagg atcgaaagat ttccgc                           36

<210> SEQ ID NO 2
<211> LENGTH: 45
<212> TYPE: DNA
<213> ORGANISM: Artificial Sequence
<220> FEATURE:
<223> OTHER INFORMATION: syntehtic

<400> SEQUENCE: 2
acctaacgct aatcccttt cggggccgcg gaaatctttc gatcc                  45

<210> SEQ ID NO 3
<211> LENGTH: 46
<212> TYPE: DNA
<213> ORGANISM: Artificial Sequence
<220> FEATURE:
<223> OTHER INFORMATION: synthetic

<400> SEQUENCE: 3
```
acctaacgcc atgtaccctt tcggggatgc ggaaatcttt cgatcc        46

<210> SEQ ID NO 4
<211> LENGTH: 47
<212> TYPE: DNA
<213> ORGANISM: Artificial Sequence
<220> FEATURE:
<223> OTHER INFORMATION: synthetic

<400> SEQUENCE: 4
acctaacgcc acttacccct ttcggggtg cggaaatctt tcgatcc        47

<210> SEQ ID NO 5
<211> LENGTH: 22
<212> TYPE: DNA
<213> ORGANISM: Artificial Sequence
<220> FEATURE:
<223> OTHER INFORMATION: synthetic

<400> SEQUENCE: 5
ggcgtaatac gactcactat ag                                  22

<210> SEQ ID NO 6
<211> LENGTH: 18
<212> TYPE: DNA
<213> ORGANISM: Artificial Sequence
<220> FEATURE:
<223> OTHER INFORMATION: synthetic

<400> SEQUENCE: 6
acctaacgct aatcccct                                       18

<210> SEQ ID NO 7
<211> LENGTH: 19
<212> TYPE: DNA
<213> ORGANISM: Artificial Sequence
<220> FEATURE:
<223> OTHER INFORMATION: syntehtic

<400> SEQUENCE: 7
acctaacgcc atgtaccct                                      19

<210> SEQ ID NO 8
<211> LENGTH: 19
<212> TYPE: DNA
<213> ORGANISM: Artificial Sequence
<220> FEATURE:
<223> OTHER INFORMATION: synthetic

<400> SEQUENCE: 8
acctaacgcc acttacccc                                      19

<210> SEQ ID NO 9
<211> LENGTH: 63
<212> TYPE: DNA
<213> ORGANISM: Artificial Sequence
<220> FEATURE:
<223> OTHER INFORMATION: synthetic

<400> SEQUENCE: 9
gtaatacgac tcactatagg atcgaaagat ttccgcggcc cgaaaggggg attagcgtta  60
ggt                                                               63

<210> SEQ ID NO 10

<211> LENGTH: 64
<212> TYPE: DNA
<213> ORGANISM: Artificial Sequence
<220> FEATURE:
<223> OTHER INFORMATION: synthetic

<400> SEQUENCE: 10
gtaatacgac tcactatagg atcgaaagat ttccgcatcc ccgaaagggt acatggcgtt    60
aggt                                                                 64

<210> SEQ ID NO 11
<211> LENGTH: 65
<212> TYPE: DNA
<213> ORGANISM: Artificial Sequence
<220> FEATURE:
<223> OTHER INFORMATION: synthetic

<400> SEQUENCE: 11
gtaatacgac tcactatagg atcgaaagat ttccgcaccc ccgaaagggg taagtggcgt    60
taggt                                                                65

<210> SEQ ID NO 12
<211> LENGTH: 94
<212> TYPE: DNA
<213> ORGANISM: Artificial Sequence
<220> FEATURE:
<223> OTHER INFORMATION: synthetic

<400> SEQUENCE: 12
gtaatacgac tcactatagt ccccttcgtc tagaggccca ggacaccgcc ttggtaaggc    60
ggtaacaggg gttcgaatcc cctagggac gcca                                 94

<210> SEQ ID NO 13
<211> LENGTH: 95
<212> TYPE: DNA
<213> ORGANISM: Artificial Sequence
<220> FEATURE:
<223> OTHER INFORMATION: synthetic

<400> SEQUENCE: 13
gtaatacgac tcactatagg cggggtggag cagcctggta gctcgtcggg ctcataaccc    60
gaagatcgtc ggttcaaatc cggccccgc aacca                                95

<210> SEQ ID NO 14
<211> LENGTH: 11
<212> TYPE: PRT
<213> ORGANISM: Artificial Sequence
<220> FEATURE:
<223> OTHER INFORMATION: synthetic

<400> SEQUENCE: 14

Phe Trp Ser His Pro Gln Phe Glu Lys Ser Thr
1               5                   10

<210> SEQ ID NO 15
<211> LENGTH: 12
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (1)..(1)
<223> OTHER INFORMATION: novel Fx substrate

<400> SEQUENCE: 15

Xaa Met Trp His Ser Pro Gln Phe Glu Lys Ser Thr
1               5                   10

<210> SEQ ID NO 16
<211> LENGTH: 11
<212> TYPE: PRT
<213> ORGANISM: Artificial Sequence
<220> FEATURE:
<223> OTHER INFORMATION: synthetic

<400> SEQUENCE: 16

Met Trp His Ser Pro Gln Phe Glu Lys Ser Thr
1               5                   10

<210> SEQ ID NO 17
<211> LENGTH: 11
<212> TYPE: PRT
<213> ORGANISM: Artificial Sequence
<220> FEATURE:
<223> OTHER INFORMATION: synthetic
<220> FEATURE:
<221> NAME/KEY: MOD_RES
<222> LOCATION: (1)..(1)
<223> OTHER INFORMATION: FORMYLATION

<400> SEQUENCE: 17

Met Trp His Ser Pro Gln Phe Glu Lys Ser Thr
1               5                   10

<210> SEQ ID NO 18
<211> LENGTH: 10
<212> TYPE: PRT
<213> ORGANISM: Artificial Sequence
<220> FEATURE:
<223> OTHER INFORMATION: synthetic

<400> SEQUENCE: 18

Trp His Ser Pro Gln Phe Glu Lys Ser Thr
1               5                   10

<210> SEQ ID NO 19
<211> LENGTH: 22
<212> TYPE: DNA
<213> ORGANISM: Artificial Sequence
<220> FEATURE:
<223> OTHER INFORMATION: synthetic

<400> SEQUENCE: 19
gtaatacgac tcactatagt cc                                               22

<210> SEQ ID NO 20
<211> LENGTH: 21
<212> TYPE: DNA
<213> ORGANISM: Artificial Sequence
<220> FEATURE:
<223> OTHER INFORMATION: synthetic

<400> SEQUENCE: 20
tggcgtcccc tagggattc g                                                 21

<210> SEQ ID NO 21
<211> LENGTH: 22
<212> TYPE: RNA
<213> ORGANISM: Artificial Sequence
<220> FEATURE:
<223> OTHER INFORMATION: synthetic

```
<400> SEQUENCE: 21
ggcucuguuc gcagagccgc ca                                            22

<210> SEQ ID NO 22
<211> LENGTH: 92
<212> TYPE: RNA
<213> ORGANISM: Artificial Sequence
<220> FEATURE:
<223> OTHER INFORMATION: synthetic

<400> SEQUENCE: 22
ggauggcgaa agccauuucc gcaggcccca uugcacuccg ggguauuggc guuagguggu   60
gguacgaggu ucgaauccuc guaccgcagc ca                                 92
```